United States Patent
Colinge et al.

(10) Patent No.: US 7,409,296 B2
(45) Date of Patent: Aug. 5, 2008

(54) SYSTEM AND METHOD FOR SCORING PEPTIDE MATCHES

(75) Inventors: Jacques Colinge, Neydens (FR); Alexandre Masselot, Carouge (CH)

(73) Assignee: Geneva Bioinformatics (Genebio), S.A., Geneva (CH)

( * ) Notice: Subject to any disclaimer, the term of this patent is extended or adjusted under 35 U.S.C. 154(b) by 745 days.

(21) Appl. No.: 10/624,531

(22) Filed: Jul. 23, 2003

(65) Prior Publication Data

US 2004/0143402 A1 Jul. 22, 2004

Related U.S. Application Data

(60) Provisional application No. 60/468,580, filed on May 7, 2003, provisional application No. 60/399,464, filed on Jul. 29, 2002.

(51) Int. Cl.
G01N 33/48 (2006.01)
G01N 31/00 (2006.01)
G01N 24/00 (2006.01)
C12Q 1/00 (2006.01)
C40B 50/02 (2006.01)

(52) U.S. Cl. ............................... 702/19; 702/22; 435/4; 506/24; 436/173

(58) Field of Classification Search ........................ None
See application file for complete search history.

(56) References Cited

U.S. PATENT DOCUMENTS

| | | | |
|---|---|---|---|
| 5,538,897 A | 7/1996 | Yates, III et al. | |
| 6,017,693 A | 1/2000 | Yates, III et al. | |
| 6,393,367 B1 | 5/2002 | Tang et al. | |
| 6,432,648 B1 * | 8/2002 | Blumenfeld et al. | ........... 435/6 |
| 6,489,121 B1 | 12/2002 | Skilling | |
| 6,489,608 B1 | 12/2002 | Skilling | |
| 6,582,965 B1 | 6/2003 | Townsend et al. | |
| 6,660,229 B2 | 12/2003 | Cantor et al. | |
| 6,800,449 B1 | 10/2004 | Haynes et al. | |
| 6,852,544 B2 | 2/2005 | Aebersold et al. | |
| 2002/0046002 A1 | 4/2002 | Tang et al. | |
| 2003/0052263 A1 | 3/2003 | Kaufman et al. | |
| 2003/0054408 A1 | 3/2003 | Kaufman et al. | |
| 2003/0153007 A1 | 8/2003 | Chen et al. | |
| 2004/0041089 A1 | 3/2004 | Halpern | |
| 2004/0153249 A1 | 8/2004 | Zhang et al. | |
| 2004/0175838 A1 | 9/2004 | Jarman et al. | |
| 2004/0195500 A1 | 10/2004 | Sachs et al. | |

FOREIGN PATENT DOCUMENTS

| EP | 1239288 | 9/2002 |
|---|---|---|
| JP | 2000-039436 | 2/2000 |
| JP | 2004-012355 | 1/2004 |
| JP | 2004-257922 | 9/2004 |

OTHER PUBLICATIONS

Bafna et al., Scope: a probalistic model for scoring tandem mass spectra against a peptide database, Bioinformatics, vol. 17, Suppl. 12001, pp. S13-S21 (date: 2001) annotated by examiner on Mar. 3, 2008.

Zhang et al., Profound: An expert system for protein identification using mass spectrometric peptide mapping information, Anal. Chem. 2000, 72, 2482-2489.

Yates, III, Database searching using mass spectrometry data, Electrophoresis, 1998, 19, 893-900.

Annaiah et al., "A Tool for Handling Tandem Mass Spectrometry Protein Database Search Results" URL:http://chemfacilities.chem.indiana.edu/facilities/proteomics/ASM S_2004_TPA014_abs.pdf.

Fu et al., "Exploiting the Kernel Trick to Correlate Fragment Ions for Peptide Identification Via Tandem Mass Spectrometry" URL:http://www.ingentaconnect.com/connect/oup/cabious/2004/00000020/00000012/art01948.

Citation: Electrophoresis. Dec. 1999;20(18):3551-67. Accession #: PMID: 10612281.

Citation: Anal Chem. Nov. 1, 2002;74(21):5593-9. Accession #: PMID: 12433093.

Citation: Anal Chem. Aug. 1, 2003;75(15):3792-8. Accession #: PMID: 14572045.

Citation: Anal Chem. Mar. 15, 2004;76(6):1664-71. Accession #: PMID: 15018565.

Citation: Anal Chem. Apr. 15, 1995:67(8):1426-36. Accession # PMID: 7741214.

Citation: Anal Chem. Apr. 15, 2004:76(8):2355-66. Accession #: PMID: 15080748.

Citation: Biol Mass Spectrom. Jun. 1993:22(6):338-45. Accession #: PMID: 8329463.

(Continued)

Primary Examiner—Lori A. Clow
Assistant Examiner—Anna Skibinsky
(74) Attorney, Agent, or Firm—Hunton & Williams, LLP

(57) ABSTRACT

The present invention relates to a system and method for scoring peptide matches. Embodiments of the present invention improves identification of peptides and proteins by introducing an appropriate signal detection based scoring system and what is believed to be the new concept of an extended match. To score a match between a first peptide and a second peptide, a stochastic model may be generated based on one or more match characteristics associated with the first peptide, the second peptide and their fragments. A first probability that the first peptide matches the second peptide, and second probability that the first peptide does not match the second peptide, may be calculated based on the stochastic model. And a match between the first peptide and the second peptide may be scored based at least in part on a ratio between the first probability and the second probability.

14 Claims, 20 Drawing Sheets

OTHER PUBLICATIONS

Citation: Rapid Commun Mass Spectrom. 1997;11(9); 1067-75. Accession #: PMID: 10582570.

Citation: J Comput Biol. 1999 Fall-Winter;6(3-4):327-42. Accession #: PMID: 10582570.

Citation: Proteomics. Mar. 2002;2(3):262-70. Accession #: PMID: 11921442.

Citation: Anal Chem. Jan. 15, 2004;76(2):267-75. Accession #: PMID: 14719870.

Citation: J Proteome Res. Jan.-Feb. 2004;3(1):32-6. Accession #: PMID: 14998160.

Citation: Bioinformatics. 2001;17 Suppl 1:S13-21. Accession #: PMID 11472988.

Citation: Sheng Wu Hua Xue Yu Sheng Wu Wu Li Xue Bao (Shanghai). Aug. 2003;35(8):734-40. Accession #: PMID: 12897969.

Citation: Anal Chem. Nov. 15, 2003;75(22):6251-64. Accession #: PMID: 14616009.

Jaques Colinge et al., "OLAV: Towards High-Throughput MS/MS Data Identification," GeneProt Inc., Pre de la Fontaine 2, CH-1219 Meyrin, Switzerland, pp. 1-30.

Jaques Colinge et al., "A Systematic Statistical Analysis of ion Trap Tandem Mass Spectra in View of Peptide Scoring," GeneProt Inc., Pre de la Fontaine 2, CH-1219 Meyrin, Switzerland.

Alexandre Masselot et al., "OLAV: General Applicability of Model-Based MS/MS Peptide Score Functions" GeneProt Inc., Pre de la Fontaine 2, CH-1219 Meyrin, Switzerland.

* cited by examiner

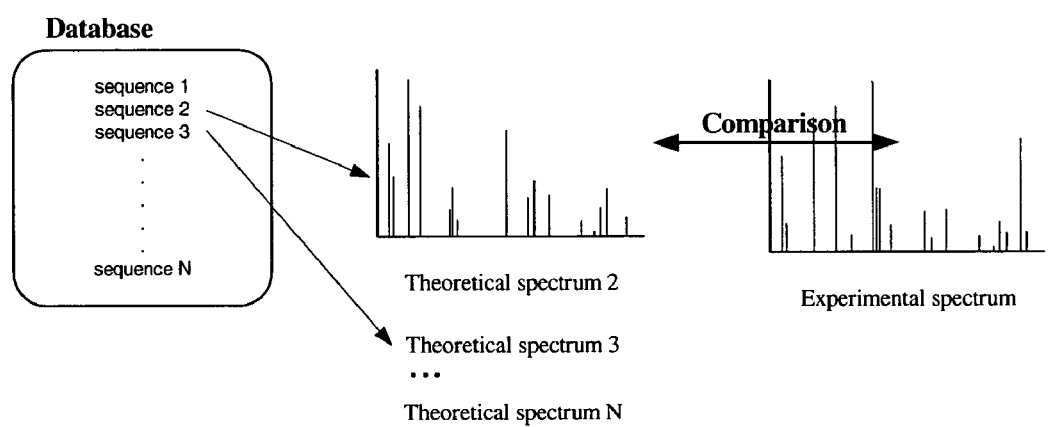
Figure 2a: database search

Figure 9: Null model.

SEQUENCE LISTING

```
<160> NUMBER OF SEQ ID NOS: 42

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Lys Ala His Trp Asn Asp Ala Ala Asn Gly
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Lys Arg His Asp Glu Asn Gln
 1               5

<210> SEQ ID NO 3
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Cys Asp Glu Phe Gly His Ile Lys Leu Met Asn Pro Gln Arg Ser
 1               5                  10                  15

Thr Val Trp Tyr Asn Lys His Phe Trp Tyr Ala Cys Asp Glu Phe Gly
             20                  25                  30

His Ile Lys Leu Met Asn Pro Gln Arg Ser Thr Val Trp Tyr
         35                  40                  45

<210> SEQ ID NO 4
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Cys Asp Glu Phe Gly His Ile Lys Leu Met Asn Pro Gln Arg Ser
 1               5                  10                  15

Thr Val Trp Tyr Lys Ala Cys Asp Glu Phe Gly His Ile Lys Leu Met
             20                  25                  30

Asn Pro Gln Arg Ser Thr Val Trp Tyr
         35                  40
```

```
<210> SEQ ID NO 5
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Cys Asp Glu Phe Gly His Ile Lys Leu Met Asn Pro Gln Arg Ser
 1               5                  10                  15

Thr Val Trp Tyr Asp His Ser Thr Tyr Ala Cys Asp Glu Phe Gly His
            20                  25                  30

Ile Lys Leu Met Asn Pro Gln Arg Ser Thr Val Trp Tyr
        35                  40                  45

<210> SEQ ID NO 6
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Cys Asp Glu Phe Gly His Ile Lys Leu Met Asn Pro Gln Arg Ser
 1               5                  10                  15

Thr Val Trp Tyr Ala Cys Asp Glu Phe Gly His Ile Lys Leu Met Asn
            20                  25                  30

Pro Gln Arg Ser Thr Val Trp Tyr Gly
        35                  40

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Cys Asp Glu Phe Gly His Ile Lys Leu Met Asn Pro Gln Arg Ser
 1               5                  10                  15

Thr Val Trp Tyr Lys Ala Cys Asp Glu Phe Gly His Ile Lys Leu Met
            20                  25                  30

Asn Pro Gln Arg Ser Thr Val Trp Tyr
        35                  40

<210> SEQ ID NO 8
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Cys Asp Glu Phe Gly His Ile Lys Leu Met Asn Pro Gln Arg Ser
 1               5                  10                  15

Thr Val Trp Tyr Ala Cys Asp Glu Phe Gly His Ile Lys Leu Met Asn
            20                  25                  30

Pro Gln Arg Ser Thr Val Trp Tyr Ala Cys Asp Glu Phe Gly His Ile
        35                  40                  45
```

```
Lys Leu Met Asn Pro Gln Arg Ser Thr Val Trp Tyr
        50                  55                  60

<210> SEQ ID NO 9
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Cys Asp Glu Phe Gly His Ile Lys Leu Met Asn Pro Gln Arg Ser
  1               5                  10                  15

Thr Val Trp Tyr Lys Ala Cys Asp Glu Phe Gly His Ile Lys Leu Met
             20                  25                  30

Asn Pro Gln Arg Ser Thr Val Trp Tyr
         35                  40

<210> SEQ ID NO 10
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Cys Asp Glu Phe Gly His Ile Lys Leu Met Asn Pro Gln Arg Ser
  1               5                  10                  15

Thr Val Trp Tyr Glu Asn Ala Cys Asp Glu Phe Gly His Ile Lys Leu
             20                  25                  30

Met Asn Pro Gln Arg Ser Thr Val Trp Tyr
             35                  40

<210> SEQ ID NO 11
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Cys Asp Glu Phe Gly His Ile Lys Leu Met Asn Pro Gln Arg Ser
  1               5                  10                  15

Thr Val Trp Tyr Gln Ala Cys Asp Glu Phe Gly His Ile Lys Leu Met
             20                  25                  30

Asn Pro Gln Arg Ser Thr Val Trp Tyr
         35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Cys Asp Glu Phe Gly His Ile Lys Leu Met Asn Pro Gln Arg Ser
  1               5                  10                  15

Thr Val Trp Tyr Asp Lys Asn Pro Ala Cys Asp Glu Phe Gly His Ile
```

```
                    20                  25                  30

Lys Leu Met Asn Pro Gln Arg Ser Thr Val Trp Tyr
        35                  40

<210> SEQ ID NO 13
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Cys Asp Glu Phe Gly His Ile Lys Leu Met Asn Pro Gln Arg Ser
1               5                   10                  15

Thr Val Trp Tyr Glu Ala Cys Asp Glu Phe Gly His Ile Lys Leu Met
            20                  25                  30

Asn Pro Gln Arg Ser Thr Val Trp Tyr
        35                  40

<210> SEQ ID NO 14
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Cys Asp Glu Phe Gly His Ile Lys Leu Met Asn Pro Gln Arg Ser
1               5                   10                  15

Thr Val Trp Tyr Ala Pro Ala Cys Asp Glu Phe Gly His Ile Lys Leu
            20                  25                  30

Met Asn Pro Gln Arg Ser Thr Val Trp Tyr
        35                  40

<210> SEQ ID NO 15
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Cys Asp Glu Phe Gly His Ile Lys Leu Met Asn Pro Gln Arg Ser
1               5                   10                  15

Thr Val Trp Tyr Cys Asp Glu His Lys Asn Gln Arg Ala Cys Asp Glu
            20                  25                  30

Phe Gly His Ile Lys Leu Met Asn Pro Gln Arg Ser Thr Val Trp Tyr
            35                  40                  45

<210> SEQ ID NO 16
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Cys Asp Glu Phe Gly His Ile Lys Leu Met Asn Pro Gln Arg Ser
1               5                   10                  15
```

```
Thr Val Trp Tyr Ala Pro Ala Cys Asp Glu Phe Gly His Ile Lys Leu
            20                  25                  30

Met Asn Pro Gln Arg Ser Thr Val Trp Tyr
            35                  40
```

<210> SEQ ID NO 17
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Ala Cys Asp Glu Phe Gly His Ile Lys Leu Met Asn Pro Gln Arg Ser
 1               5                  10                  15

Thr Val Trp Tyr Cys Asp Glu His Lys Asn Gln Arg Ala Cys Asp Glu
            20                  25                  30

Phe Gly His Ile Lys Leu Met Asn Pro Gln Arg Ser Thr Val Trp Tyr
            35                  40                  45
```

<210> SEQ ID NO 18
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Ala Cys Asp Glu Phe Gly His Ile Lys Leu Met Asn Pro Gln Arg Ser
 1               5                  10                  15

Thr Val Trp Tyr Ala Pro Ala Cys Asp Glu Phe Gly His Ile Lys Leu
            20                  25                  30

Met Asn Pro Gln Arg Ser Thr Val Trp Tyr
            35                  40
```

<210> SEQ ID NO 19
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Ala Cys Asp Glu Phe Gly His Ile Lys Leu Met Asn Pro Gln Arg Ser
 1               5                  10                  15

Thr Val Trp Tyr Cys Asp Glu His Lys Asn Gln Arg Ala Cys Asp Glu
            20                  25                  30

Phe Gly His Ile Lys Leu Met Asn Pro Gln Arg Ser Thr Val Trp Tyr
            35                  40                  45
```

<210> SEQ ID NO 20
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Ala Cys Asp Glu Phe Gly His Ile Lys Leu Met Asn Pro Gln Arg Ser
 1               5                  10                  15
```

Thr Val Trp Tyr Ala Cys Asp Glu Phe Gly His Ile Lys Leu Met Asn
            20                  25                  30

Pro Gln Arg Ser Thr Val Trp Tyr Ala Cys Asp Glu Phe Gly His Ile
        35                  40                  45

Lys Leu Met Asn Pro Gln Arg Ser Thr Val Trp Tyr
    50                  55                  60

<210> SEQ ID NO 21
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Cys Asp Glu Phe Gly His Ile Lys Leu Met Asn Pro Gln Arg Ser
 1               5                  10                  15

Thr Val Trp Tyr Tyr Ala Cys Asp Glu Phe Gly His Ile Lys Leu Met
            20                  25                  30

Asn Pro Gln Arg Ser Thr Val Trp Tyr
        35                  40

<210> SEQ ID NO 22
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Cys Asp Glu Phe Gly His Ile Lys Leu Met Asn Pro Gln Arg Ser
 1               5                  10                  15

Thr Val Trp Tyr Ala Cys Asp Glu Phe Gly His Ile Lys Leu Met Asn
            20                  25                  30

Pro Gln Arg Ser Thr Val Trp Tyr Ala Cys Asp Glu Phe Gly His Ile
        35                  40                  45

Lys Leu Met Asn Pro Gln Arg Ser Thr Val Trp Tyr
    50                  55                  60

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Cys Asp Glu Phe Gly His Ile Lys Leu Met Asn Pro Gln Arg Ser
 1               5                  10                  15

Thr Val Trp Tyr Asn Gly
            20

<210> SEQ ID NO 24
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 24

Ala Cys Asp Glu Phe Gly His Ile Lys Leu Met Asn Pro Gln Arg Ser
 1               5                  10                  15

Thr Val Trp Tyr Gln Ala Cys Asp Glu Phe Gly His Ile Lys Leu Met
             20                  25                  30

Asn Pro Gln Arg Ser Thr Val Trp Tyr
             35                  40

<210> SEQ ID NO 25
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Cys Asp Glu Phe Gly His Ile Lys Leu Met Asn Pro Gln Arg Ser
 1               5                  10                  15

Thr Val Trp Tyr His Met Trp Ala Cys Asp Glu Phe Gly His Ile Lys
             20                  25                  30

Leu Met Asn Pro Gln Arg Ser Thr Val Trp Tyr
         35                  40

<210> SEQ ID NO 26
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Cys Asp Glu Phe Gly His Ile Lys Leu Met Asn Pro Gln Arg Ser
 1               5                  10                  15

Thr Val Trp Tyr Cys Ala Cys Asp Glu Phe Gly His Ile Lys Leu Met
             20                  25                  30

Asn Pro Gln Arg Ser Thr Val Trp Tyr
             35                  40

<210> SEQ ID NO 27
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Cys Asp Glu Phe Gly His Ile Lys Leu Met Asn Pro Gln Arg Ser
 1               5                  10                  15

Thr Val Trp Tyr Cys Ala Cys Asp Glu Phe Gly His Ile Lys Leu Met
             20                  25                  30

Asn Pro Gln Arg Ser Thr Val Trp Tyr
             35                  40

<210> SEQ ID NO 28
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 28

Ala Cys Asp Glu Phe Gly His Ile Lys Leu Met Asn Pro Gln Arg Ser
1               5                   10                  15

Thr Val Trp Tyr Cys Ala Cys Asp Glu Phe Gly His Ile Lys Leu Met
            20                  25                  30

Asn Pro Gln Arg Ser Thr Val Trp Tyr
        35                  40

<210> SEQ ID NO 29
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Cys Asp Glu Phe Gly His Ile Lys Leu Met Asn Pro Gln Arg Ser
1               5                   10                  15

Thr Val Trp Tyr Cys Ala Cys Asp Glu Phe Gly His Ile Lys Leu Met
            20                  25                  30

Asn Pro Gln Arg Ser Thr Val Trp Tyr
        35                  40

<210> SEQ ID NO 30
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Cys Asp Glu Phe Gly His Ile Lys Leu Met Asn Pro Gln Arg Ser
1               5                   10                  15

Thr Val Trp Tyr Met Ala Cys Asp Glu Phe Gly His Ile Lys Leu Met
            20                  25                  30

Asn Pro Gln Arg Ser Thr Val Trp Tyr
        35                  40

<210> SEQ ID NO 31
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Cys Asp Glu Phe Gly His Ile Lys Leu Met Asn Pro Gln Arg Ser
1               5                   10                  15

Thr Val Trp Tyr Ser Ala Cys Asp Glu Phe Gly His Ile Lys Leu Met
            20                  25                  30

Asn Pro Gln Arg Ser Thr Val Trp Tyr
        35                  40

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Phe Pro Asn Cys Tyr Gln Lys Pro Cys Asn Arg
 1               5                  10

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Pro Cys Val Glu Ser Leu Val Asp Leu Tyr Phe Gln Thr Ile Pro
 1               5                  10                  15

Asp Tyr Gly Lys
            20

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Thr Gly Trp Arg Gln Ser Thr Arg Asp Ala Ser Tyr Thr
 1               5                  10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Thr Gly Trp Arg
 1               5

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Thr Arg
 1

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Ala Ser Tyr Thr
 1               5

```
<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Thr Gly Trp Arg Gln Ser Thr Arg
  1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Thr Arg Asp Ala Ser Tyr Thr
  1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Phe His Ile Leu Met Val Trp Tyr
  1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Asp Glu Gly Asn Gln Ser Thr
  1               5

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Cys Phe Ile Met Asp Glu Gly Leu Asn Gln Ser Thr Val Trp Tyr
  1               5                  10                  15
```

SYSTEM AND METHOD FOR SCORING PEPTIDE MATCHES

CROSS-REFERENCE TO RELATED APPLICATIONS

This patent application claims priority to U.S. provisional patent application No. 60/399,464, filed Jul. 29, 2002, and U.S. provisional patent application No. 60/468,580 entitled "Improved Scoring System For High-Throughput MS/MS Data", filed May 7, 2003, which are hereby incorporated by reference in their entirety.

FIELD OF THE INVENTION

The present invention relates generally to protein and peptide analysis and, more particularly, to a system and method for scoring a match of peptides based on their fragmentation or dissociation mass spectrum. More specifically, the present invention provides a sensitive and selective identification tool by exploiting the information stored in the mass spectra. This is achieved by introducing an appropriate signal detection based scoring system and what is believed to be the new concept of an extended match.

BACKGROUND OF THE INVENTION

Mass Spectrometry (MS) combined with database searching has become the preferred method for identifying proteins in the context of proteomics projects (See, e.g., Fenyo Beavis, Proteomics, A Trends Guide, July 2000, 22-26 Elsevier). In a typical proteome project, the proteins of interest are separated by one or two dimensional gel electrophoresis, or they can also be provided as mixtures of a small number of proteins fractionated by column chromatography. By using an enzyme, e.g. trypsin, the proteins are then digested into peptides. The measurement of the masses of the thus obtained peptides provides a peptide mass fingerprint (PMF). Such a PMF can be used to search a database or can be compared to another experimental PMF (See, e.g, Zhang, W. and Chait, B. T. 2000: *ProFound: an expert system for protein identification using mass spectrometric peptide mapping information*, Anal. Chem., 72:2482-2489, and James, P. ed. 2000: *Proteome Research: Mass Spectrometry*, Springer, Berlin). In certain circumstances, PFMs are not specific enough to the original protein to permit its non-ambiguous identification. In such cases, a second procedure may be applied, such as fragmentation (also referred to as dissociation) of the peptides (See, e.g., Papayannopoulos, I. A. 1995: *The interpretation of collision-induced dissociation mass spectra of peptides*, Mass Spectrometry Review, 14:49-73), which breaks the peptides into smaller molecules whose masses are measured. This procedure is called tandem mass spectrometry, tandem-MS, $MS^2$ or MS/MS. The masses of the fragments constitute a very specific data set that is used to identify the original peptide. By extension, the MS/MS data for several peptides of a protein constitute a very specific data set that is used to identify the original protein (See, e.g., Henzel, W. J. et al. 1993: *Identifying protein from two-dimensional gels by molecular mass searching of peptide fragments in protein sequence databases*, Proc. Natl. Acad. Sci. USA, 90:5011-5015, McCormack, A. L. et al. 1997: *Direct analysis and identification of proteins in mixture by LC/MS/MS and database searching at the low-femtomole level*, Anal. Chem., 69:767-776, James, P. ed. 2000: *Proteome Research: Mass Spectrometry*, Springer, Berlin).

Embodiments of the present invention improve the identification of the peptides based on MS/MS data, which comprise the measurement of the parent peptide mass and the measurement of the masses of its fragments.

A very common procedure when searching a database of biological sequences with mass spectrometry (See, e.g., Snyder, A. P. 2000: *Interpreting Protein Mass Spectra*, Oxford University Press, Washington D.C.) data is to compare the experimental spectra with theoretical spectra generated from the biological sequences stored in the database (See, e.g., James, P. ed. 2000: *Proteome Research: Mass Spectrometry*, Springer, Berlin). A scoring system is used to rate the matching between theoretical and experimental data. Typically, the database entry with the highest score is taken as the right representation of the experimental data. Ideally, the score is supplemented by a p-value estimating the probability to find a score equal or higher by random chance only. The p-value is used to give a measure of confidence to a match found in the database.

To date, the common practice for evaluating or scoring peptide matches has been manual analysis of spectra by trained technicians. While such methods are suitable for some mass spectrometry applications, manual analysis is a bottleneck in high throughput environments since data quality cannot be steadily maintained in high-throughput settings, causing automatic systems for scoring matches to suffer from low accuracy. High throughput systems for processing mass spectrometry data thus call for high quality scoring systems.

Scoring systems have several goals to meet. For example, one may be interested in searching large databases, such as an entire genome, as well as in detecting low-abundance proteins. Large databases require a very small rate of false positives since the erroneous peptide matches would be too numerous otherwise. This stresses the need for a very selective scoring system. In cases of low-abundance proteins, the MS data generally yielded is of lower quality compared to high abundance proteins. This in turn stresses the need for a very sensitive scoring system.

Currently available scoring systems lack selectivity because they can only take into consideration a small portion of the information available from mass spectra. For example, Bafna and Edwards, (See, e.g., Bafna, V. and Edwards, N. 2001: *SCOPE: a probabilistic model for scoring tandem mass spectra against a peptide database*, Bioinformatics, 17:S13-S21) consider only fragment masses, do not rely on parent peptide charge, and also do not calculate the likelihood ratio of observing a correct match versus observing a random match. Bafna and Edwards do not attempt to detect global patterns corresponding to structural constraints resulting from physical principles, like series of consecutive fragment matches. The same can also be said for the scoring system presented in Dancik et al. (See, e.g., Dancik, V., Addona, T. A., Clauser, K. R., Vath, J. E. and Pevzner, P. A. 1999: *De novo peptide sequencing viatandem massspectrometry: a graph-theoretica approach*, J. Comp. Biol., 6:327-342) and Havilio et al. (See, e.g., Havilio, M., Haddad, Y. and Smilansky, Z. 2003: *Intensity-based statistical scorer for tandem mass spectrometry*, Anal. Chem., 75:435-444), or other systems like that disclosed in European Patent Application No. EP 1 047 107 (assigned to Micromass Limited) and Zhang et al. (See, e.g., Zhang, N., Aebersold, R. and Schwikowski, B. 2002: *ProbId: A probabilistic algorithm to identify peptides through sequence database searching using tandem mass spectral data*, Proteomics, 2:1406-1412). In addition, Bafna and Edwards do not use optimal statistics in their scoring process.

Other available scoring systems include Mascot (See, e.g., Pappin, D. J. C., Hojrup, P. and Bleasby, A. J. 1993: *Rapid identification of proteins by peptide-mass fingerprinting*.

Curr. Biol., 3:327-332), Sequest (See, e.g., Eng, J. K., McCormack, A. L. and Yates, J. R. III 1994: *An approach to correlate tandem mass spectral data of peptides with amino acid sequences in a protein database*, J. Am. Soc. Mass Spectrom., 5:976-989, and U.S. Pat. No. 6,017,693), and SONAR MS/MS (available from ProteoMetrics Canada). The latter systems rely on ad hoc empirical definition of correlation between experimental spectra and theoretical peptide sequence.

Many authors, such as Anderson et al. (See, e.g, Anderson, D. C., Li, W., Payan, D. G. and Noble, W. S. 2003: *A new algorithm for the evaluation of shotgun peptide sequencing in proteomics: support vector machine classification of peptide MS/MS spectra and SEQUEST scores*, J. Proteome Res., 2:137-146), Keller et al. (See, e.g., Keller, A., Nesvizhskii, A. I., Kolker, E. and Aebersold, R. 2002: *Empirical statistical model to estimate the accuracy of peptide identification made by MSIMS and database search*, Anal. Chem., 74:5385-5392), Moore et al. (See, e.g., Moore, R. E, Young, M. K. and Lee, T. D. 2002: *Qscore: An algorithm for evaluating sequest database search results*, J. Am. Soc. Mass Spectrom., 13:378-386), and Sadygov et al. (See, e.g., Sadygov, R. G., Eng, J., Durr, E., Saraf, A., McDonald, H., MacCoss, M. J. and Yates, J. 2002: *Code development to improve the efficiency of automated MS/MS spectra interpretation*, J. Proteome Res., 1:211-215), have recently developed systems to validate Sequest results automatically. Keller et al. (supra) also applies to Mascot. These systems constitute a hybrid category of model-based systems (mainly multivariate statistics) developed on top of heuristic systems. Their performance is generally superior to the original heuristic system but far from optimal. Compare Keller et al. (See, e.g., Keller, A., Nesvizhskii, A. I., Kolker, E. and Aebersold, R. 2002: *Empirical statistical model to estimate the accuracy of peptide identification made by MS/MS and database search*, Anal. Chem., 74:5385-5392) and FIG. 10.

SUMMARY OF THE INVENTION

According to the present invention, a technique for scoring peptide matches is provided. In one particular exemplary embodiment, the technique may be realized by a method comprising the steps of: providing a first peptide and a second peptide; generating a stochastic model based on one or more match characteristics associated with each of the first peptide, the second peptide and at least one fragment of the first peptide or the second peptide; calculating a first probability that the first peptide matches the second peptide, based on the stochastic model; calculating a second probability that the first peptide does not match the second peptide, based on the stochastic model; and scoring a match between the first peptide and the second peptide based at least in part on a ratio between the first probability and the second probability.

In accordance with another of this particular exemplary embodiment of the present invention, the technique may be realized by/as a storage medium having code for causing a processor to score peptide matches, the storage medium comprising: code adapted to provide a first peptide and a second peptide; code adapted to generate a stochastic model based on one or more match characteristics associated with the first peptide, the second peptide and at least one fragment of the first peptide or the second peptide; code adapted to calculate a first probability that the first peptide matches the second peptide, based on the stochastic model; code adapted to calculate a probability that the first peptide does not match the second peptide, based on the stochastic model; and code adapted to score a match between the first peptide and the second peptide based at least in part on the ratio between the first probability and the second probability.

In accordance with yet another of this particular exemplary embodiment of the present invention, the technique may be realized by/as a system for scoring a match between a first peptide and a second peptide, the system comprising: means for generating a stochastic model based on one or more match characteristics associated with the first peptide, the second peptide and at least one fragment of the first peptide or the second peptide; means for calculating a first probability that the first peptide matches the second peptide, based on the stochastic model; means for calculating a probability that the first peptide does not match the second peptide, based on the stochastic model; and means for scoring a match between the first peptide and the second peptide based at least in part on the ratio between the first probability and the second probability.

In accordance with still another of this particular exemplary embodiment of the present invention, the technique may be realized by/as a system for scoring a match between a first peptide and a second peptide, the system comprising: a first calculation module that calculates a first probability that the first peptide matches the second peptide, based on the stochastic model; a second calculation module that calculates a probability that the first peptide does not match the second peptide, based on the stochastic model; and a scoring module that scores a match between the first peptide and the second peptide based at least in part on the ratio between the first probability and the second probability.

The present invention will now be described in more detail with reference to exemplary embodiments thereof as shown in the appended drawings. While the present invention is described below with reference to preferred embodiments, it should be understood that the present invention is not limited thereto. Those of ordinary skill in the art having access to the teachings herein will recognize additional implementations, modifications, and embodiments, as well as other fields of use, which are within the scope of the present invention as disclosed and claimed herein, and with respect to which the present invention could be of significant utility.

BRIEF DESCRIPTION OF THE DRAWINGS

In order to facilitate a fuller understanding of the present invention, reference is now made to the appended drawings. These drawings should not be construed as limiting the present invention, but are intended to be exemplary only.

FIG. 2a illustrates a procedure for the identification of proteins, involving searching a database of biological sequences with mass spectrometry data and comparing the experimental spectra with theoretical spectra generated from the biological sequences stored in the database.

FIG. 5 provides examples of MS spectra. FIG. 5A shows an example of a mass spectrum, while

DETAILED DESCRIPTION OF THE INVENTION

Figure 1:
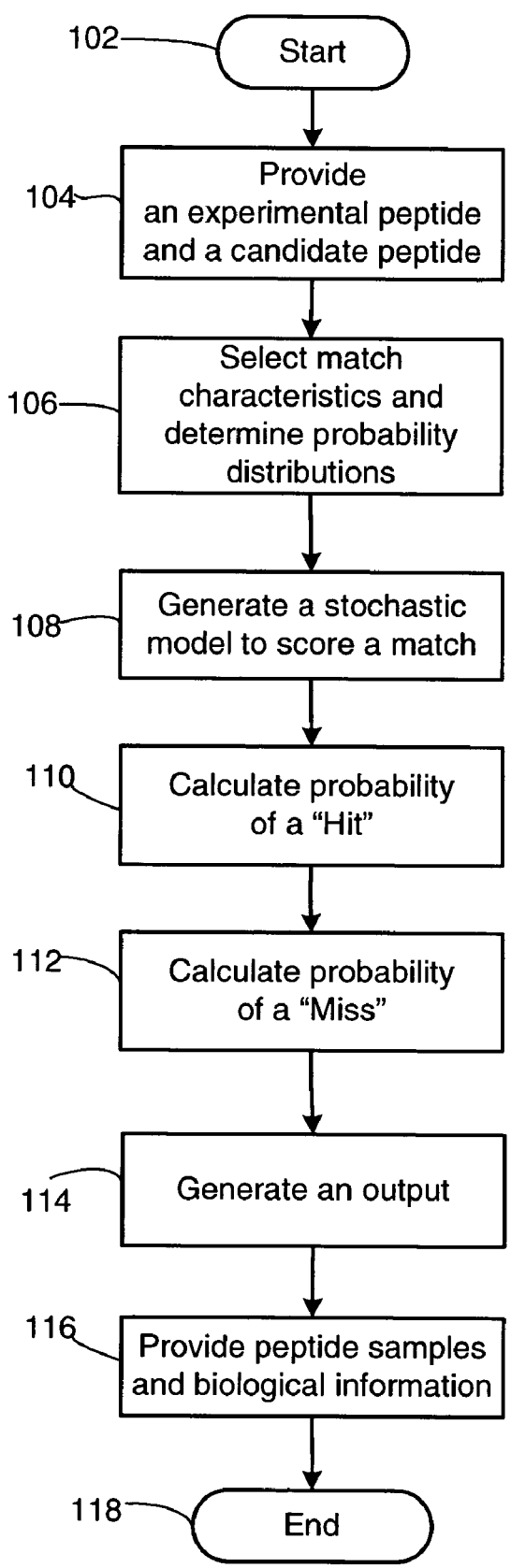
FIG. 1 is a flow chart illustrating an exemplary method for scoring peptide matches in accordance with one embodiment of the present invention.

Disclosed herein is a new system and method designed to score peptide matches. This system defines a match as a tuple of various observations, i.e. the simultaneous observation of different elementary events. By using a stochastic model to describe the observed events, the invention generates a score for a match.

Before a detailed description of the present invention, definitions of a number of terms are set forth below.

Proteins are linear, unbranched polymers of amino acids. As used herein, a "protein sequence" represents the identity and order of the amino acid residues that make up a protein. A protein sequence may be represented as a list of amino acids, for example. A protein sequence is usually ordered from the N-terminal to the C-terminal.

As used herein, a "peptide" is part of a protein, typically obtained by enzymatic digestion. In terms of sequence, a peptide sequence is a sub-sequence of the entire protein sequence. A peptide sequence represents the identity and order of the amino acid residues that make up a peptide. Depending on the context, it is sometimes important to explicitly distinguish an experimental peptide, typically the one whose mass has been physically measured by mass spectrometry, from a theoretical peptide, typically a peptide sequence found in a database. In the context of the present invention, it should be appreciated that a "peptide" (e.g. an experimental peptide or a candidate or theoretical peptide) or a protein may be represented in any suitable way. For example, a peptide is generally represented by a physical property, such as its mass, or a series of masses as described in a mass spectrum. Providing or obtaining a peptide typically includes for example providing or obtaining a mass spectrum (for example, provided as a list of masses), since the mass spectrum describes physical properties of the peptide.

As used herein, a "parent peptide" is a peptide that is fragmented in tandem mass spectrometry, resulting in a plurality of peptide fragments or fragment ions.

As used herein, an "experimental peptide" is a peptide which is to be identified or matched (e.g. matched to data, or matched to another peptide). The experimental peptide may also be referred to as an unknown peptide. An experimental spectrum is an experimentally measured mass spectrum. Generally, an experimental spectrum refers to the masses or mass over charge ratios measured, i.e. the experimental signal has been processed to extract the latter quantities.

As used herein, a "candidate peptide" may be any peptide, including a "theoretical peptide" or an experimentally determined peptide. Typically, a "candidate peptide" is a peptide which is evaluated for a possible match with an experimental peptide. A "theoretical peptide" may be a peptide which is predicted but not experimentally determined, or a peptide which is generated randomly, or a peptide which is part of a known protein, which protein might be found in a database. A theoretical spectrum is a list of masses and/or masses over charge ratios computed from the peptide sequence. If protein modifications are considered, then the theoretical spectra must be computed accordingly (see Table 1). When a candidate peptide is an experimentally determined peptide, it may be a known peptide. Alternatively, the candidate peptide may be an unidentified peptide, as used in the context of the present invention when scoring the match of two experimental spectra.

Table 1 illustrates example of modified peptide with several modifications of different sorts (fixed, variable with and without modifications). Each combination of modifications is reported by the associated peptide total mass and, on a second line, the locations of the variable modifications.

TABLE 1

Peptide AKAHWNDAANG (SEQ ID NO: 1)

Modifications:

1. acetylation; forced to occur on the amino acid at position 2 (K)
2. methylation, variable, occurring on [CKRHDENQ] (SEQ ID NO: 2) (i.e. positions 4, 6, 7 and 10)
3. deamidation, variable, occurring on [N] followed by a [G] (i.e. position 10)
4. oxidation, variable, occurring on [HMW] (i.e. positions 4 and 5)

Remarks:

There are the following conflict sites:

at position 4 between modifications (2) and (4)
at position 10, between (2) and (3)

TABLE 1-continued

And no conflict sites:

at position 5, for modification (4)
at position 6 and 7 for (2)
mass=1195.54 : 1195.54 : AK(1)AHWNDAANG
mass=1209.55 : (2)@3, 1209.55 : AK(1)AH(2)WNDAANG
mass=1211.53 : (4)@3, 1211.53 : AK(1)AH(4)WNDAANG
mass=1209.55 : (2)@9, 1209.55 : AK(1)AHWNDAAN(2)G
mass=1223.57 : (2)@3, (2)@9, 1223.57 : AK(1)AH(2)WNDAAN(2)G
mass=1225.55 : (4)@3, (2)@9, 1225.55 : AK(1)AH(4)WNDAAN(2)G
mass=1196.52 : (3)@9, 1196.52 : AK(1)AHWNDAAN(3)G
mass=1210.54 : (2)@3, (3)@9, 1210.54 : AK(1)AH(2)WNDAAN(3)G
mass=1212.52 : (4)@3, (3)@9, 1212.52 : AK(1)AH(4)WNDAAN(3)G
mass=1209.55 : (2)x1, 1209.55 : AK(1)AHWND(2)AANG
1209.55 : AK(1)AHWN(2)DAANG
mass=1223.57 : (2)@3, (2)x1, 1223.57 : AK(1)AH(2)WND(2)AANG
1223.57 : AK(1)AH(2)WN(2)DAANG
mass=1225.55 : (4)@3, (2)x1, 1225.55 : AK(1)AH(4)WND(2)AANG
1225.55 : AK(1)AH(4)WN(2)DAANG
mass=1223.57 : (2)@9, (2)x1, 1223.57 : AK(1)AHWND(2)AAN(2)G
1223.57 : AK(1)AHWN(2)DAAN(2)G
mass=1237.58 : (2)@3, (2)@9, (2)x1,
1237.58 : AK(1)AH(2)WND(2)AAN(2)G
1237.58 : AK(1)AH(2)WN(2)DAAN(2)G
mass=1239.56 : (4)@3, (2)@9, (2)x1,
1239.56 : AK(1)AH(4)WND(2)AAN(2)G
1239.56 : AK(1)AH(4)WN(2)DAAN(2)G
mass=1210.54 : (3)@9, (2)x1, 1210.54 : AK(1)AHWND(2)AAN(3)G
1210.54 : AK(1)AHWN(2)DAAN(3)G
mass=1224.55 : (2)@3, (3)@9, (2)x1,
1224.55 : AK(1)AH(2)WND(2)AAN(3)G
1224.55 : AK(1)AH(2)WN(2)DAAN(3)G
mass=1226.53 : (4)@3, (3)@9, (2)x1,
1226.53 : AK(1)AH(4)WND(2)AAN(3)G
1226.53 : AK(1)AH(4)WN(2)DAAN(3)G
mass=1223.57 : (2)x2, 1223.57 : AK(1)AHWN(2)D(2)AANG
mass=1237.58 : (2)@3, (2)x2, 1237.58 : AK(1)AH(2)WN(2)D(2)AANG
mass=1239.56 : (4)@3, (2)x2, 1239.56 : AK(1)AH(4)WN(2)D(2)AANG
mass=1237.58 : (2)@9, (2)x2, 1237.58 : AK(1)AHWN(2)D(2)AAN(2)G
mass=1251.6 : (2)@3, (2)@9, (2)x2,
1251.6 : AK(1)AH(2)WN(2)D(2)AAN(2)G
mass=1253.58 : (4)@3, (2)@9, (2)x2,
1253.58 : AK(1)AH(4)WN(2)D(2)AAN(2)G
mass=1224.55 : (3)@9, (2)x2, 1224.55 : AK(1)AHWN(2)D(2)AAN(3)G
mass=1238.57 : (2)@3, (3)@9, (2)x2,
1238.57 : AK(1)AH(2)WN(2)D(2)AAN(3)G
mass=1240.55 : (4)@3, (3)@9, (2)x2,
1240.55 : AK(1)AH(4)WN(2)D(2)AAN(3)G
mass=1211.53 : (4)x1, 1211.53 : AK(1)AHW(4)NDAANG
mass=1225.55 : (2)@3, (4)x1, 1225.55 : AK(1)AH(2)W(4)NDAANG
mass=1227.53 : (4)@3, (4)x1, 1227.53 : AK(1)AH(4)W(4)NDAANG
mass=1225.55 : (2)@9, (4)x1, 1225.55 : AK(1)AHW(4)NDAAN(2)G
mass=1239.56 : (2)@3, (2)@9, (4)x1,
1239.56 : AK(1)AH(2)W(4)NDAAN(2)G
mass=1241.54 : (4)@3, (2)@9, (4)x1,
1241.54 : AK(1)AH(4)W(4)NDAAN(2)G
mass=1212.52 : (3)@9, (4)x1, 1212.52 : AK(1)AHW(4)NDAAN(3)G
mass=1226.53 : (2)@3, (3)@9, (4)x1,
1226.53 : AK(1)AH(2)W(4)NDAAN(3)G
mass=1228.51 : (4)@3, (3)@9, (4)x1,
1228.51 : AK(1)AH(4)W(4)NDAAN(3)G
mass=1225.55 : (2)x1, (4)x1, 1225.55 : AK(1)AHW(4)ND(2)AANG
1225.55 : AK(1)AHW(4)N(2)DAANG
mass=1239.56 : (2)@3, (2)x1, (4)x1,
1239.56 : AK(1)AH(2)W(4)ND(2)AANG
1239.56 : AK(1)AH(2)W(4)N(2)DAANG

TABLE 1-continued mass=1241.54 : (4)@3, (2)x1, (4)x1,
1241.54 : AK(1)AH(4)W(4)ND(2)AANG
1241.54 : AK(1)AH(4)W(4)N(2)DAANG
mass=1239.56 : (2)@9, (2)x1, (4)x1,
1239.56 : AK(1)AHW(4)ND(2)AAN(2)G
1239.56 : AK(1)AHW(4)N(2)DAAN(2)G
mass=1253.58 : (2)@3, (2)@9, (2)x1, (4)x1,
1253.58 : AK(1)AH(2)W(4)ND(2)AAN(2)G
1253.58 : AK(1)AH(2)W(4)N(2)DAAN(2)G
mass=1255.56 : (4)@3, (2)@9, (2)x1, (4)x1,
1255.56 : AK(1)AH(4)W(4)ND(2)AAN(2)G
1255.56 : AK(1)AH(4)W(4)N(2)DAAN(2)G
mass=1226.53 : (3)@9, (2)x1, (4)x1,
1226.53 : AK(1)AHW(4)ND(2)AAN(3)G
1226.53 : AK(1)AHW(4)N(2)DAAN(3)G
mass=1240.55 : (2)@3, (3)@9, (2)x1, (4)x1,
1240.55 : AK(1)AH(2)W(4)ND(2)AAN(3)G
1240.55 : AK(1)AH(2)W(4)N(2)DAAN(3)G
mass=1242.53 : (4)@3, (3)@9, (2)x1, (4)x1,
1242.53 : AK(1)AH(4)W(4)ND(2)AAN(3)G
1242.53 : AK(1)AH(4)W(4)N(2)DAAN(3)G
mass=1239.56 : (2)x2, (4)x1, 1239.56 : AK(1)AHW(4)N(2)D(2)AANG
mass=1253.58 : (2)@3, (2)x2, (4)x1,
1253.58 : AK(1)AH(2)W(4)N(2)D(2)AANG
mass=1255.56 : (4)@3, (2)x2, (4)x1,
1255.56 : AK(1)AH(4)W(4)N(2)D(2)AANG
mass=1253.58 : (2)@9, (2)x2, (4)x1,
1253.58 : AK(1)AHW(4)N(2)D(2)AAN(2)G
mass=1267.59 : (2)@3, (2)@9, (2)x2, (4)x1,
1267.59 : AK(1)AH(2)W(4)N(2)D(2)AAN(2)G
mass=1269.57 : (4)@3, (2)@9, (2)x2, (4)x1,
1269.57 : AK(1)AH(4)W(4)N(2)D(2)AAN(2)G
mass=1240.55 : (3)@9, (2)x2, (4)x1,
1240.55 : AK(1)AHW(4)N(2)D(2)AAN(3)G
mass=1254.56 : (2)@3, (3)@9, (2)x2, (4)x1,
1254.56 : AK(1)AH(2)W(4)N(2)D(2)AAN(3)G
mass=1256.54 : (4)@3, (3)@9, (2)x2, (4)x1,
1256.54 : AK(1)AH(4)W(4)N(2)D(2)AAN(3)G As used herein, a "protein modification" is a modification of the chemical structure of the protein. Such a modification may have a biological origin (post translational modifications) or result from a chemical modification or protein degradation, e.g. due to an experimental protocol used. They modify both the peptide masses as well as the MS/MS spectra (See, e.g., Table 2 and Turner, J. P. et al. 1997: *Letter code, structure and derivatives of amino acids*, Molecular Biotechnology, 8:233-247).

Table 2 illustrates examples of modifications. The format uses 2 lines per modification. First line: modification number, short name, long name, [characters before: characters at the modification site: characters after]. A ^ (hat) character means "not", i.e. every character but the ones after ^. Second line: is N-terminal (True/False)—is C-terminal (True/False), correction on the mono-isotopic amino acid mass: correction on the average amino acid mass.

As used herein, a variable modification is a modification that may or may not be present at a given amino acid residue. A fixed modification is a modification that substantially always appears at an amino acid residue.

TABLE 2

(SEQ ID NOS 3-31, respectively in order of appearance)

0 ACET_nterm (Acetylation_nterm) [ACDEFGHIKLMNPQRSTVWY:^NKHFWY:ACDEFGHIKLMNPQRSTVWY]
T---F 42.0106:42.0373

1 ACET_core (Acetylation_core) [ACDEFGHIKLMNPQRSTVWY:K:ACDEFGHIKLMNPQRSTVWY]
F---F 42.0106:42.0373

TABLE 2-continued (SEQ ID NOS 3-31, respectively in order of appearance)

2 PHOS (Phosphorylation) [ACDEFGHIKLMNPQRSTVWY:DHSTY:ACDEFGHIKLMNPQRSTVWY]
F---F 79.9663:79.9799
3 AMID (Amidation) [ACDEFGHIKLMNPQRSTVWY:ACDEFGHIKLMNPQRSTVWY:G]
F---T −0.984:−0.9847
4 BIOT (Biotin) [ACDEFGHIKLMNPQRSTVWY:K:ACDEFGHIKLMNPQRSTVWY]
F---T 226.078:226.293
5 CAM__nterm (Carbamylation__nterm)
[ACDEFGHIKLMNPQRSTVWY:ACDEFGHIKLMNPQRSTVWY:ACDEFGHIKLMNPQRSTVWY]
T---F 43.0058:43.025
6 CAM__core (Carbamylation__core) [ACDEFGHIKLMNPQRSTVWY:K:ACDEFGHIKLMNPQRSTVWY]
F---F 43.0058:43.025
7 CARB (Carboxylation) [ACDEFGHIKLMNPQRSTVWY:EN:ACDEFGHIKLMNPQRSTVWY]
F---F 43.9898:44.0098
8 PYRR (Pyrrolidone__carboxylic__acid) [ACDEFGHIKLMNPQRSTVWY:Q:ACDEFGHIKLMNPQRSTVWY]
T---F −17.0266:−17.0306
9 HYDR (Hydroxylation) [ACDEFGHIKLMNPQRSTVWY:DKNP:ACDEFGHIKLMNPQRSTVWY]
F---F 15.9949:15.9994
10 GGLU (Gamma-carboxyglutamic__acid) [ACDEFGHIKLMNPQRSTVWY:E:ACDEFGHIKLMNPQRSTVWY]
F---F 43.9898:44.0098
11 METH__nterm (Methylation__nterm) [ACDEFGHIKLMNPQRSTVWY:AP:ACDEFGHIKLMNPQRSTVWY]
T---F 14.0157:14.0269
12 METH__core (Methylation__core) [ACDEFGHIKLMNPQRSTVWY:CDEHKNQR:ACDEFGHIKLMNPQRSTVWY]
F---F 14.0157:14.0269
13 DIMETH__nterm (Di-Methylation__nterm) [ACDEFGHIKLMNPQRSTVWY:AP:ACDEFGHIKLMNPQRSTVWY]
T---F 28.0314:28.0538
14 DIMETH__core (Di-Methylation__core) [ACDEFGHIKLMNPQRSTVWY:CDEHKNQR:ACDEFGHIKLMNPQRSTVWY]
F---F 28.0314:28.0538
15 TRIMETH__nterm (Tri-Methylation__nterm) [ACDEFGHIKLMNPQRSTVWY:AP:ACDEFGHIKLMNPQRSTVWY]
T---F 42.0471:42.0807
16 TRIMETH__core (Tri-Methylation__core) [ACDEFGHIKLMNPQRSTVWY:CDEHKNQR:ACDEFGHIKLMNPQRSTVWY]
F---F 42.0471:42.0807
17 SULF__nterm (Sulfation__nterm) [ACDEFGHIKLMNPQRSTVWY:ACDEFGHIKLMNPQRSTVWY:ACDEFGHIKLMNPQRSTVWY]
T---F 79.9568:80.0642
18 SULF (Sulfation__core) [ACDEFGHIKLMNPQRSTVWY:Y:ACDEFGHIKLMNPQRSTVWY]
F---F 79.9568:80.0642
19 FORM (Formylation) [ACDEFGHIKLMNPQRSTVWY:ACDEFGHIKLMNPQRSTVWY:ACDEFGHIKLMNPQRSTVWY]
T---F 27.9949:28.0104
20 DEAM__N (Deamidation__N) [ACDEFGHIKLMNPQRSTVWY:N:G]
F---F 0.984:0.9847
21 DEAM__Q (Deamidation__Q) [ACDEFGHIKLMNPQRSTVWY:Q:ACDEFGHIKLMNPQRSTVWY]
F---F 0.984:0.9847
22 Oxydation (Oxydation) [ACDEFGHIKLMNPQRSTVWY:HMW:ACDEFGHIKLMNPQRSTVWY]
F---F 15.9949:15.999
23 Cys__CM (Carboxymethyl__cysteine) [ACDEFGHIKLMNPQRSTVWY:C:ACDEFGHIKLMNPQRSTVWY]
F---F 58.0055:58.0367
24 Cys__CAM (Carboxyamidomethyl__cysteine) [ACDEFGHIKLMNPQRSTVWY:C:ACDEFGHIKLMNPQRSTVWY]
F---F 57.0215:57.052
25 Cys__PE (Pyridyl-ethyl__cysteine) [ACDEFGHIKLMNPQRSTVWY:C:ACDEFGHIKLMNPQRSTVWY]
F---F 105.058:105.145
26 Cys__PAM (Propionamide__cysteine) [ACDEFGHIKLMNPQRSTVWY:C:ACDEFGHIKLMNPQRSTVWY]
F---F 71.0371:71.0788
27 MSO (Methionine__sulfoxide) [ACDEFGHIKLMNPQRSTVWY:M:ACDEFGHIKLMNPQRSTVWY]
F---F 15.9949:15.9994
28 HSL (Homoserine__Lactone) [ACDEFGHIKLMNPQRSTVWY:S:ACDEFGHIKLMNPQRSTVWY]
F---F 12.9617:13.0189

As used herein, an "ion series" is a type of peptide fragmentation or dissociation (See, e.g., Tables 3 and 4, Papayannopoulos, I. A. 1995: *The interpretation of collision-induced dissociation mass spectra of peptides*, Mass Spectrometry Review, 14:49-73).

Table 3 illustrates fragmentation spectrum (masses rounded to unity) of a peptide with cysteine modified (Cys_CAM, +57 Daltons) and glutamine (Q) deamidated (+1 Dalton). The naming of the ion series is standard except series names followed by a star. The latter means "any number of losses". Masses equal to −1 corresponds to impossible ions.

Table 4 is the theoretical MS/MS spectrum of peptide tryptic FPNCYQKPCNR (SEQ ID NO: 32). Modification $Cys_{13}$ CAM (iodoacetamide, +57Da) used to break di-sulfur bonds have been considered as a variable modification. The rule is that every cysteine (C) can be modified. The total mass of the peptide is in the column labeled as "Total". The two cases where one cysteine only is modified share the same total mass. As the fragment masses are needed, the exact location of the modifications is necessary.

Figure 2B:
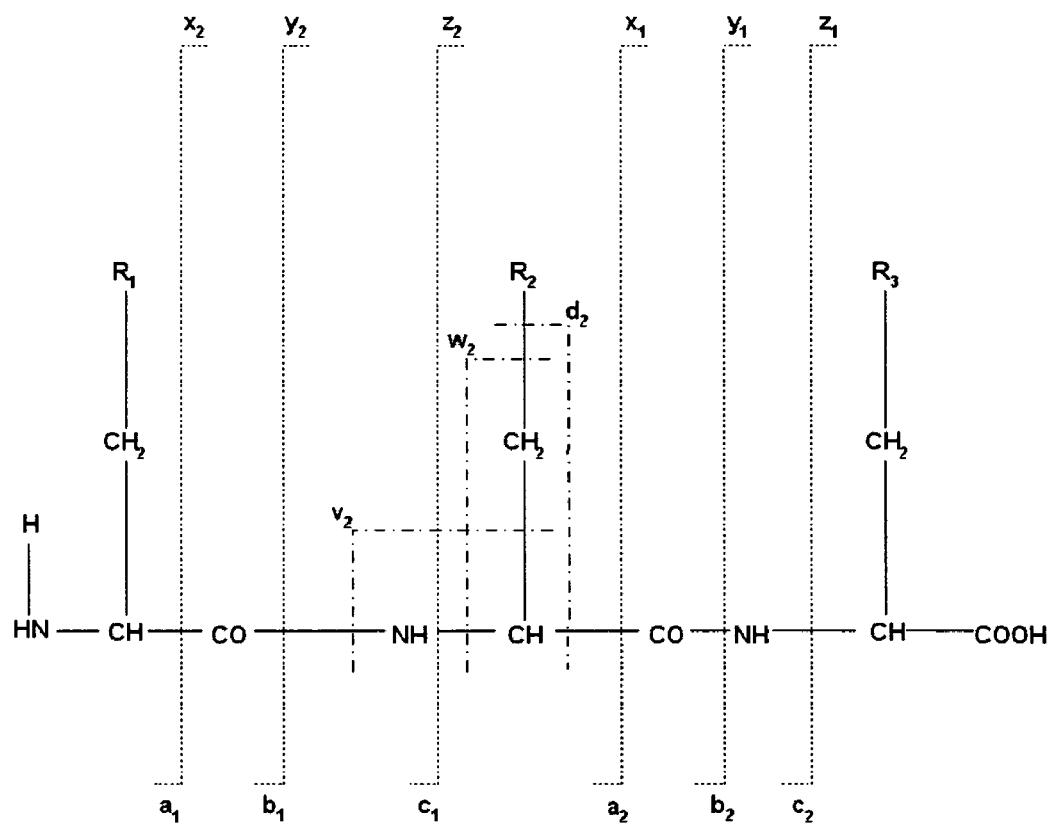
FIG. 2b shows the different peptide fragmentation ions, and examples of nomenclature attributed thereto.

A peptide may be fragmented at different locations. Each generic location corresponds a so-called ion series as illustrated in FIG. 2b. For complete nomenclature, see Spengler, B. 1997: *Post-source decay analysis in matrix-assisted laser desorption/ionization mass spectrometry of biomolecules*. J. Mass Spectrom., 32:1019-1036, Falik et al. 1993, Johnson, R. S. et al. 1988: *Collision-induced fragmentation of (M+H)+ ions of peptides. Side chain specific sequence ions*. Intl. J. Mass Spectrom, and Ion Processes, 86:137-154, DeGnore, J. P. and Qin, J. 1998: *Fragmentation of phosphopeptides in an ion trap mass spectrometer*, J. Am. Soc. Mass Spectrom., 9:1175-1188, and Papayannopoulos, I. A. 1995: *The inter-* pretation of collision-induced dissociation mass spectra of peptides, Mass Spectrometry Review, 14:49-73, for a complete description. In particular, it is common to denote by $b_i^{++}$ doubly charged b-ions, by $b_i^*$ b-ions that have lost $NH_3$ and by $b_i^\circ$ b-ions that have lost $H_2O$ (same notation for the series a, c, x, y, z). Each type of mass spectrometer produces a specific set of ion series. This may also depend on the charge state of the parent peptide.

In the case where the mass spectrometry instrument used is an LC-MS/MS or HPLC-MS/MS instrument (See, e.g., James, P. ed. 2000: *Proteome Research: Mass Spectrometry*, Springer, Berlin), each peptide experimentally measured and fragmented comes with an "elution time", i.e. its retention time in the chromatography system attached to the mass spectrometer (See, e.g., Sakamoto, Y., Kawakami, N. and Sasagawa, T. 1988: *Prediction of peptide retention times*, J Chromatogr., 442:69-79, Mant, C. T., Zhou, N. E. and Hodges, R. S. 1989: Correlation of protein retention times in reversed-phase chromatography with polypeptide chain length and hydrophobicity, J. Chromatogr., 476:363-75).

TABLE 3

(SEQ ID NO: 33)

|   | E | P | C | V | E | S | L | V | D | L | Y |
|---|---|---|---|---|---|---|---|---|---|---|---|
| a | 102 | 199 | 359 | 458 | 587 | 674 | 787 | 886 | 1001 | 1115 | 1278 |
| a-NH3* | −1 | −1 | −1 | −1 | −1 | −1 | −1 | −1 | −1 | −1 | −1 |
|   | −1 | −1 | −1 | −1 | −1 | −1 | −1 | −1 | −1 | −1 | −1 |
| a-H2O* | −1 | −1 | −1 | −1 | −1 | 656 | 769 | 868 | 983 | 1097 | 1260 |
|   | −1 | −1 | −1 | −1 | −1 | −1 | −1 | −1 | −1 | −1 | −1 |
| a++ | 52 | 100 | 180 | 230 | 294 | 338 | 394 | 444 | 501 | 558 | 639 |
| b | 130 | 227 | 387 | 486 | 615 | 702 | 815 | 914 | 1029 | 1143 | 1306 |
| b-NH3* | −1 | −1 | −1 | −1 | −1 | −1 | −1 | −1 | −1 | −1 | −1 |
|   | −1 | −1 | −1 | −1 | −1 | −1 | −1 | −1 | −1 | −1 | −1 |
| b-H2O* | −1 | −1 | −1 | −1 | −1 | 684 | 797 | 896 | 1011 | 1125 | 1288 |
|   | −1 | −1 | −1 | −1 | −1 | −1 | −1 | −1 | −1 | −1 | −1 |
| b++ | 66 | 114 | 194 | 244 | 308 | 352 | 408 | 458 | 515 | 572 | 653 |
| y | 2374 | 2245 | 2148 | 1988 | 1889 | 1760 | 1673 | 1560 | 1461 | 1346 | 1233 |
| y-NH3* | 2357 | 2228 | 2131 | 1971 | 1872 | 1743 | 1656 | 1543 | 1444 | 1329 | 1216 |
|   | 2340 | 2211 | 2114 | 1954 | 1855 | 1726 | 1639 | 1526 | 1427 | 1312 | 1199 |
| y-H2O* | 2356 | 2227 | 2130 | 1970 | 1871 | 1742 | 1655 | 1542 | 1443 | 1328 | 1215 |
|   | 2338 | 2209 | 2112 | 1952 | 1853 | 1724 | −1 | −1 | −1 | −1 | −1 |
| y++ | 1188 | 1123 | 1075 | 995 | 945 | 880 | 837 | 780 | 731 | 673 | 617 |

|   | F | Q | T | I | P | D | Y | G | K |
|---|---|---|---|---|---|---|---|---|---|
| a | 1425 | 1554 | 1655 | 1768 | 1865 | 1980 | 2143 | 2200 | 2328 |
| a-NH3* | −1 | 1537 | 1638 | 1751 | 1848 | 1963 | 2126 | 2183 | 2311 |
|   | −1 | −1 | −1 | −1 | −1 | −1 | −1 | −1 | 2294 |
| a-H2O* | 1407 | 1536 | 1637 | 1750 | 1847 | 1962 | 2125 | 2182 | 2310 |
|   | −1 | −1 | 1619 | 1732 | 1829 | 1944 | 2107 | 2164 | 2292 |
| a++ | 713 | 777 | 828 | 884 | 933 | 990 | 1072 | 1101 | 1165 |
| b | 1453 | 1582 | 1683 | 1796 | 1893 | 2008 | 2171 | 2228 | 2356 |
| b-NH3* | −1 | 1565 | 1666 | 1779 | 1876 | 1991 | 2154 | 2211 | 2339 |
|   | −1 | −1 | −1 | −1 | −1 | −1 | −1 | −1 | 2322 |
| b-H2O* | 1435 | 1564 | 1665 | 1778 | 1875 | 1990 | 2153 | 2210 | 2338 |
|   | −1 | −1 | 1647 | 1760 | 1857 | 1972 | 2135 | 2192 | 2320 |
| b++ | 727 | 791 | 842 | 898 | 947 | 1004 | 1086 | 1115 | 1179 |
| y | 1070 | 922 | 793 | 692 | 579 | 482 | 367 | 204 | 147 |
| y-NH3* | 1052 | 905 | 776 | 675 | 562 | 465 | 350 | 187 | 130 |
|   | 1035 | 888 | −1 | −1 | −1 | −1 | −1 | −1 | −1 |
| y-H2O* | 1052 | 904 | 775 | −1 | −1 | −1 | −1 | −1 | −1 |
|   | −1 | −1 | −1 | −1 | −1 | −1 | −1 | −1 | −1 |
| y++ | 535 | 462 | 397 | 347 | 290 | 242 | 184 | 103 | 74 |

TABLE 4

(SEQ ID NO: 32)

|   | F | P | N | C | Y | Q | K | P | C | N | R | Total |
|---|---|---|---|---|---|---|---|---|---|---|---|---|
| b | 148.1 | 245.1 | 359.2 | 462.2 | 625.2 | 753.3 | 881.4 | 978.5 | 1081.5 | 1195.5 | 1351.6 | 1368.6 |
| y | 1369.5 | 1222.55 | 1125.5 | 1011.5 | 908.4 | 745.4 | 617.3 | 489.2 | 392.2 | 289.2 | 175.1 |   |

|   | F | P | N | C* | Y | Q | K | P | C | N | R | Total |
|---|---|---|---|---|---|---|---|---|---|---|---|---|
| b | 148.1 | 245.1 | 359.2 | 519.2 | 682.3 | 810.3 | 938.4 | 1035.5 | 1138.5 | 1252.5 | 1408.6 | 1425.6 |
| y | 1426.6 | 1279.6 | 1182.5 | 1068.5 | 908.4 | 745.4 | 617.3 | 489.2 | 392.2 | 289.2 | 175.1 |   |

|   | F | P | N | C | Y | Q | K | P | C* | N | R | Total |
|---|---|---|---|---|---|---|---|---|---|---|---|---|
| b | 148.1 | 245.1 | 359.2 | 462.2 | 625.2 | 753.3 | 881.4 | 978.5 | 1138.5 | 1252.5 | 1408.6 | 1425.6 |
| y | 1426.6 | 1279.6 | 1182.5 | 1068.5 | 965.5 | 802.4 | 674.4 | 546.3 | 449.2 | 289.2 | 175.1 |   |

TABLE 4-continued (SEQ ID NO: 32)

| | F | P | N | C* | Y | Q | K | P | C* | N | R | Total |
|---|---|---|---|---|---|---|---|---|---|---|---|---|
| b | 148.1 | 245.1 | 359.2 | 519.2 | 682.3 | 810.3 | 938.4 | 1035.5 | 1195.5 | 1309.6 | 1465.7 | 1482.7 |
| y | 1483.7 | 1336.6 | 1239.5 | 1125.5 | 965.5 | 802.4 | 674.4 | 546.3 | 449.2 | 289.2 | 175.1 | |

The enzymes used to cleave the proteins into peptides cleave at specific sites (See, e.g., Thiede, B. et al. 2000: Analysis of missed cleavage sites, tryptophan oxidation and N-terminal pyroglutamylation after in-gel tryptic digestion, Rapid Commun. Mass Spectrom., 14:496-502). In some instances, some sites may be missed by the enzyme. In such a case where a cleavage site is missed, the experimental peptide contains a "missed cleavage" site. If two consecutive cleavage sites are missed then a peptide contains two "missed cleavages", etc. See Table 5 for an example.

Table 5 illustrates example of a more advanced rule for modeling trypsin activity. By using a more precise rule the number of unnecessary theoretical peptides may be reduced and therefore a more specific theoretical spectrum may be obtained.

A p-value is the probability to find a match having a score at least as good as the one at hand by chance. A Z-score is a normalized score. Namely, given the mean value of random scores, i.e. scores obtained by matching incorrect peptides, and their standard deviation, the Z-score is the score minus the mean value and divided by the standard deviation. A likelihood ratio is the ratio the probabilities that a match is correct and that a match is not correct (random match).

Peptide scoring is considered in the context of signal detection. The signal to detect is the correct peptide sequence that corresponds to the experimental peptide among a collection of erroneous peptide sequences. An algorithm that uses a scoring system performs the detection. We define as "true positives" (TP), or "hits", the occurrences of the correct peptide sequence found by the algorithm, "false positives" (FP), or "false alarms" or "type I errors", the erroneous peptide sequence occurrences identified as correct by the algorithms, "true negatives" (TN), or "correct rejections", the erroneous peptide sequence occurrences rejected by the algorithm, "false negatives" (FN), or "misses" or "type II errors", the correct peptide sequence occurrences rejected by the algorithm. As used herein, an experimental peptide or experimental peptide sequence "corresponds" to a candidate peptide (such as a peptide sequence in a database) when it has the same identity and order of the amino acid residues in the experimental peptide except only for substitution of amino acids that are mutually isobaric or mutually mass ambiguous within the resolution of the mass spectrometer used to identify the peptide sequence.

TABLE 5

Usual tryptic cleavage rule : trypsin cleaves after every occurrence of K or R except if they are followed by P.
Usual rule for missed cleavage : every cleavage site is considered as a possible missed cleavage site.
Adapted rule (Thiede et al. 2000) : missed cleavages are only possible in the following situations:
1. K or R followed by P
2. K or R followed by K or R
3. K or R preceded by K or R
4. K or R followed by D or E
5. K or R preceded by D or E TABLE 5-continued Example : sequence ATGWRQSTRDASYT (SEQ ID NO: 34)
Usual rule yields peptides : ATGWR (SEQ ID NO: 35), QSTR (SEQ ID NO: 36), DASYT (SEQ ID NO: 37), ATGWRQSTR (1) (SEQ ID NO: 38), QSTRDASYT (1) (SEQ ID NO: 39), ATGWRQSTRDASYT (2) (SEQ ID NO: 34).
Adapted rule yields peptides : ATGWR (SEQ ID NO: 35), QSTR (SEQ ID NO: 36), DASYT (SEQ ID NO: 37), QSTRDASYT(1) (SEQ ID NO: 39).

The peptides with missed cleavages are underlined with the number of missed cleavages (k) in parentheses.

Referring to FIG. 1, there is shown a flow chart illustrating an exemplary method for scoring peptide matches in accordance with one embodiment of the present invention.

The method starts at step 102. At step 104, an experimental peptide and a candidate peptide may be provided. As defined above, the experimental peptide and the candidate peptide may originate from a variety of sources. Data associated with a number of characteristics of the peptides may be provided. For example, mass spectrum information associated with the experimental peptide, the candidate peptide and their respective fragments may be provided, among other things.

The experimental spectrum or spectra to be considered may have been pre-processed before the scoring method is applied. Such pre-processing typically comprises the steps of detecting peaks in the raw spectrum, identifying related isotopic peaks and eventually deconvoluting the spectrum (identifying different charge states of the same ion). The preprocessing step may also comprise a selection of the peaks based on signal to noise ratio and other peak shape characteristics. The pre-processing may yield a mass list or a mass over charge ratio list.

One object of the present invention may be a scoring method aimed at estimating or providing an indication of the correlation between two peptide fragmentation or dissociation spectra. The scoring method may be used in comparing any two MS/MS spectra to determine if the spectra or peptides from which the spectra are derived are related. The method of the invention may also involve comparing an experimental MS/MS spectrum of a peptide with a theoretical MS/MS spectrum computed from a peptide sequence. The scoring system may also be used in comparing a first experimental MS/MS spectrum and a second experimental MS/MS spectrum.

Instead of a single candidate peptide, one or more candidate peptide sequences may be provided. The candidate peptide sequences (e.g. candidates which are theoretical peptides) may be stored in a database. Alternatively, they may be results of a computation, such as a translation of a DNA sequence. Alternatively, candidate peptide sequences may be entered manually. Typically, the candidate peptide sequences are stored in a database. The stored sequences may be amino acid sequences, although any suitable means of representation may be used such that it will also be possible to store nucleotide sequences, which encode amino acid sequences, the amino acid sequences being generated via computer means during the process of correlating to the experimental mass spectrum. Or the library of peptides may result from the in-silico digestion of a library of protein sequences.

In one embodiment the scoring method is used to search a MS/MS run against a peptide sequence library. A MS/MS run is a series of MS/MS spectra for several peptides, typically coming from a protein mixture, and the identification procedure for one experimental peptide is repeatedly applied to each peptide of the run.

At step 106 in FIG. 1, match characteristics may be selected and their probability distributions may be determined. Match characteristics taken into account may include but are not limited to: mass error on the parent peptide, mass errors on the fragments, charge state of the parent, amino acid composition, presence of missed cleavages, elution time, presence of protein modifications, parent peak intensity and signal to noise ratio, fragment peak intensities and signal to noise ratios, signal quality indicators as well as statistics derived from a priori knowledge, e.g. obtainable from a protein database. Considering matches as a tuple of various observations, allows for efficiently dealing with the variable quality of high-throughput data, by fully exploiting the information available.

According to an embodiment of the present invention, the plurality of match characteristics may be treated as random variables each of which has a probability distribution. Statistics describing the distributions of these random variables may be provided by any suitable source, including for example publicly available sources or instrument manufacturers. Statistics may also be obtained empirically or may be estimated, such as for example by using an artificial neural network or Hidden Markov Model (HMM).

At step 108, a suitable stochastic model describing the plurality of match characteristics may be generated. In general, a stochastic model is a mathematical model which contains random (stochastic) components or inputs. Consequently, for any specified input scenario, the corresponding model output variables are known only in terms of probability distributions. In the present invention, a peptide match is defined by the simultaneous observation of different elementary events. By using a stochastic model to describe the observed events as random variables, the invention may generate a score for a match. The user thus selects one or more factors which are to be considered in the model. The model may be a relatively simple model which may take into account only the match characteristics having the greater relative impact on the fragmentation spectrum, or may be a more complex or complete model, which takes into account a greater number of factors observed in the match.

To define these notions and explain how they relate to the present invention, several events are described as variables and introduced as follows. It should be appreciated that given the method of the invention, any suitable combination of events may be selected and modeled, and additional events not listed herein may be used in the model, either alone or in combination with the events described herein. In particular, it is possible to include the results of other peptide identification systems.

$D_p$ is the mass tolerance on the parent peptide mass. It may be expressed in Daltons or in parts per million (ppm). Non-symmetric mass windows may also be considered. In that case $D_p(m_t)$ may be defined as the function that returns a set of real numbers defining the mass window, depending on the peptide theoretical mass $m_t$. Non-symmetric mass windows may be useful for dealing with errors in mono-isotopic peak detection (FIG. 2b). For example, taking the first isotope adds one Dalton to the correct mass and, given an instrument precision $\delta$, one may want to use $D_p(m_t)=[m_t-\delta, m_t+1+\delta]$ or, in case $\delta$ is significantly smaller than 1, $D_p(m_t)=[m_t-\delta, m_t+\delta] \cup [m_t+1+\delta]$. Such non-symmetric sets may be also defined for relative mass errors in ppms.

$D_f$ is the mass tolerance on the fragment masses. It is generally expressed in Daltons or in ppms. Non-symmetric mass windows may also be considered. In that case $D_f$ may be defined as the function that returns a set of real numbers defining the mass window, depending on the fragment theoretical mass. See definition for $D_p$ for examples of non-symmetric sets and the rational behind.

S is the set of ion series considered for a given mass spectrometry instrument.

W is the set of modifications added to the theoretical peptide to match the experimental peptide mass. W is a set of pairs identifying each modification and its position in the peptide sequence, i.e. the amino acid that is modified.

P is a peptide match:

$$P=(m, \text{int}(m), m_t)$$

where m is the experimental parent peptide mass and int(m) the corresponding signal intensity. A match occurs if m is close enough to a theoretical peptide mass $m_t$. Hence a match occurs if $|m-m_t| \leq D_p$, or, in case the tolerance is given in ppm, if $10^6|m-m_t|/(0.5(m+m_t)) \leq D_p$ or, in case of a non-symmetric tolerance, $m \in D_p(m_t)$. As the modifications (W) change the theoretical peptide mass $m_t$, P depends on W and may be written as P(W). The information contained in tuple P may be limited to the experimental mass m, or may be augmented by extra information provided by the signal processing software (peak detection) like peak width, signal to noise, quality of fit with a peptide signal theoretical pattern, etc. Hence a more complete version of P is $$P=(m, \text{int}(m), \text{width}(m), sn(m), \text{fit}(m), m_t).$$

F is a fragment match, i.e. the match restricted to what concerns the fragments. Typically, when a peptide match is observed, the theoretical MS/MS spectrum is computed with possible modifications W included to match the peptide mass. See Baker & Clauser (Baker, P. and Clauser, K. MS-Product, part of the Protein Prospector suite at world wide web address prospector.ucsf.edu/) for theoretical MS/MS spectrum computation. The fragment match is then composed of the experimental fragment masses that are close enough to theoretical fragment masses:

$$F=\{(f_j, \text{int}(f_j), \text{series}(f_j), pos(f_j), m_{t,j})\}, j \in J$$

where J is a set of indices used for indexing the experimental fragment masses $f_j$ that are close enough to a theoretical fragment mass. Assuming that $m_{t,j}$ is the theoretical fragment mass; hence an experimental mass $f_j$ is close enough to a theoretical mass if $|f_j-m_{t,j}| \leq D_f$ or, in case we give the tolerance in ppm, if $10^6|f_j-m_{t,j}|/(0.5(f_j+m_{t,j})) \leq D_f$ or, in case of a non-symmetric tolerance, $f_j \in D_f(m_{t,j})$. The theoretical mass $m_{t,j}$ corresponds to the amino acid at position $pos(f_j)$ in the peptide sequence and ion series $\text{series}(f_j) \in S$. The intensity of the experimental signal $f_j$ is int($f_j$). See Tables 3 and 4 for an example. The theoretical MS/MS spectrum of a peptide depends on the ion series (S) and on the peptide modifications (W), then F is written as F($D_f$, S, W). The information about intensity contained in tuple F may be removed. The information per individual fragment may be augmented by extra information provided by the signal processing software (peak detection) like peak width, signal to noise, quality of fit with a peptide signal theoretical pattern, etc. Hence a more complete version of F is $$F=\{(f_j, \text{int}(f_j), \text{width}(f_j), sn(f_j), \text{fit}(f_j), \text{series}(f_j), \text{pos}(f_j), m_{t,j})\}_{j \in J}$$

z is the charge used to match the experimental peptide m/z ratio with the theoretical peptide mass within distance $D_p$, or in $D_p(m)$ respectively.

t is the elution time of the experimental parent peptide.

k is the number of missed cleavages in the theoretical peptide matching the experimental data.

e is a vector of quantities obtained from other peptide identification systems, e.g. commercial programs such as Sequest and Mascot.

According to embodiments of the invention, Lemma 1 as described below may be used in the scoring method.

Lemma 1. The conditional probability to simultaneously observe events A and B given the event C is equal to the probability to observe the event A given the simultaneous occurrence of the events B and C times the probability to observe the event B given the event C. Namely, in formulae $$P(A,B|C)=P(A|B,C)P(B|C).$$

Proof. We have $P(A,B|C)=P(A,B,C)/P(C)$ and $P(A|B,C)=P(A,B,C)/P(B,C)$. This implies $P(A,B|C)=P(A|B,C)P(B,C)/P(C)$.

The scoring system or method may be used in several contexts. In one example, given the experimental MS/MS spectrum, a peptide sequence s, an ion series set S and the modifications W, a user computes the values of a series of random variables that together constitute what may be defined as an extended match E: $E=(F, P, z, t, k, W, e)$. The user then scores the extended match E by considering every variable in E as a random variable, E is hence itself a random variable, and by computing (i) a probability $P(E|D,s,H_1)$ that the peptide from which the experimental spectrum is obtained corresponds to s; and (ii) the probability $P(E|D,s,H_0)$ that the peptide from which the experimental spectrum is obtained does not correspond to s. D is any extra information available, $H_1$ is the hypothesis that sequence s is the correct sequence of the experimental peptide (alternative hypothesis) and $H_0$ is the null-hypothesis that sequence s is erroneous, i.e. E results from random chance.

To be able to compute the likelihood ratio L, it is necessary to know the distribution of the random variable E, both in case $H_0$ and in case $H_1$. For instance, D can contain the distribution of theoretical peptide masses (FIG. 4) or the distribution of experimentally measured masses. Another possibility is the distribution of the number of modifications with respect to the peptide length.

The advantage of the concept of extended match is that it helps in exploiting the information available in a precise mathematical framework. F is included in E since it is directly related to the MS/MS spectrum. Including P provides the potential to differentiate two theoretical peptides based on their total mass (including modifications) if the matches between theoretical and experimental MS/MS spectra are of similar quality. The number of missed cleavage(s) also has the potential to help discriminating several candidate matches. Generally, the probability that the enzyme misses a cleavage site is significantly inferior to one. Hence, a theoretical peptide containing k>0 missed cleavage(s) has a reduced probability to be correct. The charge state z is strongly correlated to the peptide length since long peptides have a higher probability to gain positive charges or to lose negative charges. Therefore z may be essential to discriminate candidate peptides according to their length. Also, the ion series observed in the experimental spectra strongly depends on the parent peptide charge state. A similar reason motivates the inclusion of t as peptides elute at different times in a HPLC column depending on their hydrophobicity and size. Finally, the set of modifications W added to the peptide may be advantageously considered. An immediate example is when there are a suspect number of modifications (too many). One may typically rely on a statistics of the number of modifications relative to the peptide length to assess the probability that W is plausible.

In one embodiment the scoring method is used to identify an experimental peptide whose MS/MS spectrum is available by searching a library of peptide sequences. The processing is applied to a plurality of sequences in the library and comprises the steps of:
1. Comparing the theoretical peptide mass with the experimental parent peptide mass (referred to as m and $m_t$ respectively); and
2. If the absolute value of the difference of the two masses is smaller or equal to $D_p$, then the theoretical fragmentation spectrum is computed and E and L are computed.

If the absolute value of the difference of the two masses is not smaller or equal to $D_p$, no correlation is assumed.

Referring to Step 2, the condition $|m-m_t| \leq D_p$ may be replaced by $10^6 |m-m_t|/(0.5(m+m_t)) \leq D_p$, in case the tolerance is given in ppms, or, in case of non-symmetric tolerance, $m \in D_p(m_t)$, where m is the experimental peptide mass and $m_t$ the theoretical peptide mass.

In another embodiment the scoring method is used to identify an experimental peptide whose MS/MS spectrum is available by searching a library of peptide sequences. The peptides are possibly modified and some modifications are not directly specified in the peptide library. The processing applied to every peptide sequence in the library comprises the steps of:
1. Given a set of possible modifications, every possible theoretical mass is computed and compared to the experimental mass. Exemplary methods for computing modifications are described in International Patent Application No. PCT/EP03/03998, filed 16 Apr. 2003, describing methods to compute modified peptides, the disclosure of which is incorporated herein by reference. Each possible theoretical mass corresponds to a set of modifications W (possibly empty). W is made of modifications directly specified in the peptide sequence library and other modifications added at the time of total mass computation.
2. In case the absolute value of the difference between the experimental peptide mass and the theoretical mass (for a specific W) is smaller or equal to $D_p$, then the theoretical fragmentation spectrum is computed, considering W, and E and L are computed. Otherwise, no correlation is assumed.

Referring to Step 2, the condition $|m-m_t| \leq D_p$ may be replaced by $10^6 |m-m_t|/(0.5(m+m_t)) \leq D_p$, in case the tolerance is given in ppms, or, in case of a non-symmetric tolerance, $m \in D_p(m_t)$, where m is the experimental peptide mass and $m_t$ the theoretical peptide mass.

Thus, according to the present invention, any one or more characteristics of a peptide may be taken into account in scoring peptides matches. As further described herein, various versions of E may be considered. The variables taken into account in scoring matches may be selected depending on the events considered to have a significant impact on the match probability, and then, using Lemma 1 and simplifying random variable independence assumptions, effective ways of computing L may be obtained.

Several typical models are shown below. These models described below take into account different events or variables, or combinations of events or variables. It should be appreciated that the methods of the invention are not limited to the following examples, and that the method of the invention may be carried out taking into account any of the variables or any combination of variables.

In one example (version 1), the scoring method may consider mass error on the parent peptide, mass error on the fragment match, charge, elution time, missed cleavages, and peptide modifications. In this case, $E=(F, P, z, t, k, W)$ and $L=P(E|D, s, H_1)/P(E|D, s, H_0)$. This is an instance of extended match including several observations that may be extracted from a database match. Based on reasonable simplifying assumptions it is possible to estimate the probabilities in L. For instance Lemma 1 yields $$P(E/D,s,H_{1,0})=P(F|P, z, t, k, W, D, s, H_{1,0})P(P, z, t, k, W|D, s, H_{1,0})$$

where it is assumed that $P(F|P, z, t, k, W, D, s, H_{1,0}) \cong P(F|z, D, s, H_{1,0})$, i.e. it is assumed the fragment match is not dependent of the parent match P, elution time t, number of missed cleavage k and modifications W. While this example makes the simplifying assumption that the fragment match is independent of the modifications, it should be appreciated that in other examples, fragment match dependence on modifications may be considered as certain modifications may change the fragmentation pattern (see, e.g., DeGnore, J. P. and Qin, J. 1998: *Fragmentation of phosphopeptides in an ion trap mass spectrometer*, J. Am. Soc. Mass Spectrom., 9:1175-1188). The right factor of the right-hand term is also simplified with Lemma 1:

$$P(P, z, t, k, W|D, s, H_{1,0})=P(P|z, t, k, W, D, s, H_{1,0}) \times P(z, t, k, W|D, s, H_{1,0}).$$

It is then assumed that $P(P|z, t, k, W, D, s, H_{1,0}) \cong P(P|z, D, s, H_{1,0})$, i.e. the peptide match is not dependent on the elution time, the number of missed cleavage and the modifications. Again, the independence on the modification could be discussed. The dependence on the charge state z makes sense because the instrument measure mass charge ratios instead of masses directly. Therefore, the measurement errors are amplified with charge states higher than one. Lemma 1 is applied once more:

$$P(z, t, k, W|D, s, H_{1,0})=P(z|t, k, W, D, s, H_{1,0})P(t, k, W|D, s, H_{1,0})$$

and simplifying: $P(z|t, k, W, D, s, H_{1,0}) \cong P(z|t, D, s, H_{1,0})$. The dependence on the elution time is retained because the peptides partially elute according to their size and the number of charges a peptide may carry partially depends on its size. Not considering W is again motivated by simplifying purposes since certain modifications may suppress protonation sites, hence influencing the number of possible charges the peptide may carry. Lemma 1 applied on $P(t, k, W|D, s, H_{1,0})$ yields $$P(t, k, W|D, s, H_{1,0})=P(t|k, W, D, s, H_{1,0})=P(k, W|D, s, H_{1,0}).$$

It is assumed that $P(t|k, W, D, s, H_{1,0}) \cong P(t|W, D, s, H_{1,0})$. Finally, the remaining factor is transformed by Lemma 1 into:

$$P(k, W|D, s, H_{1,0})=P(k|W, D, s, H_{1,0})P(W|D, s, H_{1,0})$$

and $P(k|W, D, s, H_{1,0}) \cong P(k|D, s, H_{1,0})$. Thus, by putting everything together:

$$P(E|D,s,H_{1,0}) \cong P(F|z, D, s, H_{1,0})P(P|z, D, s, H_{1,0})P(z|t, D, s, H_1 P(t|W, D, s, H_{1,0})P(k|D, s, H_{1,0})P(W|D, s, H_{1,0}).$$

In another example, the scoring method may consider mass error on the parent peptide, mass error on the fragment match, charge and missed cleavages. In this embodiment (version 2A), $E=(F, P, z, k)$ and $L=P(E|D, s, H_1)/P(E|D, s, H_0)$. Carrying out a procedure as in the preceding example results in $$P(E|D,s,H_{1,0}) \cong P(F|z, D, s, H_{1,0})P(z|D, s, H_{1,0}) \times P(k|D, s, H_{1,0})P(P|D, s, H_{1,0}).$$

In a further example, the scoring method may consider mass error on the parent peptide, mass error on the fragment match and charge. In this embodiment (version 2B), $E=(F, P, z)$ and $L=P(E|D, s, H_1)/P(E|D, s, H_0)$. Carrying out a procedure as in the preceding examples results in $$P(E|D,s,H_{1,0}) \cong P(F|z, D, s, H_{1,0})P(z|D, s, H_{1,0})P(P|D, s, H_{1,0})$$

In yet a further example, the scoring method may be carried out in a simplified format, wherein mass error on the fragment match and charge are considered. In this embodiment (version 3A): $E=(F, z)$ and $L=P(E|D, s, H_1)/P(E|D, s, H_0)$. Carrying out a procedure as in the preceding examples results in $$P(E|D,s,H_{1,0}) \cong P(F|z, D, s, H_{1,0})P(z|D, s, H_{1,0}).$$

This simplified version no longer contains the peptide match P in the extended match tuple E. This implies that peptide masses are only used to compare experimental and theoretical peptides and, as soon as the mass difference is acceptable, the score is computed without using peptide mass precision. See FIG. 3 for a comparison of such a scoring system with Mascot software (See, e.g., Perkins, D. N., Pappin, D. J., Creasy, D. M. and Cottrell, J. S. 1999: *Probability-based protein identification by searching sequence databases using mass spectrometry data*, Electrophoresis, 20(18):3551-3567).

In yet a further simplified format, the method of the invention may be carried out by considering mass error on the fragment match, and mass error on the parent peptide. In this embodiment (version 3B): $E=(F, P)$ and $L=P(E|D, s, H_1)/P(E|D, s, H_0)$. Carrying out a procedure as in the preceding examples results in $$P(E|D,s,H_{1,0}) \cong P(F|D,s,H_{1,0})P(P|D, s, H_{1,0}).$$

Referring back to FIG. 1, at step 110, probability of a "Hit" may be calculated. That is, the probability (or its distribution) that the experimental peptide matches the candidate peptide sequence may be calculated based on the stochastic model generated. In the following examples, the calculation of $P(E|D,s,H_1)$ will be exemplarily explained.

In one embodiment the distribution of random variable E is learnt from a known data set in case $H_1$, i.e. spectra of known peptides and the corresponding matches in a peptide library are used. Various empirical distributions are computed and can then be used to estimate the probabilities associated to the various events taken into account in E. Referring to the first example above (version 1), empirical methods may be applied to learn the required distributions. The instance of the scoring is in that case $$P(E|D,s,H_{1,0}) \cong P(F|z, D, s, H_{1,0})P(P|z, D, s, H_{1,0})P(z|t, D, s, H P(t|W, D, s, H_{1,0})P(k|D, s, H_{1,0})P(W|D, s, H_{1,0}).$$

W(peptide modifications) $P(W|D, s, H_1)$ may be estimated by computing the empirical distribution of the total number of variable modifications per peptide divided by peptide length, or alternatively the number of potential modification sites, i.e. #W/len(s), where len(s) is the length of peptide sequence s and #W the cardinality of W. Accordingly, there is the approximation $$P(W|D, s, H_1) \cong P(\#W/\text{len}(s)|D, H_1).$$

A more precise estimate may be obtained by estimating the probability of the individual modifications contained in the set W. The modifications may be denoted by $$W = \{(mod_i, pos_i)\}, i \in I,$$

where I is a set of indices, $mod_i$ is a specific modification (Table 1) taken from a set of possible modifications and $pos_i$ the corresponding position in the peptide sequence. While each modification is associated to a position, it is possible that the same modification is found at several positions. It may be assumed that each modification occurs independently and thus learn from a data set of correct matches the empirical distribution of the number of occurrences for each modification relative to the peptide length or the number potential modification sites. The set of distinct modifications found in W and num(mod,W), mod ∈ M(W), the number of occurrences of mod in W are denoted by M(W). With the latter notations, a better approximation may be written as $$P(W|D, s, H_1) \cong \prod_{mod \in M(W)} P\left(\frac{num(mod, W)}{len(s)} \middle| D, H_1\right).$$

It should be appreciated, however, that it is also possible to do without the use of empirical statistics relative to peptide length or the number of potential modification sites. Instead, empirical statistics of the number of modifications may be computed.

In other examples, it is possible to score each modification by its probability, which is estimated by an artificial neural network or hidden Markov model (See, e.g., Blom, N. et al. 1999: *Sequence-and structure-based prediction of eukaryotic phosphorylation sites*, J. Mol. Biol., 294:1351-1362, and Hansen, J. E. et al. 1998: *NetOglyc: prediction of mucine type O-glycosylation sites based on sequence context and surface accessibility*, Glycoconjugate Journal, 15:115-130). The individual probabilities may be then multiplied by assuming independence. The artificial neural network or hidden Markov model parameters may be trained from a set of known examples.

Missed cleavages $P(k|D, s, H_1)$ may be estimated from a set of correct identifications by simply computing the empirical probability of missed cleavage (cleavage sites that are not cleaved). Table 5 provides exemplary rules for predicting sites of missed cleavages. Denoting by p this probability and assuming independence of the missed cleavage events, there is the approximation $$P(k|D, s, H_1) \cong \binom{n}{k} p^k (1-p)^{n-k},$$

a binomial distribution, where n is the number of cleavage sites in the peptide sequence.

Elution time (t) $P(t|W, D, s, H_1)$ may be estimated by correlating physico-chemical properties of the peptide, estimated from its sequence, with observed elution times from a set of known peptides. In an HPLC-MS/MS protocol, typical properties are hydrophobicity and peptide size. A natural way to measure the correlation is to learn an empirical distribution of elution time in dependence of hydrophobicity and size. W is considered as modifications have an impact on hydrophobicity and size.

Several authors have described algorithms to estimate elution times based on peptide sequences (See, e.g., Sakamoto, Y., Kawakami, N. and Sasagawa, T. 1988: *Prediction of peptide retention times*, J Chromatogr., 442:69-79, Mant, C. T., Zhou, N. E. and Hodges, R. S. 1989: Correlation of protein retention times in reversed-phase chromatography with polypeptide chain length and hydrophobicity, J. Chromatogr., 476:363-75). It is then possible to learn statistics about the difference between the observed time for the experimental peptide and the time predicted from the candidate theoretical peptide sequence. The statistics may be learned using a test data set for example, and then used to estimate elution times for peptide matches to be scored. Hence $P(t|W, D, s, H_1) \cong P$ ("observed difference"$|D, H_1$).

Charge (z) $P(z|t, D, s, H_1)$ may be estimated by computing the empirical distribution of the charge states in dependence of the peptide length, hence neglecting the elution time. As a matter of fact, the charge state is strongly correlated to the number of sites able to gain or lose a charge on the peptide. This number of sites is itself strongly correlated to the number of amino acids. This yields (see FIG. 7)

$$P(z|t, D, s, H_1) \cong P(z|D, s, H_1) \cong P(z|len(s), D, H_1).$$

Figure 7:
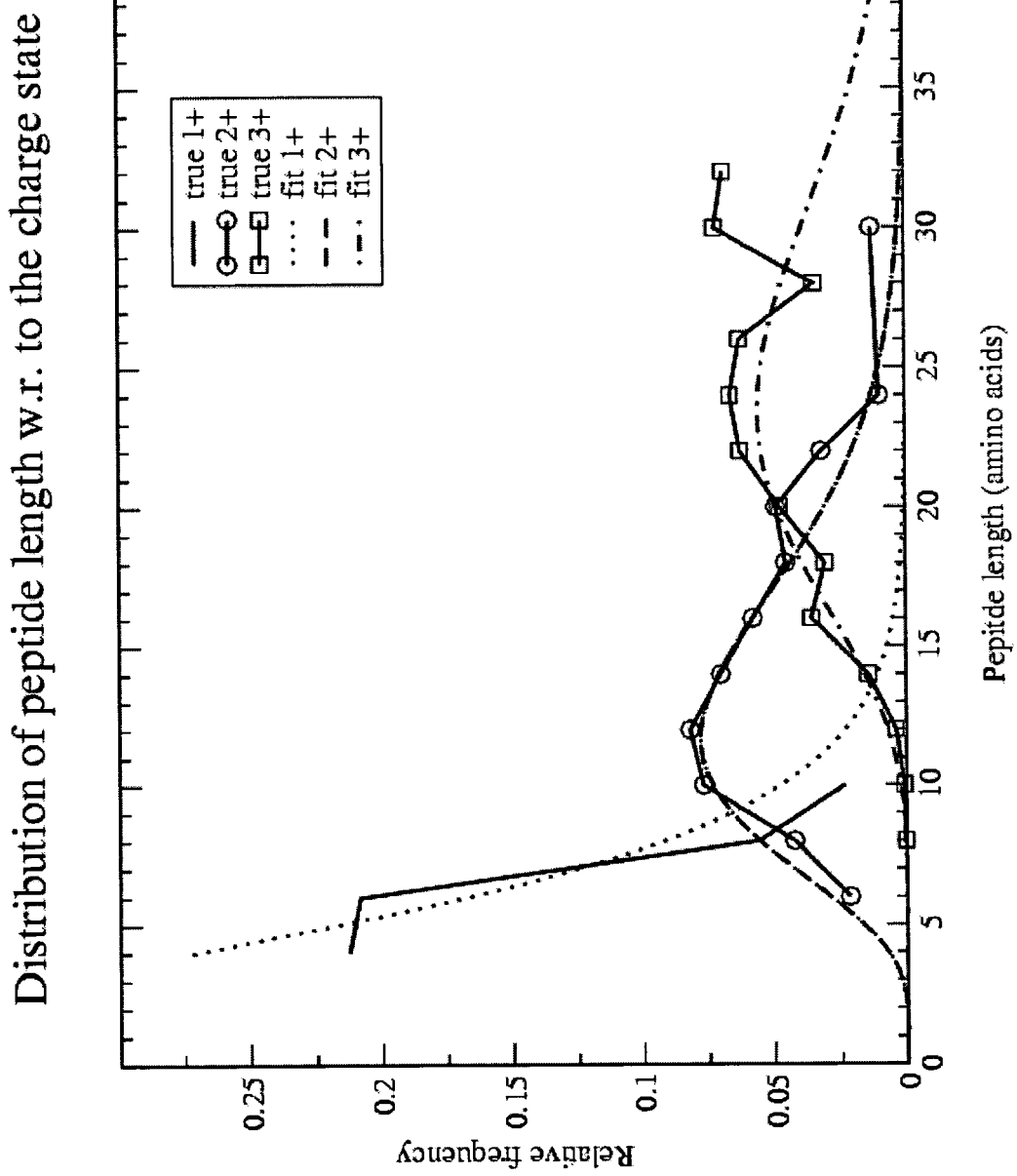
FIG. 7 shows the distribution of relative frequencies of observed charge states with respect to the peptide sequence length, as well as a theoretical model fitting the empirical distributions.

FIG. 7 shows the distribution of relative frequencies of observed charge states with respect to the peptide sequence length, as well as a theoretical model fitting the empirical distributions. This empirical distribution was learnt from a set of 320 singly charged peptides, 2310 doubly charged peptides and 967 triply charged peptides analyzed with a Bruker Esquire ion trap instrument. The distributions have been normalized according to the frequencies of peptides of a given size in a reference library (SWISS-PROT in this case).

In another aspect of the present invention, the empirical distribution of the charge states may be computed in dependence of the elution time, as it depends on the peptide size, and the peptide length:

$$P(z|t, D, s, H_1) \cong P(z|t, len(s), D, H_1).$$

Peptide match (P) $P(P|z, D, s, H_1)$ may be estimated by many approximations of various precision and sophistication. In one aspect of the present invention, computing P involves considering only the experimental mass over charge ratio. Assuming a Gaussian (normal) distribution of the errors and $D_p$ given in Daltons, then $$P(P|z, D, s, H_1) \cong \frac{1}{\sqrt{2\pi} \, \sigma(z)} \exp\left(-\frac{(m - m_t)^2}{2\sigma^2(z)}\right),$$

where $m_t$ is the theoretical mass and $\sigma(z)$ the standard deviation, modelling the instrument precision. Note the dependence of the standard deviation on the peptide charge state because the mass tolerance is in Dalton. In case $D_p$ is given in ppms, $\sigma$ may be assumed to be independent of the charge state.

In the definition of $D_p$, a possible non-symmetric case especially designed for dealing with errors in mono-isotopic peak detection is considered. In particular, it is possible that peak detection software selects the first isotope ($C^{14}$ peak) as the mono-isotopic peak ($C^{13}$ peak). While the above-described normal estimations may be used in such a case, the invention further provides using a bimodal theoretical distribution which may be computed as follows:

$$P(P|z, D, s, H_1) \cong$$

$$\frac{1}{\sqrt{2\pi}\,\sigma(z)}\left((1-p)\exp\left(-\frac{(m-m_t)^2}{2\sigma^2(z)}\right) + p\exp\left(-\frac{(m-m_t-1)^2}{2\sigma^2(z)}\right)\right),$$

where p is the probability of erroneously choosing the first isotope. As disclosed herein, σ may be considered constant if the error tolerance is in ppms.

It will also be appreciated that further information contained in P may be taken into account. For instance, it is known that certain amino acids favor peptide detection (See, e.g., Papayannopoulos, I. A. 1995: *The interpretation of collision-induced dissociation mass spectra of peptides*, Mass Spectrometry Review, 14:49-73, Van Dongen, W. D. et al. 1996: *Statistical analysis of mass spectral data obtained from singly protonated peptides under high-energy collision-induced dissociation conditions*, J. Mass Spectrom., 31:1156-1162). Therefore the probability to detect a peptide may be adjusted depending on peptide composition:

$$P(P|z, D, s, H_1) \cong P(\text{``signal''}|D, s, H_1) \frac{1}{\sqrt{2\pi}\,\sigma(z)} \exp\left(-\frac{(m-m_t)^2}{2\sigma^2(z)}\right),$$

where the distribution for computing P("signal"|D, s, $H_1$) is learnt empirically from a set of known peptides.

Figure 4:
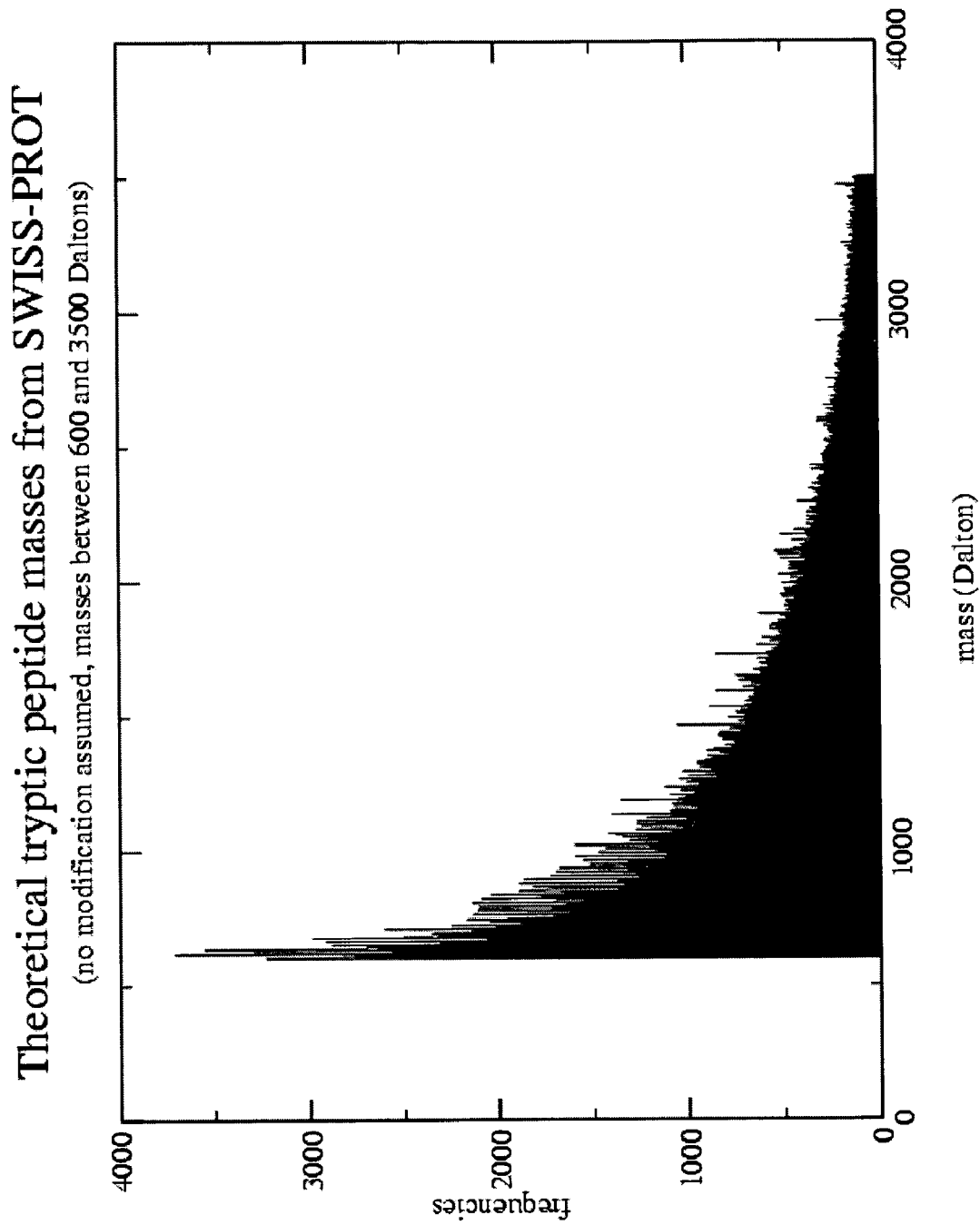
FIG. 4 shows theoretical tryptic peptide mass distribution from the SWISS-PROT database for a candidate peptide, which distribution may be used to score peptide matches: high peptide masses are statistically more significant compared to low peptide masses.
Figure 5A:
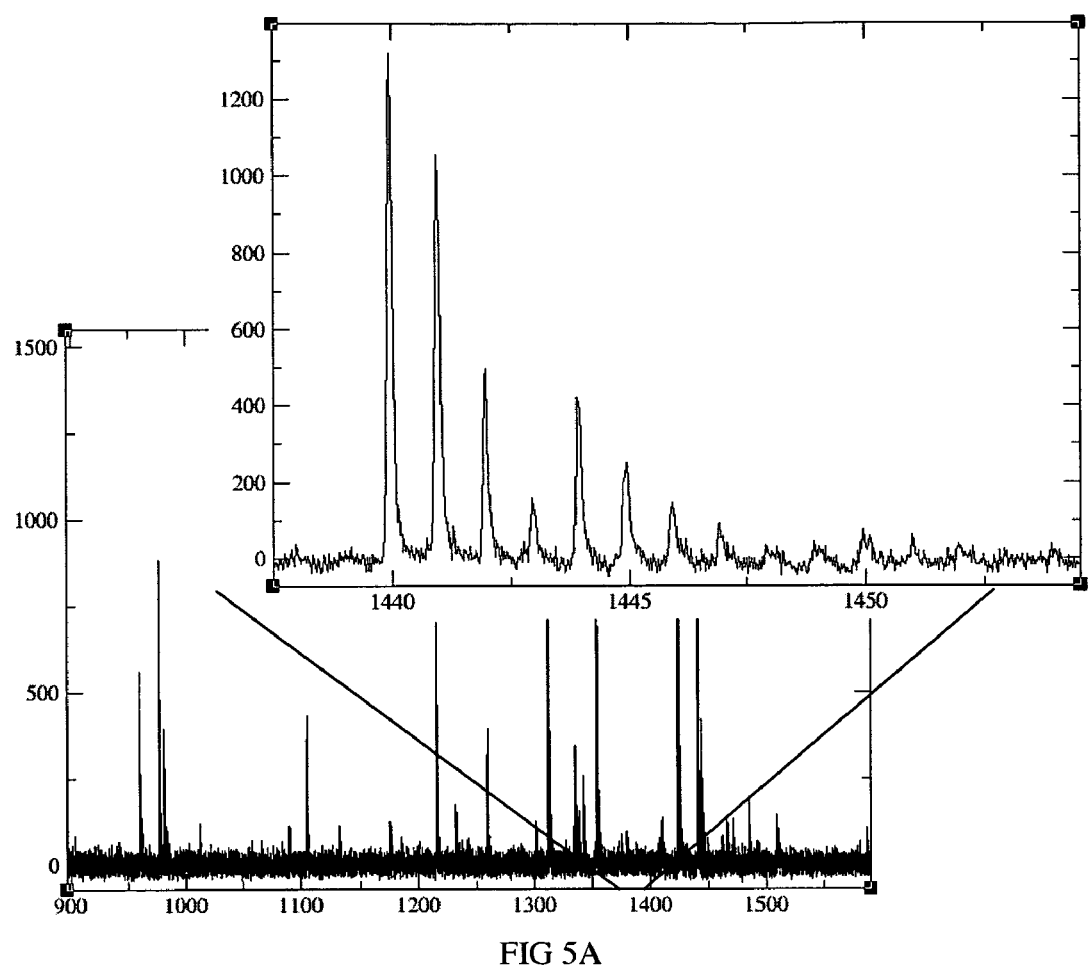
Figure 5B:
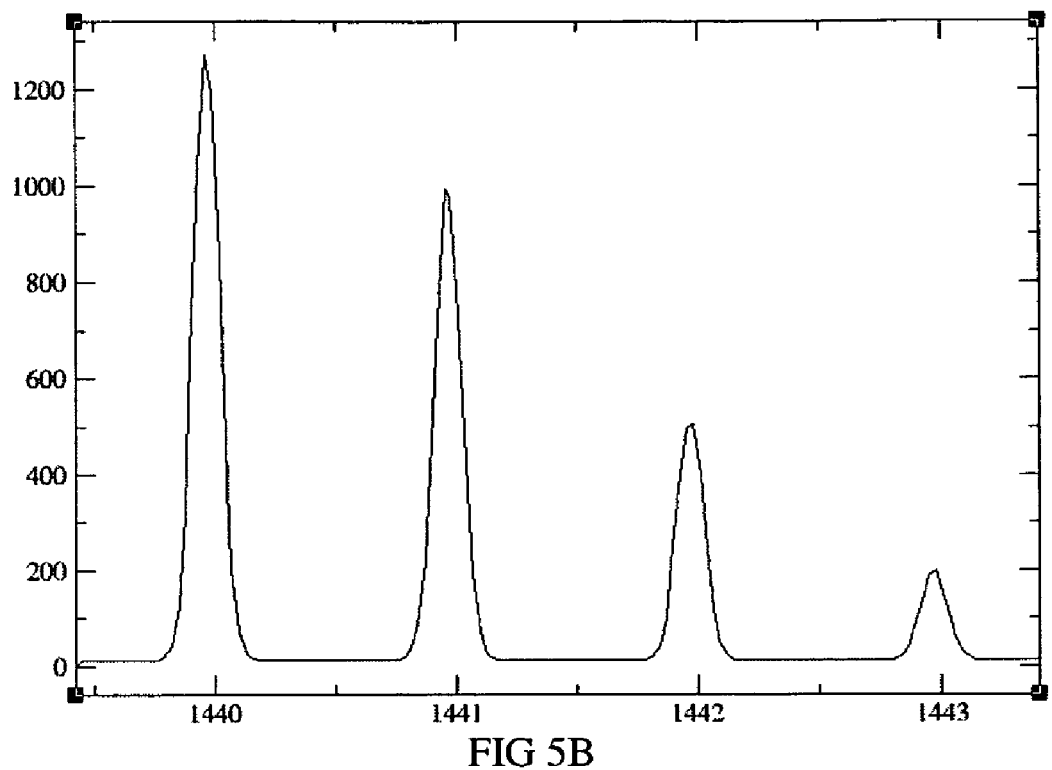
FIG. 5B shows an example of a peptide theoretical isotopic distribution.

In other aspects of the invention, the probability P(P|z, D, s, $H_1$) estimation may include knowledge of the distribution of peptide theoretical masses (FIG. 4). The purpose of this estimation is to reduce the significance of matches involving peptides having a very frequent mass (low mass). As peptides with high mass are much less frequent, such a match may be regarded as more significant. Typical estimation involving peptide mass distribution takes the form:

$$P(P|z, D, s, H_1) \cong$$

$$P(\text{``significance of } m_t\text{''}|D, H_1) \frac{1}{\sqrt{2\pi}\,\sigma(z)} \exp\left(-\frac{(m-m_t)^2}{2\sigma^2(z)}\right),$$

where P("significance of $m_t$"|D, $H_1$) is empirically estimated from the distribution of FIG. 4.

In other aspects of the present invention, the probability P("significance of $m_t$"|D, $H_1$) is estimated by fitting a curve to the empirical distribution of FIG. 4. Typically, a curve like $\beta e^{-\alpha(m_1-m_0)}$ may be used, where $m_0$ is the lower bound of the mass range considered.

In other aspects of the present invention, the probability P(P|z, D, s, $H_1$) may be estimated by considering signal intensity, denoted int(m), and/or quality (signal/noise ratio sn(m), quality of the signal fit(m)). It should be appreciated that signal intensity may require some normalisation like taking its logarithm, expressing it in percentage of the most intense signal detected or taking some power of its value (($int^r(m)$, r a real number).

In other aspects of the invention, supplementary criteria are considered in scoring a match, such that mass tolerance $D_p$ is not the only criterion considered. Supplementary criteria may be for example signal to noise ratio, elution time, signal quality or signal intensity.

Furthermore, other external criteria may be applied to select peptides. In one example, taxonomy is considered in selecting peptides. In one other aspect of the invention, peptides are selected based on the iso-electric point (pI) and/or molecular weight (MW) of the protein they come from. In other more general aspects, criteria based on protein properties and/or peptide properties may be taken into account in scoring matches, i.e. hydrophobicity, electric charge, etc.

Fragment match (F) P(F|z, D, s, $H_1$) plays an important role in the present methods of scoring peptides matches; disclosed herein are therefore several techniques that may be used to estimate its value. A first and simple technique is to empirically learn the probabilities of detecting each ion series. Namely, based on a set of known peptides whose MS/MS spectra have been acquired, the theoretical spectra is computed and, given $D_f$, the experimental fragments are detected. By assuming the independence of the ion series and the independence on the fragment sequence, it is straightforward to estimate the probabilities of each series. For [∈S, the corresponding probability may be denoted by $q_v(z)$. Note the probabilities are determined depending on the parent charge state. The parent charge state may strongly influence the generation of certain ion series. Moreover, certain series are impossible at certain charge states (doubly charged y++ for a singly charged peptide). The probabilities to match fragments in each series are then determined by random chance by taking random peptide sequences whose MS/MS theoretical spectra are not related to the data. The random match probabilities are denoted $r_v(z)$. Thus, the probability to observe a match is then $p_v(z) = q_v(z) + (1-q_v(z))r_v(z)$. Therefore $$P(F|z, D, s, H_1) \cong \prod_{j \in J} p_{series(f_j)} \prod_{i \in I-J} (1 - p_{series(i)}(z)), \quad \text{(F1)}$$

where I is the set of indices corresponding to every theoretical fragment mass and I-J is the set of unmatched theoretical masses. Note there is no attempt to model the unmatched experimental masses. Noise is voluntarily not modelled in the experimental data, as its origin is complex and diverse. Thus, while the skilled person will appreciate that noise may be considered as well, taking into account noise may be avoided.

It is another aspect of the present invention to model fragment match probabilities by normal distributions. The preceding model considers fragment matches either completely or not at all; that is, as soon as an experimental mass is close enough to an experiment mass, it is considered. This is analogous to considering a uniform distribution. A plot of experimental fragment mass errors strongly suggests a bell-shaped distribution. This yields $$P(F|z, D, s, H_1) \cong$$

$$\prod_{j \in J} p_{series(f_j)}(z) \frac{1}{\sqrt{2\pi}\,\sigma(z)} \exp\left(-\frac{(f_j - m_{t,j})^2}{2\sigma^2(z)}\right) \prod_{i \in I-J} (1 - p_{series(i)}(z)),$$

where the factor $(1-P_{series(i)}(z))$ may be multiplied by a factor equal to the average of $$\frac{1}{\sqrt{2\pi}\;\sigma(z)}\exp\!\left(-\frac{(f_j - m_{t,j})^2}{2\sigma^2(z)}\right)$$

in order not to favour the unmatched fragments.

It is also possible to make the fragment match probabilities dependent on the amino acid composition of the fragments. In particular, it is known that the last amino acid of a fragment plays a special role in the fragmentation process (See, e.g., Tabb, D. L., Smith, L. L., Breci, L. A., Wysocki, W. H., Lin, D. and Yates, J. R. 2003: *Statistical characterization of ion trap tandem mass spectra from doubly charged tryptic peptides*, Anal. Chem., 75:1155-1163). Therefore, it is possible to introduce new parameters by replacing $p_{series(i)}(z)$ with $p_{series(i),(pos(i))}(z)$, where a(pos(i)) returns the amino acid at position pos(i), i.e. the position of the last amino acid of the fragment number i.

In a further aspect, it is possible to group amino acids by classes of amino acids with similar role on the fragmentation process and hence replace a(pos(i)) by class(pos(i)). This has the advantage of reducing the number of parameters in the model. See Table 6 for an example. Table 6 illustrates a parameter set of one scoring system that uses fragment match probabilities by amino acid class, fragment intensity and consecutive fragment matches. The parameters have been learnt on a data set of 6800 doubly and triply charged peptides analysed by Esquire 3000+ ion trap spectrometers (alternative model). The random match probabilities (null model) were obtained by generating 100 random peptides for each of the 6800 reference peptides. The random peptides have a mass close to the correct peptide but a random sequence, which is generated by an order 3 Markov chain.

TABLE 6

FRAGMENT PROBABILITIES PER AA CLASS oneAAClass aa= "AFHILMVWY" (SEQ ID NO: 40) charge= "2" nTerm= "yes"
oneAAClass aa= "CDEGNQST" (SEQ ID NO: 41) charge= "2" nTerm= "yes"
oneAAClass aa= "KPR" charge= "2" nTerm= "yes"
oneAAClass aa= "HP" charge= "2" nTerm= "no"
oneAAClass aa= "ACFIMDEGLNQSTVWY" (SEQ ID NO: 42) charge= "2" nTerm= "no"
oneAAClass aa= "KR" charge= "2" nTerm= "no"
fragType= "a" aaClass= "AFHILMVWY" (SEQ ID NO: 40) foundProb= "0.174985" notFoundProb= "0.0796809"
fragType= "a-NH3" aaClass= "AFHILMVWY" (SEQ ID NO: 40) foundProb= "0.184976" notFoundProb= "0.0891291"
fragType= "b" aaClass= "AFHILMVWY" (SEQ ID NO: 40) foundProb= "0.572251" notFoundProb= "0.0924224"
fragType= "b" aaClass= "CDEGNQST" (SEQ ID NO: 41) foundProb= "0.464668" notFoundProb= "0.0918588"
fragType= "b" aaClass= "KPR" foundProb= "0.315322" notFoundProb= "0.198784"
fragType= "b-H2O" aaClass= "AFHILMVWY" (SEQ ID NO: 40) foundProb= "0.556841" notFoundProb= "0.099369"
fragType= "b-H2O" aaClass= "CDEGNQST" (SEQ ID NO: 41) foundProb= "0.413524" notFoundProb= "0.0908845"
fragType= "b-H2O" aaClass= "KPR" foundProb= "0.191116" notFoundProb= "0.123449"
fragType= "b-NH3" aaClass= "AFHILMVWY" (SEQ ID NO: 40) foundProb= "0.342007" notFoundProb= "0.0960211"
fragType= "b-NH3" aaClass= "CDEGNQST" (SEQ ID NO: 41) foundProb= "0.300601" notFoundProb= "0.0914023"
fragType= "y" aaClass= "HP" foundProb= "0.72187" notFoundProb= "0.0758288"
fragType= "y" aaClass= "ACFIMDEGLNQSTVWY" (SEQ ID NO: 42) foundProb= "0.654344" notFoundProb= "0.074072"
fragType= "y++" aaClass= "HP" foundProb= "0.136688" notFoundProb= "0.0504078"
fragType= "y++-H2O" aaClass= "HP" foundProb= "0.152157" notFoundProb= "0.0763926"
fragType= "y++-H2O" aaClass= "KR" foundProb= "0.219081" notFoundProb= "0.0591648"
fragType= "y++-NH3" aaClass= "HP" foundProb= "0.162445" notFoundProb= "0.0613693"
fragType= "y-H2O" aaClass= "HP" foundProb= "0.492051" notFoundProb= "0.095759"
fragType= "y-H2O" aaClass= "ACFIMDEGLNQSTVWY" (SEQ ID NO: 42) foundProb= "0.382798" notFoundProb= "0.11102"
fragType= "y-H2O" aaClass= "KR" foundProb= "0.261484" notFoundProb= "0.0935407"
fragType= "y-NH3" aaClass= "HP" foundProb= "0.227974" notFoundProb= "0.0803569"
fragType= "y-NH3" aaClass= "ACFIMDEGLNQSTVWY" (SEQ ID NO: 42) foundProb= "0.229808" notFoundProb= "0.079139"
INTENSITY (5 bins, based on the rank, random probability is 0.2)

fragType= "b" matchProb= "0.0668139 0.0796404 0.113967 0.193713 0.546128"
fragType= "b++" matchProb= "0.11316 0.122381 0.135792 0.198659 0.432104"
fragType= "b-NH3" matchProb= "0.127768 0.141787 0.165525 0.246296 0.31942"
fragType= "b-H2O" matchProb= "0.0952763 0.106863 0.140196 0.240998 0.417112"
fragType= "y" matchProb= "0.0323419 0.0365731 0.0575199 0.108714 0.765061"
fragType= "y++" matchProb= "0.103134 0.127551 0.152697 0.216837 0.401603"
fragType= "y-NH3" matchProb= "0.151402 0.163136 0.189537 0.24837 0.24837"
fragType= "y-H2O" matchProb= "0.104856 0.109809 0.139647 0.210921 0.435371"
CONSECUTIVE FRAGMENT MATCHES name= "hmmJ, alternative : (+), b, b-H2O, b-NH3" order= "2"
States:

oneState name= "S"
oneState name= "S1"
oneState name= "S2"
Emissions:

oneEmission name= "s"
oneEmission name= "m"
oneEmission name= "f"
Links:

oneLink from= "S" to= "S1" prob= "1"
oneLink from= "S1" to= "S1" prob= "0.642728"
oneLink from= "S1" to= "S2" prob= "0.357272"
oneLink from= "S2" to= "S1" prob= "0.0666977"
oneLink from= "S2" to= "S2" prob= "0.933302"
Emits:

oneEmit state= "S" emit= "s" prob= "1"
oneEmit state= "S1" emit= "m" prob= "0.00347297"
oneEmit state= "S1" emit= "f" prob= "0.996527"
oneEmit state= "S2" emit= "m" prob= "0.854912"
oneEmit state= "S2" emit= "f" prob= "0.145088"
name= "hmmJ, null : (+), b, b-H2O, b-NH3" order= "2"
States:

oneState name= "S"
oneState name= "S1"
oneState name= "S2"
Emissions:

oneEmission name= "s"
oneEmission name= "m"
oneEmission name= "f"
Links:

oneLink from= "S" to= "S1" prob= "1"
oneLink from= "S1" to= "S1" prob= "0.775506"
oneLink from= "S1" to= "S2" prob= "0.224494"

TABLE 6-continued

```
oneLink from="S2" to="S1" prob="0.0477655"
oneLink from="S2" to="S2" prob="0.952234"
Emits:

oneEmit state="S" emit="s" prob="1"
oneEmit state="S1" emit="m" prob="0.00110366"
oneEmit state="S1" emit="f" prob="0.998896"
oneEmit state="S2" emit="m" prob="0.3068"
oneEmit state="S2" emit="f" prob="0.6932"
name="hmmJ, alternative : (-), y, y-H2O, y-NH3" order="2"
States:

oneState name="S"
oneState name="S1"
oneState name="S2"
Emissions:

oneEmission name="s"
oneEmission name="m"
oneEmission name="f"
Links:

oneLink from="S" to="S1" prob="1"
oneLink from="S1" to="S1" prob="0.591697"
oneLink from="S1" to="S2" prob="0.408303"
oneLink from="S2" to="S1" prob="0.124842"
oneLink from="S2" to="S2" prob="0.875158"
Emits:

oneEmit state="S" emit="s" prob="1"
oneEmit state="S1" emit="m" prob="0.0463787"
oneEmit state="S1" emit="f" prob="0.953621"
oneEmit state="S2" emit="m" prob="0.968159"
oneEmit state="S2" emit="f" prob="0.0318407"
name="hmmJ, null : (-), y, y-H2O, y-NH3" order="2"
States:

oneState name="S"
oneState name="S1"
oneState name="S2"
Emissions:

oneEmission name="s"
oneEmission name="m"
oneEmission name="f"
Links:

oneLink from="S" to="S1" prob="1"
oneLink from="S1" to="S1" prob="0.770504"
oneLink from="S1" to="S2" prob="0.229496"
oneLink from="S2" to="S1" prob="0.136185"
oneLink from="S2" to="S2" prob="0.863815"
Emits:

oneEmit state="S" emit="s" prob="1"
oneEmit state="S1" emit="m" prob="0.0202632"
oneEmit state="S1" emit="f" prob="0.979737"
oneEmit state="S2" emit="m" prob="0.31142"
oneEmit state="S2" emit="f" prob="0.68858"
```

Figure 8:
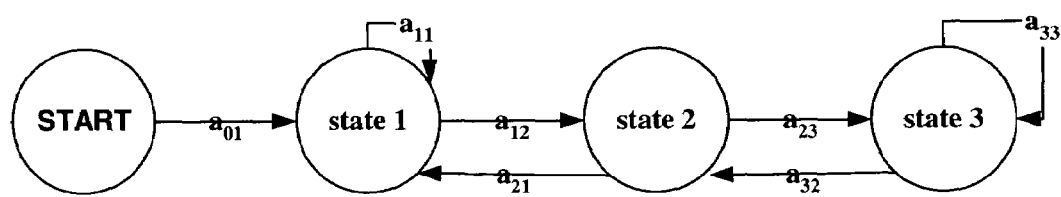
FIG. 8 is an illustration of an order 3 model of an ion series match in accordance with an embodiment of the present invention.
Figure 10:
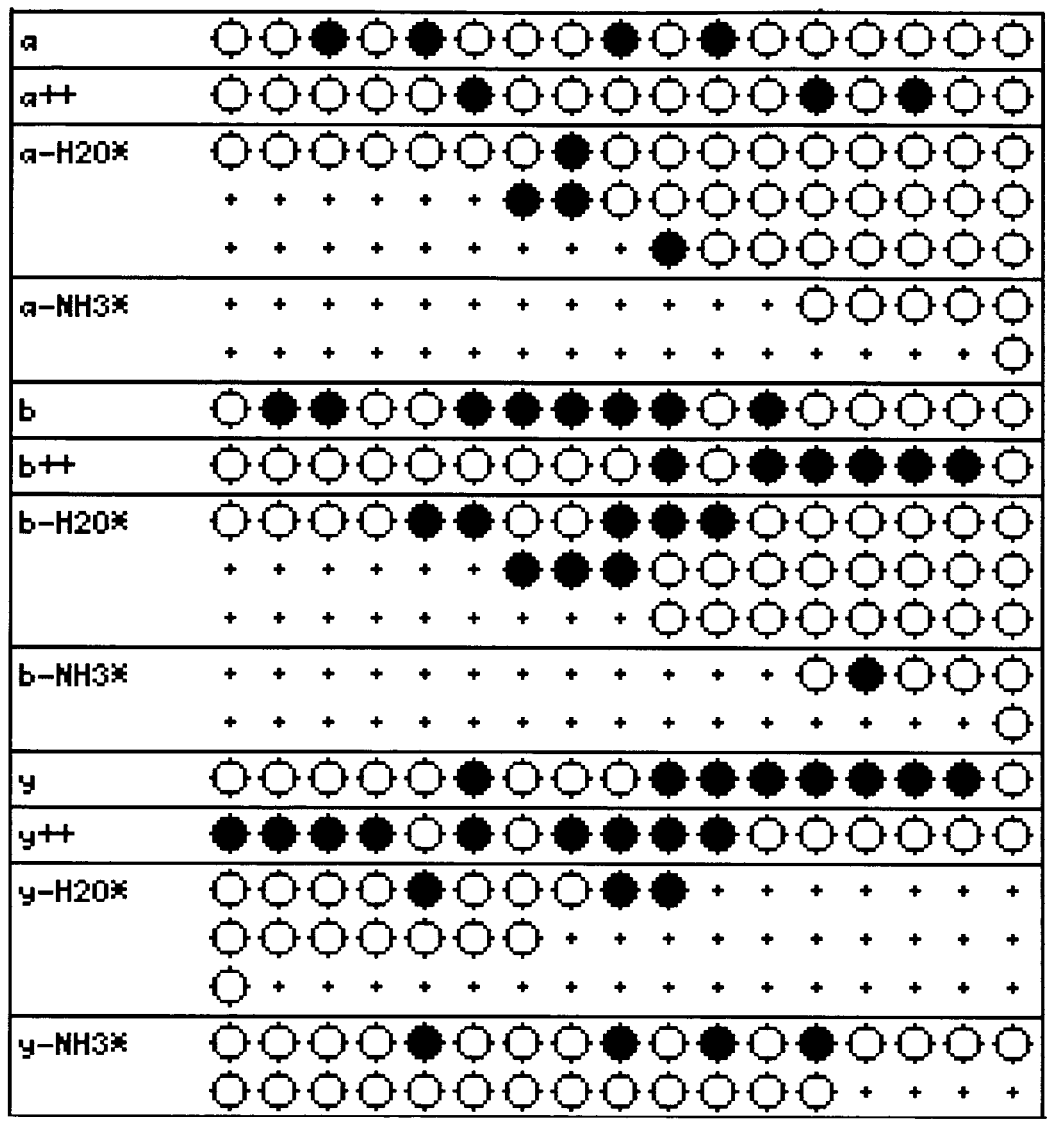
FIG. 10 illustrates a fragment match in accordance with an embodiment of the present invention.

In another aspect, the present invention considers yet further models for considering series of successive matches. In the case of a correct match, it is expected that one observes consecutive fragment matches in a given ion series. Thus, in an embodiment, the scoring system computes a higher probability of a correct match, e.g. better score, with greater numbers of successive matches. An example is shown in FIG. 10, where circles represent amino acids in a peptide, and several successive fragment matches (indicated in filled circles) are detected. This observation may be used to better differentiate false positives from true positives and it allows a user to relax other simplifying hypotheses in the model that every fragment match is independent from the others, and still retain accuracy. The reason consecutive fragment matches are observed in correctly matched spectra is that once a fragment contains a protonation site, both this fragment and other longer fragments that contain the shorter fragment are detected since the longer fragments also contain the protonation site. A natural model for identifying such patterns is a Hidden Markov Model (HMM) (See, e.g., Ewens, W. J. and Grant, G. R. 2001: *Statistical Methods in Bioinformatics*, Springer, N.Y., and Durbin, R. et al. 1998: *Biological sequence analysis*, Cambridge University Press, Cambridge). The HMM can have several states corresponding to fragment matches following 0, 1, 2, . . . , n previous fragment matches in a given series. Independence of the series is assumed and the model of FIG. 8 is used to estimate the probability $P(v|z, D, s, H_1), v \in S$, i.e. the probability $P(F|z, D, s, H_1)$ restricted to one ion series. FIG. 8 is an illustration of an order 3 model of an ion series match in accordance with an embodiment of the present invention. The $a_{ij}$ are the transition probabilities. Each state k has emission probabilities $e_k$. This model only emits two symbols: match and mismatch. See Durbin et al. (Durbin, R. et al. 1998: *Biological sequence analysis*, Cambridge University Press, Cambridge) for more details about graphical representations of HMMs. The parameters of the order 3 HMM of FIG. 8 may be learnt by using a classical procedure like maximum likelihood or expectation maximization (See, e.g., Baum-Velch algorithm, see Durbin et al. 1998). The following approximation is then obtained:

$$P(F|z, D, s, H_1) \cong \prod_{\vartheta \in S} P(\vartheta|z, D, s, H_1).$$

As an example of a maximum likelihood like the parameter set for the model of FIG. 8, the following may be used. From a known data set, estimate the probabilities $P(1_k)$ to observe a match after k−1 previous matches. Similarly, estimate the probabilities $P(0_k)$ to observe a mismatch after k−1 previous matches. By generating random peptide sequences it is also possible to estimate the probabilities $P(r_k)$ to observe a match after k−1 previous matches by chance only. The emission probabilities of state k in the model of FIG. 8 are then set according to $e_k("match")=P(1_k)$ and $e_k("mismatch")=P(0_k)$. The transition probabilities are set according to $a_{k,k+1}=P(1_k)-P(r_k)$, k=1,2, $a_{33}=P(1_3)-P(r_3)$, $a_{11}=1-a_{12}$, $a_{21}=1-a_{23}$, $a_{32}=1-a_{23}$.

Previous models such as those described in Dancik et al (See, e.g., Dancik, V., Addona, T. A., Clauser, K. R., Vath, J. E. and Pevzner, P. A. 1999: *De novo peptide sequencing via tandem mass spectrometry*, J. Comp. Biol., 6:327-342) and Bafna et al (See, e.g., Bafna, V. and Edwards, N. 2001: *SCOPE: a probabilistic model for scoring tandem mass spectra against a peptide database*, Bioinformatics, 17:S13-S21) assume independence of the ion series, which is a rough approximation. By staying with simple HHMs it is possible, for instance, to define generalized series and to apply the model on such series. A possibility is to define a generalized series B that is matched as soon as a match is observed in any series b, b++, b-H2O, b++-H$_2$O, b-NH3, b++-NH3. Similarly, series A and Y may be defined. Such a projection onto generalized series does not fully model the dependence between events like observing a given fragment both in series b and b-NH3, for example, but is more precise than assuming that every fragment in every series is independent.

Another related idea is to use a model with the topology of the HMM of FIG. 8 and to have each state emitting 8 possible symbols: no match, only b or b++, only b-H$_2$O or b++-H2O, only b-NH3 or b++-NH3, (b or b++) and (b-H$_2$O or b++-H$_2$O), (b or b++) and (b-NH3 or b++-NH3), (b-NH3 or b++-

NH3) and (b-H$_2$O or b++-H$_2$O), (b or b++) and (b-NH3 or b++-NH3) and (b-H$_2$O or b++-H$_2$O).

Many other sorts of combination of different ion series may be used to model the dependences they may have between themselves.

A further observation that may be used for improving the estimation of P(F|z, D, s, H$_1$) in other aspects of the invention is illustrated in FIG. 10. FIG. 10 illustrates a fragment match, where one observes the consecutive matches in series b and the b++ series ions. It can be seen that with the increasing size of the peptide, the ion switch from b to b++ series reflecting a change in number of times the ion is charged. The same observation is made for y and then y++. The spots represent amino acids, and the filled spots represent observed ions falling within a mass tolerance range. It is common that a series of consecutive fragment matches are observed in a singly charged ion series, which is then followed by a series of matches observed in the corresponding doubly charged series. Such a pattern typically occurs for triply charged parent peptides. It may also be observed for doubly charged peptides, although less frequently than for triply charged peptides. The explanation is straightforward: as the fragments get longer, they include a second protonation site and hence are no longer detected in the singly charged series but in the doubly charged one.

Another important characteristic or type of information that may be extracted from a MS/MS spectrum, depending on the instrument, is a partial indication about peptide composition. Accordingly, it is a further aspect of the present invention to make use of Immonium ions to infer peptide composition. Immonium ions are the product of the fragmentation of fragments, resulting in ions that contain one residue only. In fact, Immonium ions are used to correlate theoretical peptide composition (obtained from the sequence s) with experimental peaks corresponding to Immonium ions. As described above, empirical probabilities of Immonium ion detection for each residue may be learnt from a set of known spectra. See Falick, A. M. et al. 1993: *Low-mass ions produced from peptides by high-energy collision-induced dissociation in tandem mass spectrometry*, J. Am. Soc. Mass Spectrom., 4:882-893, for such an empirical study.

In other aspects of the present invention, the probability P(F|z, D, s, H$_1$) may be estimated by considering signal intensity, denoted int(f$_j$), and/or quality (signal/noise ratio sn(f$_j$), quality of the signal fit(f$_j$)). It is appreciated that signal intensity may require some normalisation like taking its logarithm, expressing it in percentage of the most intense signal detected, taking its rank in the peak list intensities or taking some power of its value ((int$^r$(f$_j$), r a real number).

In other aspects of the present invention, supplementary criteria are added to consider a fragment match. Namely, the mass tolerance D$_f$ is not the only criterion. Supplementary criteria may be signal to noise ratio, signal quality or intensity.

In one embodiment a specific processing is applied in case of several experimental masses are within D$_f$ tolerance of a theoretical mass. It is one aspect of the present invention to consider the closest experimental mass only. It is another aspect of the invention to take the average of the retained experimental masses.

Referring back to FIG. 1, at step 112, probability of a "Miss" may be calculated. That is, the probability (or its distribution) that the experimental peptide does not match the candidate peptide may be calculated based on the stochastic model generated. In the following examples, the calculation of P(E|D,s,H$_0$) will be exemplarily explained.

One technique to estimate the probabilities above under the null-hypothesis condition H$_0$ is to use experimental spectra of known peptides for searching a library that does not contain the known peptides, thus ensuring no possible correct match. Such searches allow for empirically learning the various random distributions needed for the null model.

In one embodiment the peptide library is any peptide library from which the peptide sequences corresponding to the experimental mass spectra are removed. The remainder of the library is used for learning the distributions.

In one embodiment the peptide library is a library of random peptides generated from an appropriate stochastic model. The stochastic model may be learned from a library of existing peptides.

In one embodiment the stochastic model is a Markov chain of order n (See, e.g., Durbin et al. 1998) designed for modeling protein sequences containing an end-state to model sequence length. The random protein sequences are cleaved according to the enzyme used for experimental protein digestion (see Table 5).

P(W|D, s, H$_0$) may be estimated by learning an empirical distribution. In one aspect of the invention, this task is performed according to the steps of:
1. providing or obtaining a set of experimental MS/MS spectra for one or more peptides whose identity is known;
2. providing or generating a library of random peptides, and further determining that the peptides in the experimental set are not present in the database by chance;
3. comparing and matching each random peptide to each experimental MS/MS spectrum, allowing for the presence of modifications (W); and
4. selecting and keeping the best matche(s) for each experimental spectrum, and counting the number of modifications included, i.e. empirically learn #W/len(s).

The approximation is then P(W|D, s, H$_0$)≅P(#W/len(s)|D, H$_0$).

A separate distribution for each distinct modification can then be learned using the same methods as described hereinabove for hypothesis H$_1$.

P(k|D, s, H$_0$) may be estimated along the same lines used to estimate P(W|D, s, H$_0$) above: random matches from a random library of peptides are obtained, and the probability that a cleavage site is missed is estimated. Then the same binomial as for P(k|D, s, H$_1$) may be used.

P(t|W, D, s, H$_0$) may be estimated by assuming a uniform distribution for random elution time, i.e. P(t|W, D, s, H$_0$)≅1/T, where T is the acquisition window duration.

P(z|t, D, s, H$_0$) may be estimated according to $P(z|t, D, s, H_0) \cong P(z|D, s, H_0) \cong P(\text{"find charge state } z \text{ in experimental data"}).$ Another possibility is $P(z|t, D, s, H_0) \cong P(\text{"find charge state } z \text{ in experimental data detected at time t"}).$ Finally, it is also possible to proceed in a method similar to that used for estimating P(W|D, s, H$_0$) above: random matches from a random library of peptides are obtained, and the following formula is used $P(z|t, D, s, H_0) \cong P(z|D, s, H_0) \cong P(\text{"charge state } z \text{ used to match random peptide with experimental data"}).$ P(P|z, D, s, H$_0$) may be estimated by a different approach. In one embodiment of the scoring system it is assumed that D$_p$ is to be given in Daltons. From a set of experimental peptide masses a distribution similar to FIG. 4 for theoretical masses may be deduced. The theoretical mass for sequence s, including modifications is referred to as $m_t$. The probability to find an experimental mass close enough to m, is then $$P(P|z, D, s, H_0) \cong f(m_t) z\, D_p,$$

where $f(m_t)$ is the density function of experimental mass distribution. In case the mass tolerance $D_p$ is given in ppms, the probability may be described as $$P(P|z, D, s, H_0) \cong f(m_t/z) D_p,$$

where $f(m_t/z)$ is the density function of experimental mass over charge ratios. If the tolerance is a non-symmetric set $D_p(m_t)$, the formula above is adapted by multiplying length of every interval making $D_p(m_t)$ by the probability to experimentally observe the mass at the center of the interval. The skilled person will readily be able to adapt these methods to the cases where the non-symmetric tolerance is in ppms.

In another aspect of the present invention, the peptide match probability is adjusted by considering the significance of a peptide mass as described herein with respect to hypothesis $H_1$. For instance, $D_p$ being in Daltons, it is found that $$P(P|z, D, s, H_0) \cong P(\text{``significance of } m_t\text{''}|D, H_1) P(m_t|D, H_0) z D_p.$$

$P(F|z, D, s, H_0)$ may be estimated by applying the same techniques as described herein for hypothesis $H_1$, above. First it is found that $$P(F|z, D, s, H_0) \cong \prod_{j \in J} r_{series(f_j)} \prod_{i \in I-J} (1 - r_{series(i)}).$$

In other aspects of the present invention, the HMM for hypothesis $H_1$ above (FIG. 8) may be used; its parameters are learnt from random matches instead of correct matches (see the procedure for $P(W|D, s, H_0)$ above).

In other aspects of the present invention, the null model can have a different structure from the $H_1$ model. For example, the null model of FIG. 9 allows us to compute $$P(F|z, D, s, H_0) \cong \prod_{\vartheta \in S} P(\vartheta|z, D, s, H_0).$$

Referring again to FIG. 1, at step 114, an output may be generated based on the stochastic model and the calculations described above. For example, a likelihood ratio, i.e. the ratio between (i) the probability that the experimental peptide matches the candidate peptide and (ii) the probability that the experimental peptide does not match the candidate peptide, may be generated. According to an embodiment of the invention, the likelihood ratio may be replaced by its logarithm to define score L (log-likelihood ratio or log-odds). In other aspects, the invention may output the likelihood ratio divided by the parent peptide length measured in amino acids. In other embodiments, the invention may output log-likelihood divided by the parent peptide length measured in amino acids. In yet other embodiments, the invention may output log-likelihood divided by the logarithm of the parent peptide length measured in amino acids.

If desired, the match scores computed for peptide matches may be associated with a p-value. This p-value represents the probability of obtaining a score larger than or equal to the computed score by random chance. In theory p-values and match scores are equivalent in differentiating correct from random matches. However, in practice, this may not be the case due to the simplifying assumptions sometimes introduced in calculating L. In such a situation, p-values estimation or alternatively the computation of a Z-score may improve significantly the value of a scoring scheme.

Assuming that the a random match score distribution has an expectation equal to $\mu$ and a standard deviation equal to $\sigma$, a Z-score may be computed according to Z-score=(score−$\mu$)/$\sigma$. The Z-score has a direct interpretation in term of the probability to get such a score.

In one embodiment the p-value may be estimated from an empirical distribution of the top scores. For example, given tolerances $D_p$ and $D_f$, and a set of possible modifications, a library of random peptide sequences is searched using experimental data and the distribution of the top scores is learned. This distribution directly provides by definition an approximation of the p-value.

In one embodiment the p-value may be estimated by assuming a theoretical distribution for the top-scores found in one search for a single experimental peptide. This distribution may for instance be considered normal or Chebyshev (See, e.g., Bafna, V. and Edwards, N. 2001: *SCOPE: a probabilistic model for scoring tandem mass spectra against a peptide database*, Bioinformatics, 17:S13-S21).

In one embodiment an extreme value distribution whose density function has the generic form $$f(w) = e^{-w - e^{-w}}, -\infty < w < \infty,$$

is assumed for the top score of each peptide, where w is a random variable obtained from an appropriate normalization of L (See, e.g., Ewens, W. J. and Grant, G. R. 2001: *Statistical Methods in Bioinformatics*, Springer, New York). This allows for estimating the p-value.

In an embodiment, the p-value may be obtained by generating random peptides according to any model, e.g. a Markov chain, and scoring them. After normalization to Z-scores (subtract mean and divide by standard deviation), this provides a distribution of random scores that may be fitted by a Gaussian to finally infer the p-value. The random score distribution gives the probability to obtain a score s by matching a random (not correct) peptide with probability p. Assuming that the experimental spectrum is compared to N theoretical peptides during database search, the p-value may be estimated by $1-(1-p)^N$.

The above procedures for estimating p-values are different from Tang et al. (Tang, C., Zhang, W., Fenyö, D. and Chait, B. T. 2002: *Method for evaluating the quality of comparison between experimental and theoretical mass data*, U.S. Pat. No. 6,393,367 B1) as the top scores found during database search are not used in combination with bootstrap simulations performed on a random selection of scores found during the database search. Either the top scores are used for themselves or no top scores are used at all like in the preferred embodiment above where random peptides are generated in order to obtain random scores.

The output may represent the match results in a number of formats. For example, the peptides or matches having a score above a predetermined threshold may be reported, or peptides or matches may be reported in the order of their score, e.g. ascending or descending order. In other examples, the returned results also list the protein/peptide modifications used in each case.

According to an embodiment of the present invention, biological information associated with the experimental peptide and the candidate peptide may also be provided in an output generated by the scoring method according to the present invention.

Referring again to FIG. 1, at step 116, physical samples of the experimental peptide or the candidate peptide, along with the related biological information, may be provided based on the match results. For example, if a match between an unknown peptide and a known peptide yields less than confident scores, it may be desirable to produce physical samples of both peptides for further comparison tests in a protein laboratory.

The method ends at step 118.

As discussed above, in one approach, the score $L=P(E|D,s,H_1)/P(E|D,s,H_0)$ considers the probability of observing E according to two competing hypotheses. It should be appreciated that the scoring method according to the present invention may also be adapted to a Bayesian approach of hypotheses testing. Using a Bayesian approach, it is defined that $L'=P(H_1|D,s,E)/P(H_0|D,s,E)$ and apply Bayes' Theorem to compute $L'$ from the same available probabilities as used for the preceding approach. It is found $$P(H_1|D,s,E)=P(E|D,s,H_1)P(D,s,H_1)/P(D,s,E).$$

and $$P(D,s,H_1)=P(H_1|D,s)P(D,s).$$

A similar computation for the null hypothesis combined with the above equations yields $$L'=L\ P(H_1|D,s)/P(H_0|D,s).$$

Hence the difference compared to L is a scaling factor due to the prior probabilities $P(H_1|D,s)$ and $P(H_0|D,s)$. The scaling factor may be estimated by following different approaches. The simplest approximation is $P(H_1)/P(H_0)$, the a priori confidence in identifying the peptide corresponding to an experimental spectrum. This value may be learnt empirically. It is also possible to make use of s because the chance to detect an ion depends on its amino acid composition.

An alternative method is to write $E=(\ldots, Q)$, where Q represents statistics about spectrum quality. By leaving Q apart from the remaining part of E (E represent f the simultaneous realization of several random variables), it is possible to repeat derivation as above to obtain $L''=L\ P(H_1|D,s,Q)/P(H_0|D,s,Q)$. This is an alternative or complementary method to include information about the spectrum quality in the scoring scheme itself.

In one embodiment, the experimental fragment masses are first matched with the theoretical spectrum, applying a mass tolerance $D_{f,1}$, and then a mass shift is deduced so as to recalibrate the experimental data by managing to have the average mass error equal to zero. A second match is computed afterwards with a tolerance $D_{f,2}$ and the score is computed. Such a procedure has been described already for peptide mass fingerprints (See, e.g., Egelhofer, V., Büssow, K., Luebbert, C., Lehrach, H. and Nordhoff, E. 2000: *Improvements in protein identification by MALDI-TOF-MS peptide mapping*, Anal. Chem., 72:2741-2750).

In one embodiment, the data recalibration described above is performed by polynomial regression between the experimental and theoretical data after the initial match at precision $D_{f,1}$.

In one embodiment the scoring system is used to compare two experimental spectra. In an example, the method comprises comparing two experimental spectra using a method that assigns at least a portion of the experimental masses to ion series.

In other examples, the scoring system of the invention may be used to identify proteins: a protein mixture made up of one or a plurality of proteins is analyzed by mass spectrometry. The protein identification procedure may comprise the steps as follows. (1) In a first step, one or more peptide MS/MS spectra are provided. The peptide MS/MS spectra are used as queries and searched against successive peptides in a peptide sequence library. The peptide library has been obtained from a protein sequence library by in-silico digestion. Using the methods of scoring according to the present invention, scores are associated with peptide matches, and the peptides having the n best scores for each experimental peptide are displayed, outputted or stored. (2) In a second step, the peptides originating from a common protein sequence are combined (summed) to assign a score to the protein sequence, where for example the higher a score indicates a higher likelihood to observe a given peptide match. (3) In a third step, the protein sequences are outputted or displayed, e.g. in the order of their scores.

In one embodiment the score assigned to a protein sequence is not the sum of every peptide score. Instead, for each different peptide coming from the protein, only the maximum score is taken in case several experimental peptides have been correlated to the same peptide sequence. The maximum scores of each different peptide sequences are then summed to provide a score for the protein sequence.

The scoring methods of the invention may be used in any suitable peptide or protein identification procedures. In exemplary methods of identifying peptides using the scoring system of the invention, candidate peptides may be filtered based on the taxonomy of the protein they belong to, on the isoelectric point (pI) of the protein they belong to, or on the molecular weight (MW) of the protein they belong to, on inclusion in a non-symmetric mass window, on inclusion in a set of possible masses made of the union of a plurality of mass intervals.

According to an embodiment of the present invention, the scoring method may be applied to diagnose diseases. For example, a peptide associated with one or more diseases may be associated with a "healthy peptide", i.e. one that is not associated with any diseases. The scoring method may be applied to identify the differences in concentration between the two peptides in a control (healthy) patient and a diseased patient to calibrate the diagnostic tool. Further, the scoring method may be applied to measure the two peptides in a patient whose diagnosis is unknown, and compared to the reference levels to yield a diagnostic answer. Diagnosis about the one or more diseases may be based on the matching score and/or the differences identified.

Other applications of the scoring method may include adding inventory of peptides/proteins in a sample, toxicity investigations, and studying activity of a chemical compound.

Figure 11:
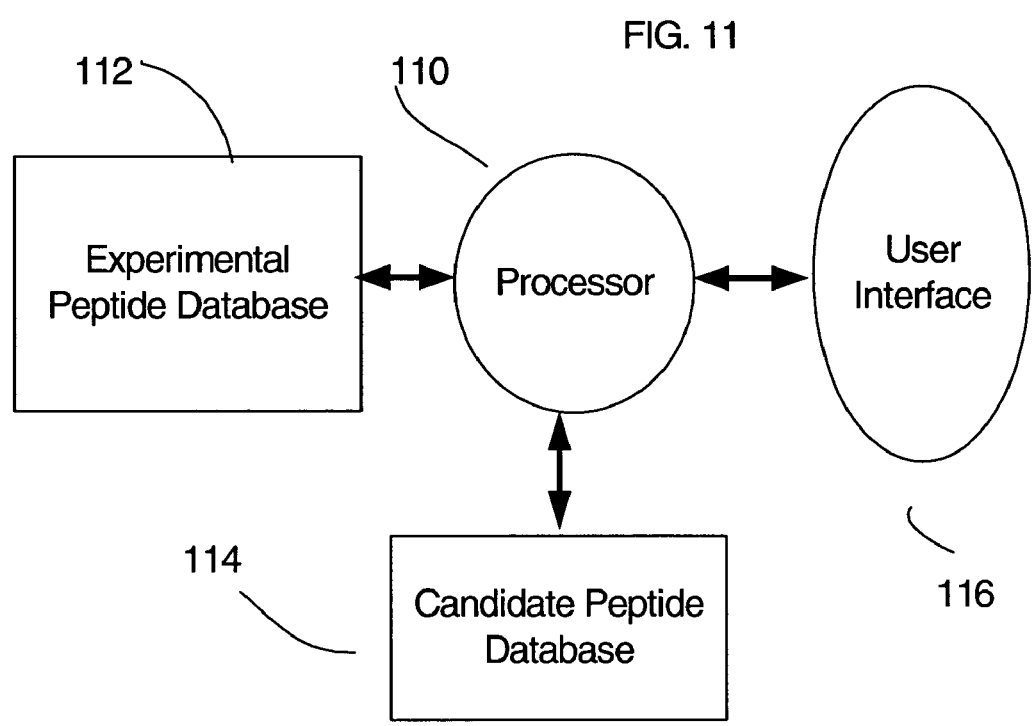
FIG. 11 is a block diagram illustrating an exemplary computer-based system for scoring peptide matches in accordance with one embodiment of the present invention.

Referring to FIG. 11, there is shown a block diagram illustrating an exemplary computer-based system for scoring peptide matches in accordance with one embodiment of the present invention. The system may comprise Processor 110, Experimental Peptide Database 112, Candidate Peptide Database 114 and User Interface 116. According to embodiments of the invention, the system may be implemented on computer(s) or a computer-based network. Processor 110 may be a central processing unit (CPU) or a computer capable of data manipulation, logic operation and mathematical calculation. According to an embodiment of the invention, Processor 110 may be a standard computer comprising at least an input device, an output device, a processor device, and a data storage device storing a module that is configured so that upon receiving a request to identify mass spectrometry data, it performs the steps listed in any one of the methods of the invention described above. Experimental Peptide Database 112 may be one or more databases containing experimental data associated with one or more peptides to be identified. Candidate Peptide Database 114 may be one or more peptide libraries or databases containing information associated with known peptides. According to an embodiment of the invention, databases 112 and 114 may be implemented with a single database or separated databases. User Interface 116 may be a graphical user interface (GUI) serving the purpose of obtaining inputs from and presenting results to a user of the system. According to embodiments of the invention, the User Interface module may be a display, such as a CRT (cathode ray tube), LCD (liquid crystal display) or touch-screen monitor, or a computer terminal, or a personal computer connected to Processor 110.

The computer-based system may be used in a wide range of applications where peptides and proteins are to be identified. The systems of the invention may be designed to permits the steps of: a) accessing a database of nucleic acid or amino acid sequences and/or mass spectra, e.g. experimental spectra; b) inputting an experimental mass spectrum or information derived therefrom, and interrogating said database to identify one or more candidate peptide sequences or mass spectra that are related to or derived from the same protein as, the peptide for which the experimental mass spectrum is provided; and c) outputting or displaying information concerning said candidate peptides. Each candidate peptide can thereby be associated with a score as disclosed herein. For example, the system can output a list of peptides (using an identifier or some other description such as amino acid sequence) and associated match scores. The score may be an indication of the probability or likelihood that a candidate peptide is or is not related or corresponding to the mass spectrum, and/or that a candidate peptide is more likely to correspond to the experimental peptide that another candidate peptide.

The performance of two embodiments of the present invention is evaluated below. It should be appreciated that these following examples are for illustrative purposes only and not meant to limit the scope of the present invention.

EXAMPLE 1

Performance Comparison with Mascot

Figure 3:
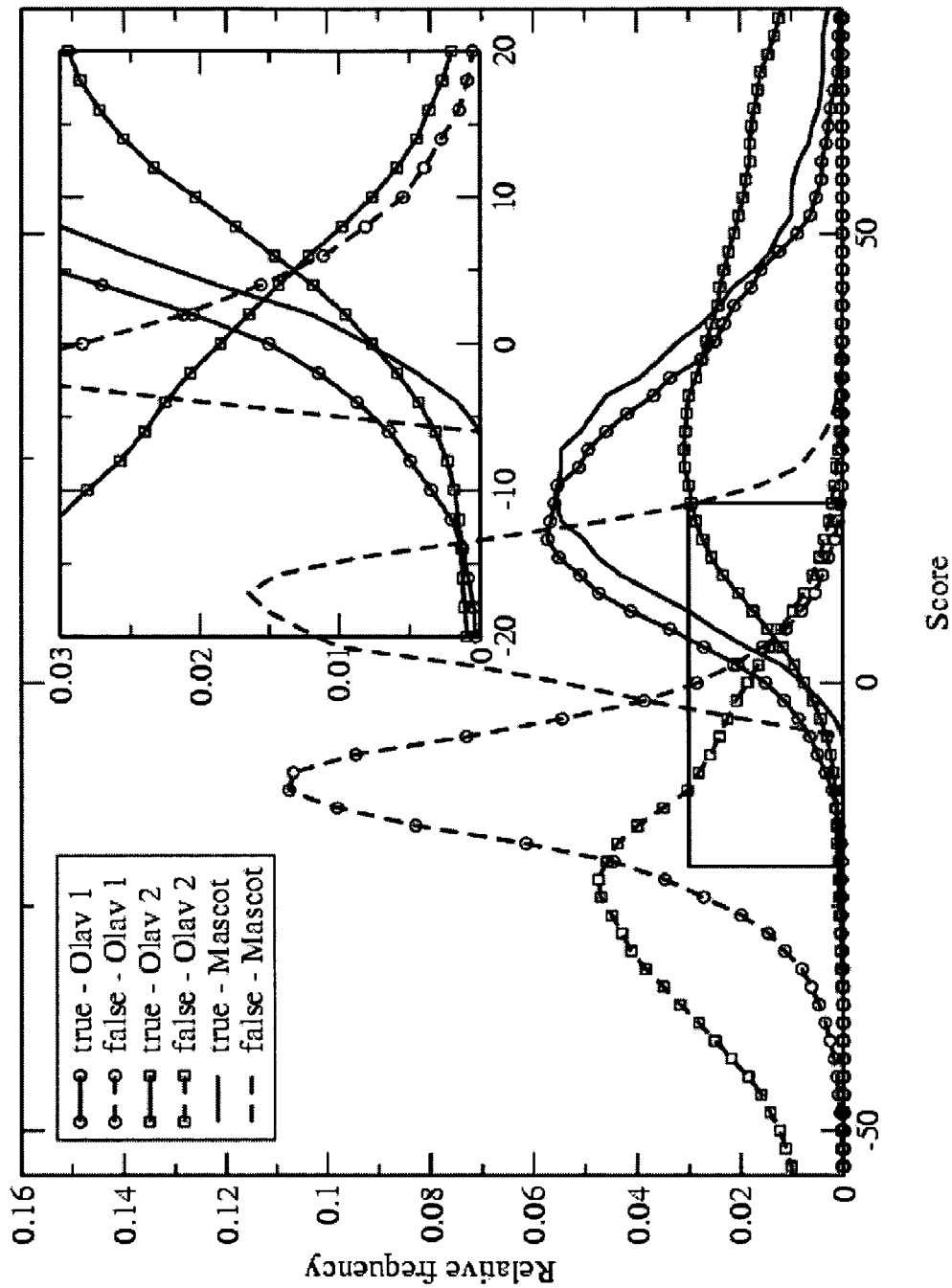
FIG. 3 is an illustration of the performance of two configurations of the scoring system (Olav 1, based on E=(F,z) and computed by using Formula (F1), and Olav 2 based on E=(F, z,P,W) and computed by using the HMM of FIG. 8) compared to Mascot 1.7, a well-established commercial solution (See, e.g., Perkins, D. N., Pappin, D. J., Creasy, D. M. and Cottrell, J. S. 1999: *Probability-based protein identification by searching sequence databases using mass spectrometry data*, Electrophoresis, 20(18):3551-3567) available from Matrix Science Ltd., in accordance with one embodiment of the invention.

The performance of one of a leading commercial product known as Mascot was compared to the scoring system of the invention. FIG. 3 illustrates the performance of two configurations of the disclosed scoring system (Olav), referred to as Olav 1 and Olav 2, against Mascot (See, e.g., Perkins, D. N., Pappin, D. J., Creasy, D. M. and Cottrell, J. S. 1999: *Probability-based protein identification by searching sequence databases using mass spectrometry data*, Electrophoresis, 20(18):3551-3567). The Olav 1 score was based on E=(F,z) and computed by using Formula (F1), while the Olav 2 was based on E=(F,z,P,W) and computed by using the HMM of FIG. 8. The set of matches used for computing the above distributions was made of 11,000 Mascot false positives and 2,500 true positives as determined by manual analysis of mass spectra. For each system, FIG. 3 shows a continuous line corresponding to positive identifications and a broken line corresponding to negative identifications. It is clear that the intersection of true positive and false positive identifications is substantially lower using Olav that using Mascot, indicating fewer ambiguous and erroneous matches using Olav. Mascot parameters were set to the best possible as determined by manual analysis of mass spectra.

EXAMPLE 2

Performance Comparison with Dancik et al.

Figure 6:
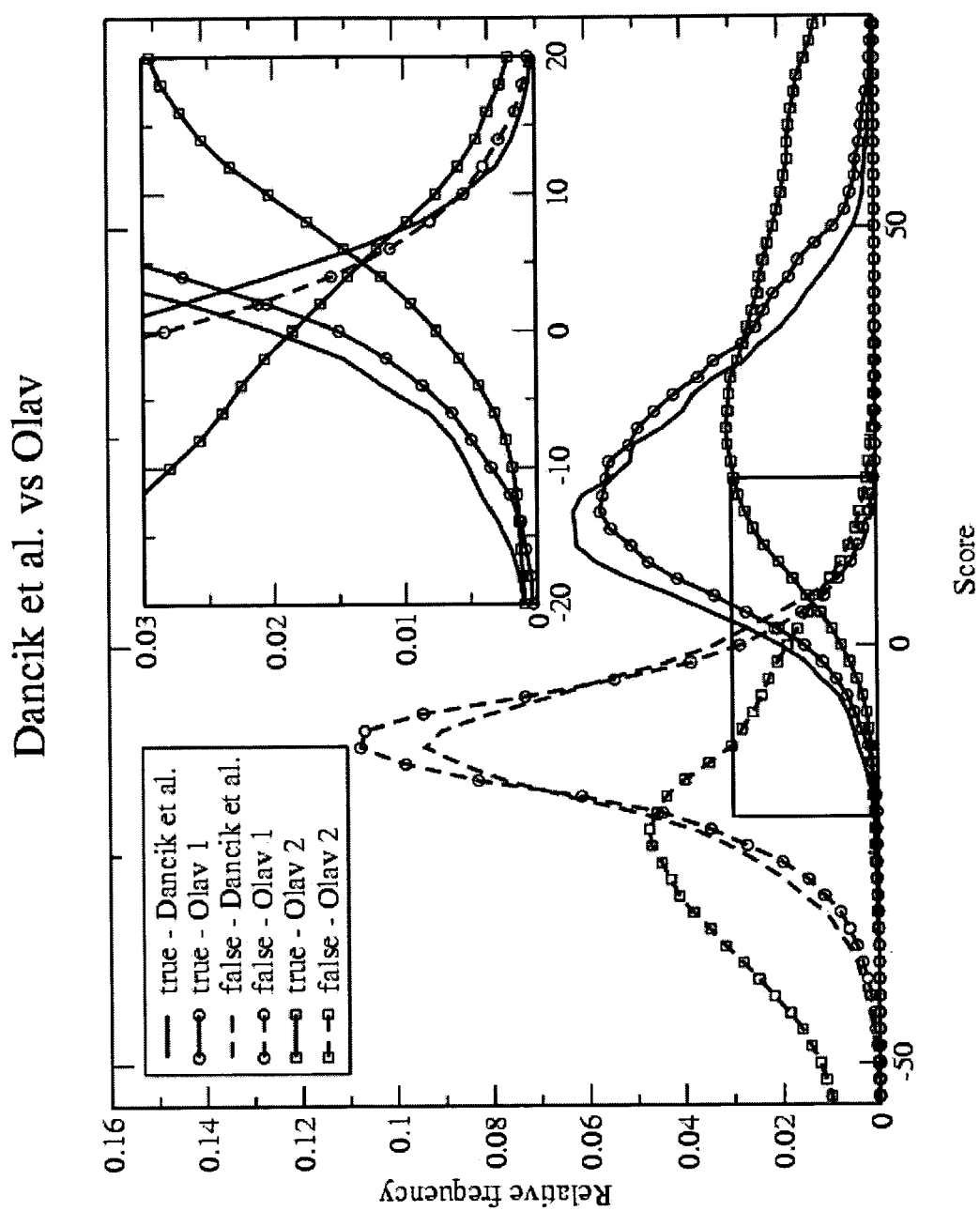
FIG. 6 shows a comparison between the scoring system of Dancik et al., Olav 1, based on E=(F,z) and computed by using Formula (FI), and Olav 2 based on E=(F,z,P,W) and computed by using the HMM of FIG. 8.

The performance of the disclosed scoring system was also compared with the method of Dancik et al. (Dancik, V., Addona, T. A., Clauser, K. R., Vath, J. E. and Pevzner, P. A. 1999: *De novo peptide sequencing viatandem massspectrometry: a graph-theoretica approach*, J. Comp. Biol., 6:327-342), which is based on a simple decision theoretic approach. FIG. 6 shows a comparison between Dancik et al. scoring, Olav 1, based on E=(F,z) and computed by using Formula (F1) and Olav 2 is based on E=(F,z,P,W) and computed by using the HMM of FIG. 8. We observe that Olav 1 is in fact the scoring from Dancik et al., with the addition of a dependency on parent peptide charge. For each system, FIG. 6 shows a continuous line corresponding to positive identifications and a broken line corresponding to negative identifications. The difference in performance illustrates the interest of including more observations in E than F only (Olav 1 and 2), and it illustrates the interest of using stochastic models that consider the structure of the match (Olav 2, series of successive matches). It is also interesting to note that Dancik et al. system is superior to Mascot (compare FIGS. 3 and 6). This illustrates the advantage of a system based on a model instead of an empirical approach.

EXAMPLE 3

Performance Testing with Experimental Spectra

In one embodiment of the invention, the scoring method was applied to liquid chromatography (LC) ion-trap and Q-TOF spectra obtained from human plasma. The proteins present in human plasma were separated by multidimensional LC, resulting in thousands of samples. Each sample was digested by trypsin and then analyzed by MS. It is important to note that the data used were real production data obtained from real samples. The complexity of the sample varies from 0 to 20+ proteins. 40 ion-trap and 2 Q-TOF instruments were used during the acquisition. Four independent data sets were used to report results, all of which had been checked manually. Set A, ion-trap, was made of 2933 correct peptide matches, 324 different peptides. Set B, Q-TOF, was made of 241 correct peptide matches, 121 different peptides. Set C, ion-trap, was made of 11,000 Mascot false positives, 7595 different peptides. Set D, ion-trap, was made of 2363 correct peptide matches, 468 different peptides. Set D was included because the spectrum quality of C did not match A but D due to different laboratory processes.

Performance results for two instances of Olav scoring schemes were obtained and compared with Mascot 1.7, where the Mascot parameters were set to be the best possible. Parameters for Olav alternative model were learnt empirically from data sets A, B and/or D based on Maximum Likelihood estimation. The random matches used for training the null model were obtained from random peptide sequences generated by an order 3 Markov chain trained on SWISS-PROT digested human entries.

Figure 13:
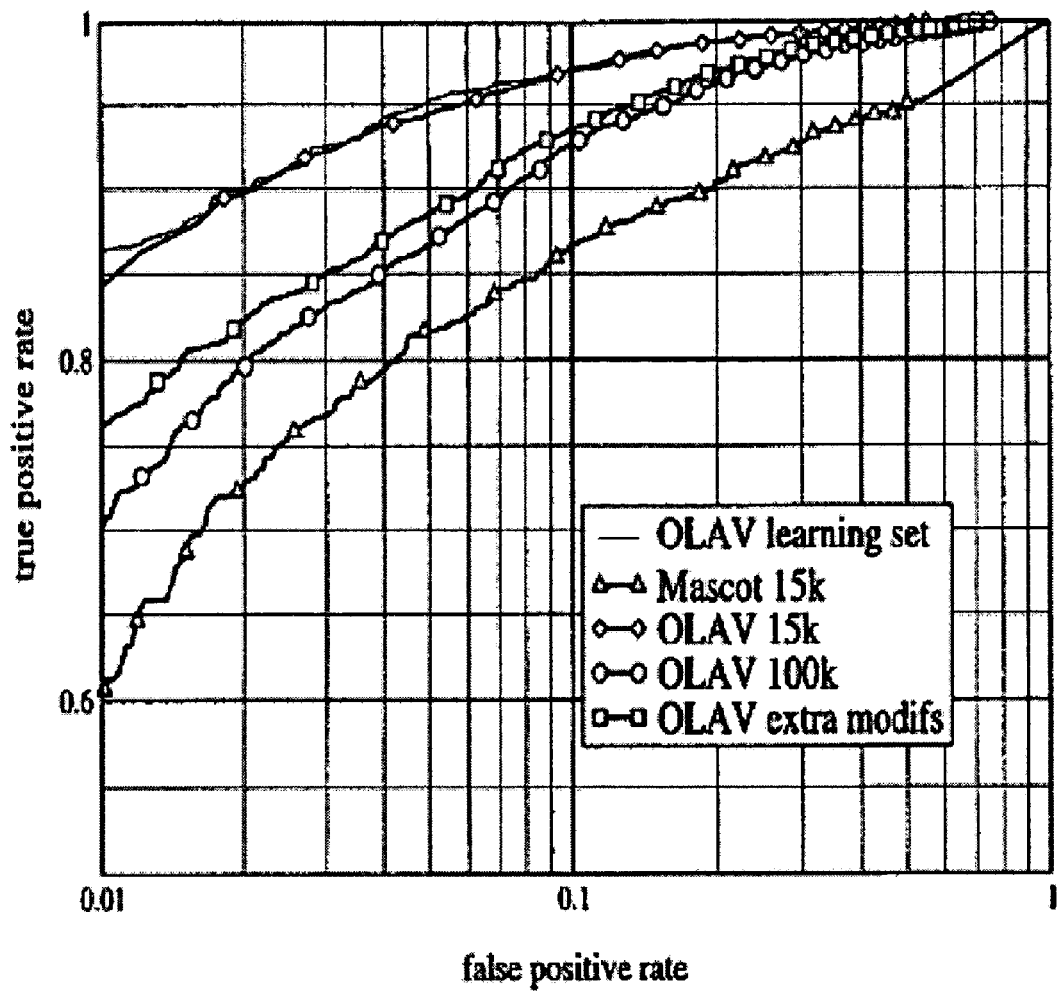
FIG. 13 shows Olav performance on ion-trap data in one exemplary embodiment of the present invention.

The general procedure used to estimate the performance is as follows. 20% of the reference sets are extracted to build a test set (random selection). The model is then trained on the remaining 80% and tested on the test set. This operation is repeated 10 times and the results are averaged. To estimate the true and false positive rates, a threshold is put on the score or p-value. Namely, in a correct match set, every match that is selected by the threshold is a true positive and every match that is not selected is a false negative. In a random match set, selected matches are false positives and rejected matches are true negatives. In FIG. 13, there is shown a Receiver Operating Characteristics (ROC) curve obtained by testing and learning on the same set for comparison with the ROC curve obtained by the performance estimation procedure. The curves "Olav learning set" and "Olav 15k" are almost identical, which means there is no over-fitting.

Figure 9:
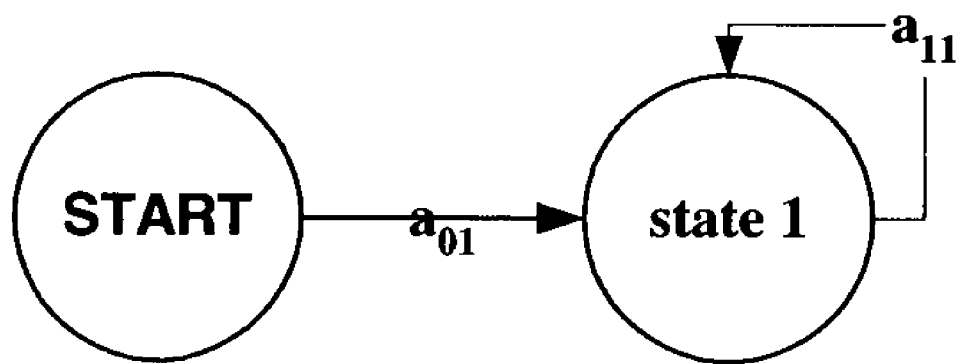
FIG. 9 illustrates a model of random ion series match, e.g. the null hypothesis, in accordance with an embodiment of the present invention.

For ion-trap data, Olav uses E=(P, F, z, W), and peak intensities are considered. Lemma 1 is applied. The stochastic model is based on Formula (F1), the HMMs as illustrated in FIGS. 8 and 9, and the following score representation:

$$L = \log\left(\frac{P(P|D, s, H_1)P(F|z, D, s, H_1)P(z|D, s, H_1)}{P(P|D, s, H_0)P(F|z, D, s, H_0)P(z|D, s, H_0)}\right)$$

where the distribution of z with respect to peptide length is learnt empirically. A product of assumed independent probabilities is used for W. The peak intensities of b and y fragments are considered an independent observation.

For Q-TOF data, only a simplified model made of the HMM and the model for peak intensities is used.

Figure 12:
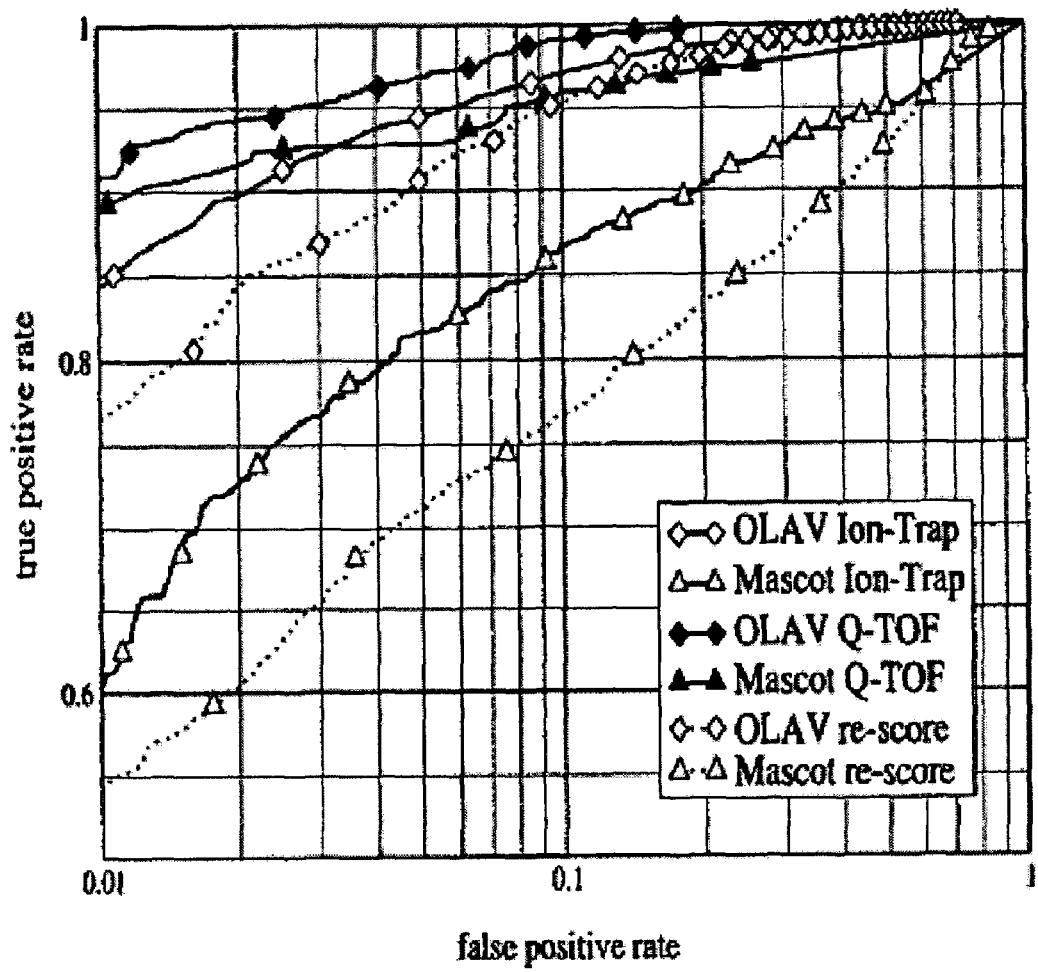
FIG. 12 shows the relative performance of Olav and Mascot in one exemplary embodiment of the present invention.

In FIG. 12, there is shown the relative performance of Olav and Mascot on match sets C and D by searching against a database of 15,000 human proteins. To further compare the performance of Olav and Mascot, independently of Mascot true/false positives, a database of 15,000 random protein sequences is generated by using an order 3 Markov model trained on SWISS-PROT human sequences. Test set B is also used on the same random database. It can be observed that Olav performs significantly better than Mascot in every comparison: at 95% true positive rate, the false positive rate is reduced by a factor of 8.5 for ion-trap and 3 for Q-TOF.

In FIG. 13, there is shown Olav performance on ion-trap data (set A) when more variable modifications are allowed or when the database is much larger (100,000 entries). It can be observed that the Olav false positive rate grows slower than the database size, which is a very desirable property for a scoring scheme.

Figure 14:
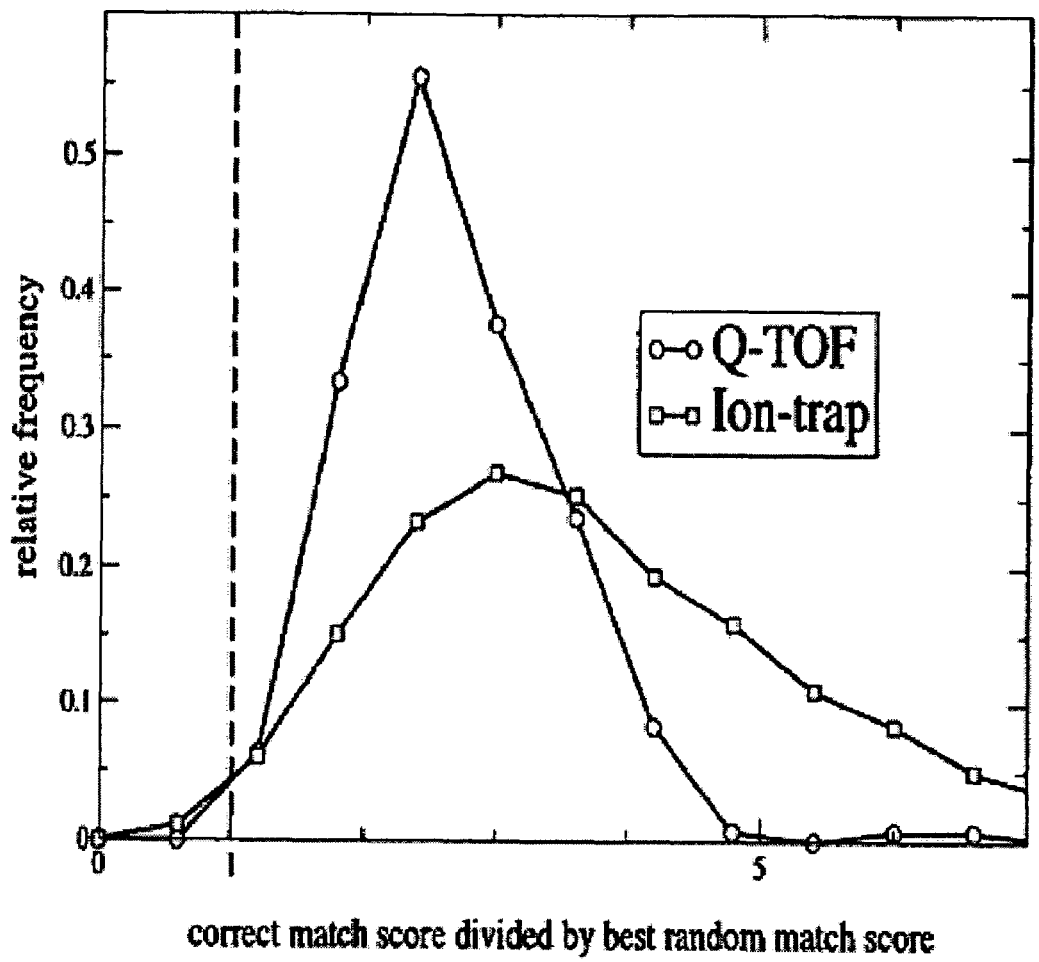
FIG. 14 shows the distribution of score ratios in one exemplary embodiment of the present invention.

In FIG. 14, there is shown the distribution of score ratios between the best among 5,000 random matches and the correct match (sets A and B). The computation of p-value through a randomization procedure may restore part of the optimality of the likelihood ratio lost in simplifying assumptions. FIG. 14 shows the intrinsic performance of the score function. The p-values may in fact be superior to the score to set a common threshold, independent of the peptide. The performance of the score is measured on each peptide separately.

EXAMPLE 4

Analysis of Ion Trap Tandem MS

In another embodiment of the present invention, the importance of a number of matcher characteristics were studied systematically. Multidimensional liquid chromatography was applied to liter-scale volumes of human plasma, yielding roughly 13,000 fractions, which were digested by trypsin and analyzed by mass spectrometry (LC-ESI-IT) by 40 Bruker Esquire 3000 instruments, available from Bruker Daltonics Inc. The set of ion trap mass spectra used was made of 146,808 correct matches, 33,000 of which have been manually validated. The other matches were automatically validated by a procedure, which, in addition to fixed thresholds, includes biological knowledge and statistics about the peptides that were validated manually. There were 3,329 singly charged peptides (436 distinct), 82,415 doubly charged peptides (3,039 distinct) and 61,064 triply charged peptides (2,920 distinct). Every performance reported in this example was obtained by randomly selecting independent training and test sets, whose sizes were 3,000 and 5,000 matches respectively. This procedure was repeated five times and the results averaged. Both model parameters and performance barely changed from set to set.

A minimal score function $L_1$ is defined and evaluated in this embodiment. It is based on a key statistical observation: the probability $p_\theta(z)$ to detect each ion type $\theta$ is not constant. Let $s=a_1, a_2, \ldots, a_n$ be a peptide sequence and $a_i$ amino acids. Let $S(s,i) \subset S$ be the set of ion types with an experimental fragment mass matching $a_i$ ($a_i$ is the last amino acid of the fragment, mass tolerance given). Assuming the independence of the fragment matches, it is defined that $$L_1 = \log\left(\prod_{i=1}^{n}\left[\prod_{\theta \in S(s,i)} \frac{p_\theta(z)}{r_\theta(z)} \prod_{\theta \in S-S(s,i)} \frac{1-p_\theta(z)}{1-r_\theta(z)}\right]\right).$$

$p_\theta(z)$, $\theta \in S$, are learnt from a set of correct matches. The probabilities of random fragment matches $r_\theta(z)$ are learnt from random peptides. $S(s,i) \subset S$ is not restricted by the matched fragments only. It is also restricted because certain ions are not always possible (neutral loss). Relative entropy in bit $H_\theta(z)=p_\theta(z)\log_2(p_\theta(z)/r_\theta(z))$ is used to measure the importance of each ion type. The basic reference score function was modified to evaluate the importance of consecutive fragment matches, signal intensity and amino acid dependence. It was found that the basic $L_1$ score may be significantly improved by considering signal intensity. Consecutive fragment matches as well as the amino acid dependent version of $L_1$ may also improve the performance.

EXAMPLE 5

Performance on Bruker Esquire 3000 Ion Trap Instrument

Figure 15:
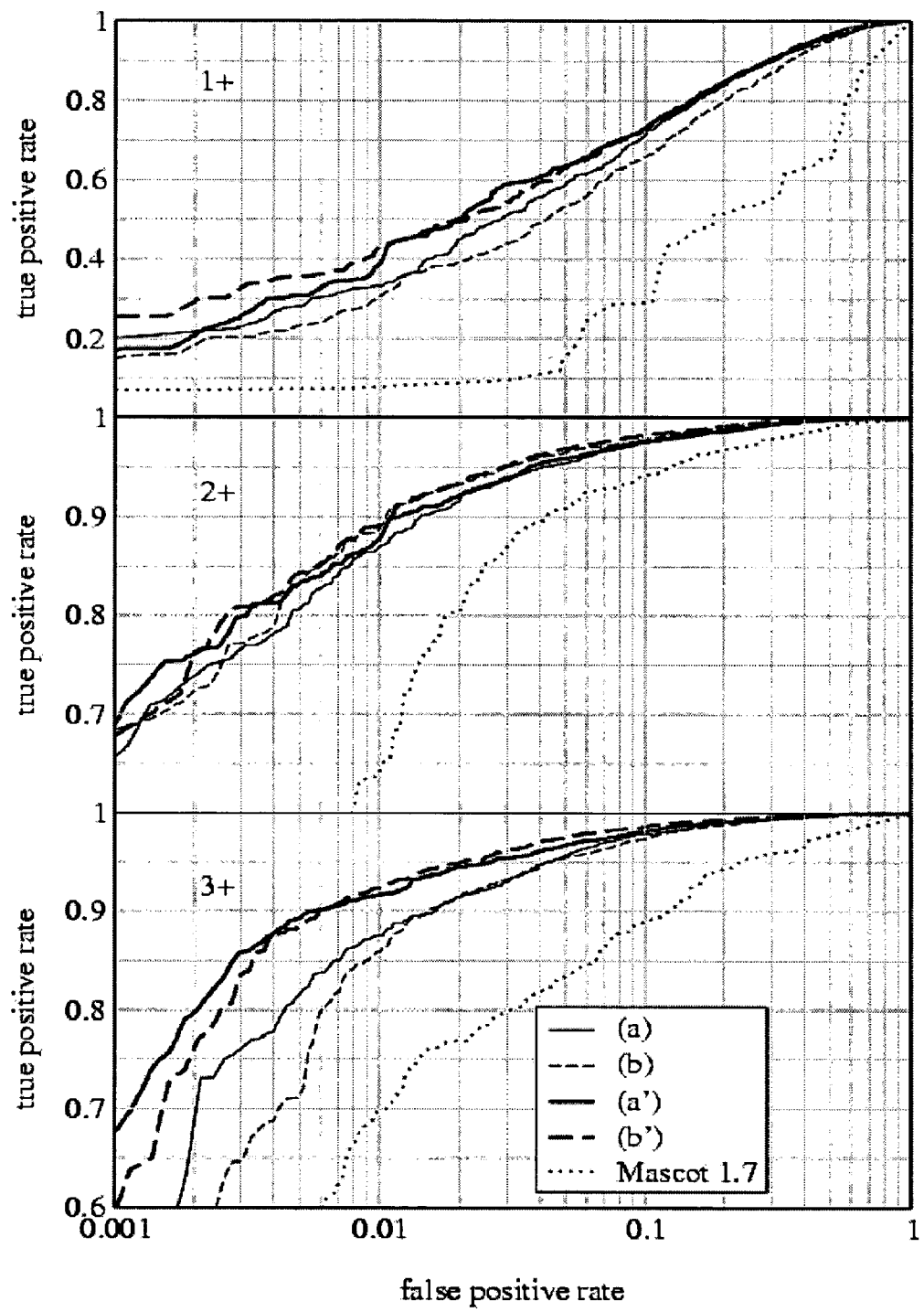
FIG. 15 illustrates the performance of four instances of the disclosed scoring system compared to Mascot 1.7 on a very large set of Bruker Esquire 3000 ion trap data.

FIG. 15 illustrates the performance of four instances of the disclosed scoring system compared to Mascot 1.7 on a very large set of Bruker Esquire 3000 ion trap data. The set comprises 3329 singly, 82415 doubly and 61064 triply charged peptides. (a) Fragment match probabilities (formula (F1)), fragment intensity (use the rank in the peak list intensities). (a') The same with fragment match probabilities by amino acid class (see Detailed Description). (b) Same as (a) with consecutive fragment matches (HMM). (b') Same as (a') with consecutive fragment matches (HMM). The performance is reported as a receiver operating characteristics (ROC) like curve, which plots true versus false positive rates obtained by setting various thresholds on the p-values. The true positive rate is estimated by searching against database of 15000 proteins that contain the peptides of the reference data set. The false positive rate is estimated by searching against a database of 15000 random proteins. The random proteins are generated by an order 3 Markov chain trained on the first protein database. Cys_CAM and oxidation (Met, His, Try) are set as variable modifications.

EXAMPLE 6

Performance on Bruker Esquire 3000+ Ion Trap Instrument

Figure 16:
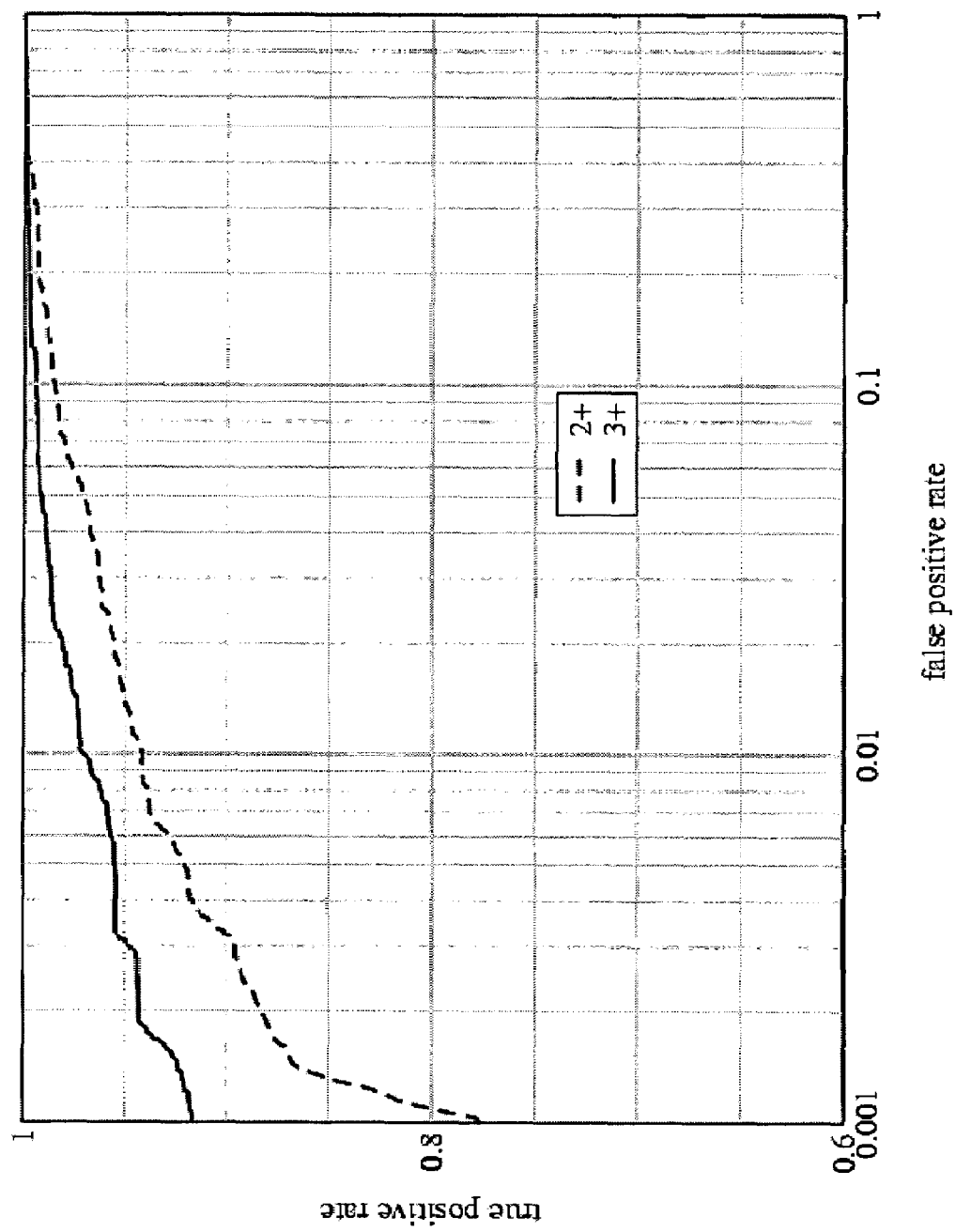
FIG. 16 illustrates the performance of one instance of the disclose scoring system on a large collection of ion trap data acquire on Esquire 3000+.

FIG. 16 illustrates the performance of one instance of the disclosed scoring system on a large collection of ion trap data acquired on a Bruker Esquire 3000+ instrument. The data set comprises 6800 doubly and triply charged peptides. The scoring uses fragment match probabilities by amino acid class, fragment intensity and consecutive fragment matches (parameters reported in Table 6). The performance is reported as a receiver operating characteristics (ROC) like curve, which plots true versus false positive rates obtained by setting various thresholds on the p-values. The true positive rate is estimated by searching against database of 15000 proteins that contain the peptides of the reference data set. The false positive rate is estimated by searching against a database of 15000 random proteins. The random proteins are generated by an order 3 Markov chain trained on the first protein database. Cys-CAM and oxidation (Met, His, Try) are set as variable modifications.

EXAMPLE 7

Performance on ThermoFinnigan LCQ Ion Trap Instrument

Figure 17:
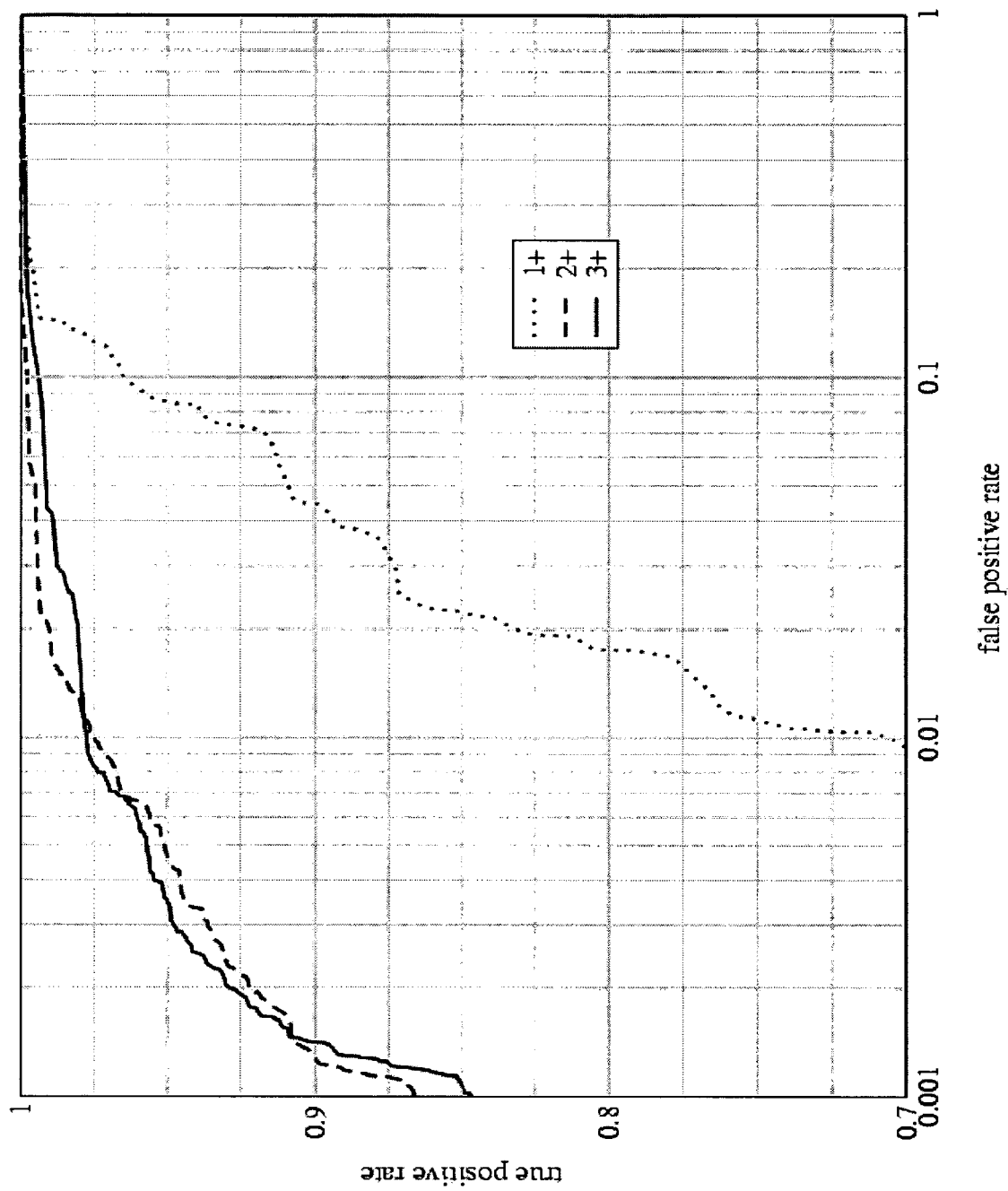
FIG. 17 illustrates the performance of one instance of the disclosed scoring system on a LCQ data set of 2700 peptides that is available on request from Keller et al. (See, e.g., Keller, A., Purvine, S., Nesvizhskii, A. I., Stolyar, S., Goodlett, D. R. and Kolker, E. 2002: *Experimental protein mixture for validating tandem mass spectral analysis*, OMICS, 6:207-212).

FIG. 17 illustrates the performance of one instance of the disclosed scoring system on a LCQ data set of 2700 peptides that is available on request from Keller et al. (See, e.g., Keller, A., Purvine, S., Nesvizhskii, A. I., Stolyar, S., Goodlett, D. R. and Kolker, E. 2002: *Experimental protein mixture for validating tandem mass spectral analysis*, OMICS, 6:207-212). The scoring uses fragment match probabilities by amino acid class, fragment intensity and consecutive fragment matches. The performance is reported as a receiver operating characteristics (ROC) like curve, which plots true versus false positive rates obtained by setting various thresholds on the p-values. The true positive and false positive rates are estimated by searching a database also provided by Keller et al. For comparison, if a true positive rate of 95% is required, a false positive rate may be achieved that approximately improves by a factor 18 over what is proposed by Keller et al. (See e.g. Keller, A., Nesvizhskii, A. I., Kolker, E. and Aebersold, R. 2002: *Empirical statistical model to estimate the accuracy of peptide identification made by MS/MS and database search*, Anal. Chem., 74:5385-5392).

EXAMPLE 8

Performance on a Q-TOF Instrument

Figure 18:
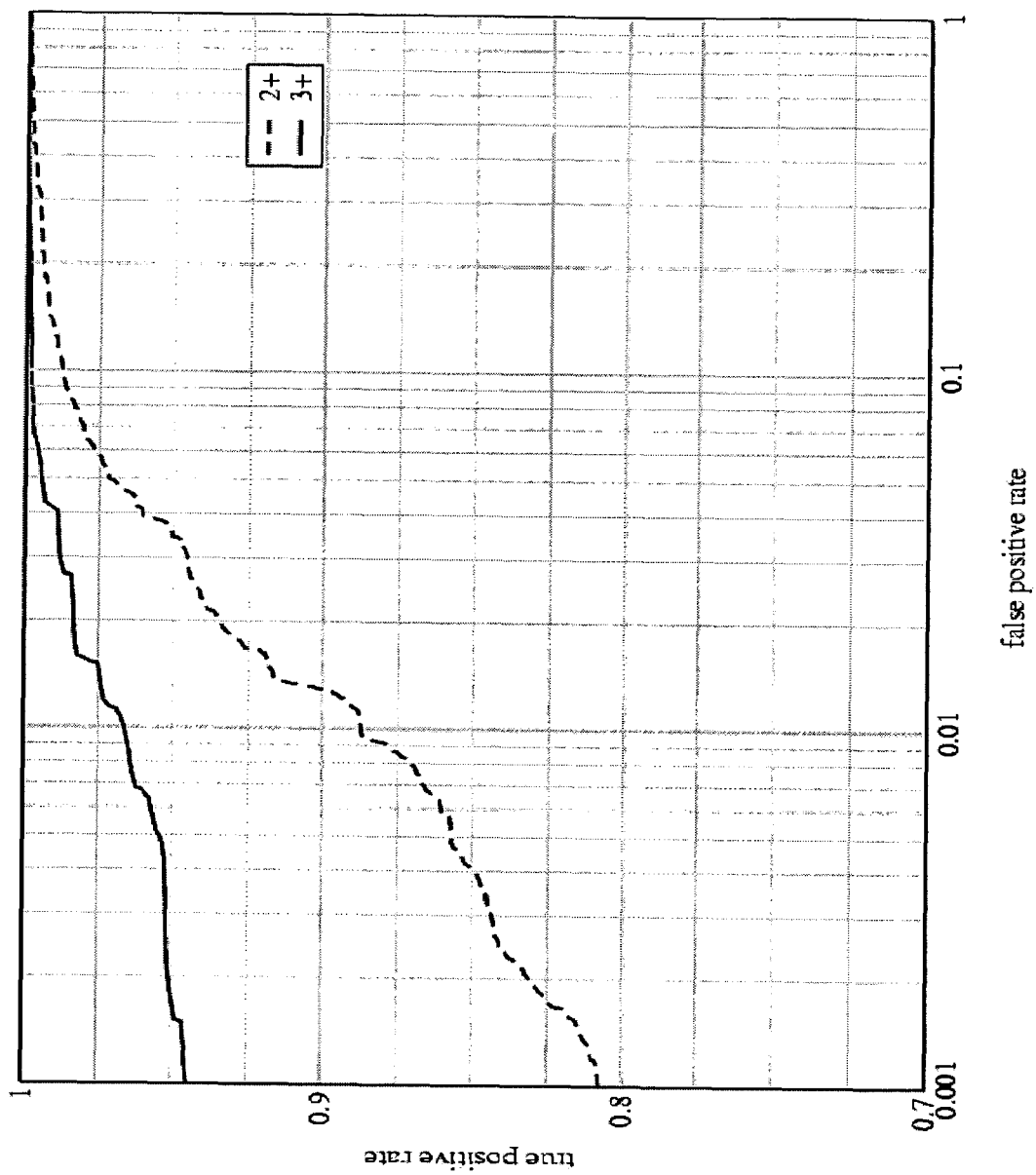
FIG. 18 illustrates the performance of one instance of the disclosed scoring system on a set of 1697 doubly and triply charged peptides.

The disclosed scoring system can be applied to any mass spectrometry technology by illustrating its performance on a QTOF instrument available from Micromass Ltd. FIG. 18 illustrates the performance of one instance of the disclosed scoring system on a set of 1697 doubly and triply charged peptides. The scoring uses fragment match probabilities, fragment intensity, immonium ions and consecutive fragment matches. The performance is reported as a receiver operating characteristics (ROC) like curve, which plots true versus false positive rates obtained by setting various thresholds on the p-values. The true positive rate is estimated by searching against database of 15000 proteins that contain the peptides of the reference data set. The false positive rate is estimated by searching against a database of 15000 random proteins. The random proteins are generated by an order 3 Markov chain trained on the first protein database. Cys_CAM and oxidation (Met, His, Try) are set as variable modifications.

EXAMPLE 9

Parameter Set of One Scoring System Instance for Esquire 3000+

In Table 6, there are listed the values of the parameters used in the scoring system that uses fragment match probabilities by amino acid class, fragment intensity and consecutive fragment matches, see also FIG. 16.

It should be appreciated that the methods and systems of the invention can be used with a number of different apparati and mass spectrometry protocols. The scoring system or model of the invention may be readily adapted to the experimental environment of interest. For example, the stochastic model itself, e.g. the match characteristics that are to be considered and their degree of dependency on other factors, can be adapted. Also, the parameters used in weighting the effect of different match characteristics in the overall score may be adapted. At least two ways of learning the parameters and model to be used are possible. One is to provide a data set (e.g. experimental spectra) which has been manually verified and adjust the parameters and model to obtain an improved scoring accuracy. Another method is to provide a set of known protein standards and adjust the parameters and model to obtain improved scoring accuracy.

It should also be appreciated that the system and method for scoring peptide matches as described in the present invention may be implemented in a stand-alone manner or be combined with or embedded in other hardware or software applications. For example, other software programs may operate by taking the output or by feeding the input of the present invention. Such implementations are intended to fall within the scope of the present invention.

At this point it should be noted that the system and method in accordance with the present invention as described above typically involves the processing of input data and the generation of output data to some extent. This input data processing and output data generation may be implemented in hardware or software. For example, specific electronic components may be employed in a computer and communication network or similar or related circuitry for implementing the functions associated with scoring peptide matches in accordance with the present invention as described above. Alternatively, one or more processors operating in accordance with stored instructions may implement the functions associated with scoring peptide matches in accordance with the present invention as described above. If such is the case, it is within the scope of the present invention that such instructions may be stored on one or more processor readable carriers (e.g., a magnetic disk), or transmitted to one or more processors via one or more signals.

The present invention is not to be limited in scope by the specific embodiments described herein. Indeed, other various embodiments of and modifications to the present invention, in addition to those described herein, will be apparent to those of ordinary skill in the art from the foregoing description and accompanying drawings. Thus, such other embodiments and modifications are intended to fall within the scope of the following appended claims. Further, although the present invention has been described herein in the context of a particular implementation in a particular environment for a particular purpose, those of ordinary skill in the art will recognize that its usefulness is not limited thereto and that the present invention may be beneficially implemented in any number of environments for any number of purposes. Accordingly, the claims set forth below should be construed in view of the full breadth and spirit of the present invention as disclosed herein. Furthermore, several references have been cited in the present disclosure. Each of the cited references is incorporated herein by reference.

What is claimed is:

1. A method for scoring a match of two peptides, the method comprising:
   providing information associated with an experimental peptide, where the information comprises at least mass spectrum information associated with the experimental peptide and at least one fragment of the experimental peptide;
   providing information associated with a candidate peptide;
   defining an extended match E based on the information associated with the experimental peptide and the information associated with the candidate peptide, the extended match E being a probabilistic function of a tuple of random variables that include at least a fragment match and a peptide match between the experimental peptide and the candidate peptide;
   generating a stochastic model based on the information associated with the experimental peptide and the information associated with the candidate peptide, the stochastic model incorporating a probability distribution of each of the random variables;
   scoring the extended match E based on a likelihood ratio $$L = \frac{P(E|D, s, H_1)}{P(E|D, s, H_0)},$$

where
   D is any extra information that is associated with the experimental peptide and the candidate peptide;
   s is a peptide sequence associated with the candidate peptide;
   $H_1$ is a hypothesis that the peptide sequence s is the correct sequence of the experimental peptide;
   $H_0$ is a null-hypothesis that the peptide sequence s is an erroneous sequence of the experimental peptide; and
   probabilities $P(E|D,s,H_1)$ and $P(E|D,s,H_0)$ are calculated based on the stochastic model; and
   outputting, in a user readable format, a result of the step of scoring the extended match E.

2. The method according to claim 1, where the extended match E is a random variable that further comprises one or more random variables, the one or more random variables being selected from a group consisting of:
   peptide match P that characterizes a match between the experimental peptide mass m and the candidate peptide mass $m_t$;
   fragment match F that characterizes a match between fragment masses $f_j$ of the experimental peptide and fragment masses $mt_{t,j}$ of the candidate peptide, where j is an index for the fragment masses of the experimental peptide;
   charge z that is used to match the m/z ratio of the experimental peptide with the candidate peptide;
   elution time t of the experimental peptide;
   number of missed cleavages k in the candidate peptide matching the experimental peptide;
   protein/peptide modifications W made to the candidate peptide to match the experimental peptide; and
   any random variables observable or derivable based on the information associated with the experimental peptide and the candidate peptide.

3. The method according to claim 2 further comprising determining the probability distributions for the one or more random variables based on at least one of a Hidden Markov Model and an artificial neural network.

4. The method according to claim 2 further comprising determining an empirical probability distribution for the one or more random variables based on matches between experimental data for known peptides and peptides in a peptide database.

5. The method according to claim 1 further comprising estimating the probabilities $P(E|D,s,H_1)$ and $P(E|D,s,H_0)$ based on the lemma $P(A,B|C)=P(A|B,C)P(B|C)$, where A, B and C are random variables.

6. The method according to claim 1 further comprising calculating at least one of:

$$\text{Bayesian score } L' = \frac{P(H_1|D, s, E)}{P(H_0|D, s, E)} = L\frac{P(H_1|D, s)}{P(H_0|D, s)}; \text{ and}$$

$$\text{Bayesian score } L'' = L\frac{P(H_1|D, s, Q)}{P(H_0|D, s, Q)},$$

where Q represents statistics associated with mass spectrum quality of the experimental peptide.

7. The method according to claim 1 further comprising:
   comparing the candidate peptide mass with the experimental peptide mass; and
   scoring the extended match E based on the likelihood ratio L, if the difference between the candidate peptide mass and the experimental peptide mass is in a predetermined range.

8. The method according to claim 1 further comprising adjusting the stochastic model and a plurality of parameters associated with the stochastic model based on a learning data set, where the learning data set comprises a plurality of peptides that have been identified or a set of known protein standards.

9. The method according to claim 1 further comprising generating an output, where the output comprises at least one of:
   a match score associated with the candidate peptide, where the match score comprises at least one of
     the likelihood;
     a log-likelihood, where the log-likelihood is the logarithm of the likelihood ratio;
     the likelihood ratio divided by the length of the experimental peptide measured in amino acids;
     the log-likelihood divided by the length of the experimental peptide measured in amino acids; and
     the log-likelihood divided by the logarithm of the length of the experimental peptide measured in amino acids;
   a Z-score associated with the match score;
   a p-value associated with the match score;
   biological information associated with the experimental peptide; and
   biological information associated with the candidate peptide.

10. The method according to claim 1, where a theoretical fragmentation spectrum is provided for the candidate peptide.

11. The method according to claim 10, where the theoretical fragmentation spectrum includes masses corresponding to fragment isotopes.

12. The method according to claim 1 further comprising filtering the candidate peptide based on at least one of:
    the taxonomy of the protein that the candidate peptide belongs to;

the isoelectric point of the protein that the candidate peptide belongs to;

the molecular weight of the protein that the candidate peptide belongs to;

a non-symmetric mass window; and a set of possible masses made of the union of a plurality of mass intervals.

13. The method according to claim 1 further comprising providing a physical sample of the experimental peptide and biological information associated with the experimental peptide; and providing a physical sample of the candidate peptide and biological information associated with the candidate peptide.

14. A method for scoring a match of two peptides, the method comprising:

providing information associated with an experimental peptide, where the information comprises at least mass spectrum information associated with the experimental peptide and at least one fragment of the experimental peptide;

providing information associated with a candidate peptide;

defining an extended match E based on the information associated with the experimental peptide and the information associated with the candidate peptide, the extended match E being a probabilistic function of a tuple of random variables that include at least a consecutive fragment match between the experimental peptide and the candidate peptide;

generating a stochastic model based on the information associated with the experimental peptide and the information associated with the candidate peptide, the stochastic model incorporating a probability distribution of each of the random variables, wherein the probability distribution associated with the consecutive fragment match is determined based on a Hidden Markov Model;

scoring the extended match E based on a likelihood ratio $$L = \frac{P(E|D, s, H_1)}{P(E|D, s, H_0)},$$

wherein:

D is any extra information that is associated with the experimental peptide and the candidate peptide, s is a peptide sequence associated with the candidate peptide, $H_1$ is a hypothesis that the peptide sequence s is the correct sequence of the experimental peptide, $H_0$ is a null-hypothesis that the peptide sequence s is an erroneous sequence of the experimental peptide, probabilities $P(E|D,s,H_1)$ and $P(E|D,s,H_0)$ are calculated based on the stochastic model, and the scoring further takes into account a charge state match between the experimental peptide and the candidate peptide; and outputting, in a user readable format, a result of the step of scoring the extended match E.

* * * * *